(12) United States Patent
Verfaillie et al.

(10) Patent No.: US 7,883,892 B2
(45) Date of Patent: Feb. 8, 2011

(54) SWINE MULTIPOTENT ADULT PROGENITOR CELLS

(75) Inventors: Catherine M. Verfaillie, White Bear Lake, MN (US); Lepeng Zeng, Minneapolis, MN (US); Jianyi Zhang, Plymouth, MN (US)

(73) Assignee: Regents of the University of Minnesota, St. Paul, MN (US)

( * ) Notice: Subject to any disclaimer, the term of this patent is extended or adjusted under 35 U.S.C. 154(b) by 712 days.

(21) Appl. No.: 11/725,962

(22) Filed: Mar. 20, 2007

(65) Prior Publication Data

US 2008/0031820 A1 Feb. 7, 2008

Related U.S. Application Data

(63) Continuation of application No. PCT/US2005/038979, filed on Oct. 26, 2005.

(60) Provisional application No. 60/622,183, filed on Oct. 26, 2004.

(51) Int. Cl.
C12N 5/074 (2010.01)
(52) U.S. Cl. ...................... 435/366; 424/93.7
(58) Field of Classification Search .................. None
See application file for complete search history.

(56) References Cited

U.S. PATENT DOCUMENTS

| 5,843,425 | A | 12/1998 | Sachs et al. | |
|---|---|---|---|---|
| 6,030,833 | A | 2/2000 | Seebach et al. | |
| 6,090,625 | A | 7/2000 | Abuljadayel et al. | |
| 7,015,037 | B1 * | 3/2006 | Furcht et al. | 435/372 |
| 2003/0157078 | A1 | 8/2003 | Hall et al. | |

FOREIGN PATENT DOCUMENTS

| WO | WO 96/23870 | 8/1996 |
|---|---|---|
| WO | WO-2006047743 A2 | 5/2006 |
| WO | WO-2006047743 A3 | 5/2006 |
| WO | WO-2006047743 C1 | 11/2006 |

OTHER PUBLICATIONS

Ringe J. et al. Porcine mesenchymal stem cells: Induction of distinct mesenchymal cell lineages, Cell Tissue Res (2002) vol. 307, pp. 321-327.*
Kovacevic, M., et al., "Erythroid Progenitor Cells from Pig Bone Marrow and Peripheral Blood", *The Veterinary Journal, 158*, www.idealibrary.com,(1999),196-203.
Communication and Accompanying Form 1149 dated Oct. 2, 2007 in related U.S. Appl. No. 11/238,234.
Second Communication and Accompanying Form PTO/SB/08b dated Dec. 24, 2008 in related U.S. Appl. No. 11/238,234.
Talbot et al., "Alkaline phosphatase staining of pig and sheep epiblast cells in culture" Molecular Reproduction and Development, 36:139-147 (1993).
Notarianni et al., "Maintenance and Differentiation in culture of pluripotential embryonic cell lines from pig blastocysts" J. Reprod Fert., Suppl. 41:51-56 (1990).
Notarianni et al., "Derivation of pluripotent, embryonic cell lines from the pig and sheep" J. Reprod. Fert., Suppl. 43:255-260 (1991).
Piedrahita et al., "Influence of feeder layer type on the efficiency of isolation of porcine embryo-derived cell lines" Theriogenology, 34:865-877 (1990).
Aldous et al., "Flawed stem cell data withdrawn" New Scientist; ( Feb. 15, 2007).
Aldous et al., "Fresh questions on stem cell findings" New Scientist; (Mar. 24, 2007).
Check "Stem cell paper corrected" Nature; 447:763 (2007) and Jiang et al., "Pluripotency of mesenchymal stem cells derived from adult bone marrow" Erratum in Nature; 447:879-880 (2007).
Chi, "Adult stem cell figure retracted" The Scientist; (Jun. 13, 2007).
Glenn, "Paper on versatility of adult stem cells comes under question" The Chronicle; (Feb. 26, 2007).
Holden, "Stem Cells. Controversial marrow cells coming into their own?" Science; 315:760-761 (2007).
Jiang et al., "Multipotent progenitor cells can be isolated from postnatal murine bone marrow, muscle, and brain" Exp. Hematol.; 30:896-904 (2002).
Jiang et al., "Pluripotency of mesenchymal stem cells derived from adult marrow, Supplemental Information for Verfaillie Corrigendum" Nature; 418:41-49 (2002).
Lerner et al., "Stem cell study was flawed, U panel finds" Star Tribune; (Feb. 27, 2007).
Noonan, "Limitations on the usefulness of adult stem cells" Patent Docs (Feb. 28, 2007).
Pincock, "Adult stem cell report questioned" The Scientist (Feb. 26, 2007).
Reyes et al., "Purification and ex vivo expansion of postnatal human marrow mesodermal progenitor cells" Blood; 98:2615-25 (2001).
Serafini et al., "Hematopoietic reconstitution by multipotent adult progenitor cells: precursors to long-term hematopoietic stem cell" J. Exp. Med.; 204:129-139 (2007).
Verfaillie, "Letter to the Editor" Experimental Hematology; (2007).
Giles, J., "The trouble with replication" Nature, 422:344-347 (2006).
Verfaillie, C.M., Multipotent adult progenitor cells: an update: Novartis Found Symp., 254:55-65 (2005).
Reya et al., Stem Cells, cancer, and cancer stem cells: Nature; 414:150-111 (2001).
Bjornson et al., "Turning brain into blood: a hematopoietic fate adopted by adult neural stem cells in vivo" Science; 283:534-537 (1999).

(Continued)

*Primary Examiner*—Jon P Weber
*Assistant Examiner*—Satyendra K Singh
(74) *Attorney, Agent, or Firm*—Tarolli, Sundheim, Covell & Tummino, L.L.P.

(57) ABSTRACT

The present invention provides swine cells of non-embryonic origin that can be maintained in culture in the undifferentiated state or differentiated to form cells of multiple cell types. Also provided are methods of isolation and culture, as well as uses for the cells, such as xenogeneic transplantation and/or tissue repair.

13 Claims, 16 Drawing Sheets

OTHER PUBLICATIONS

Bouwens, L., "Transdifferentiation versus stem cell hypothesis for the regeneration of islet beta-cells in the pancreas" Microscopy Research and Technique; 43:332-336 (1998).

Reyes et al., "Origin of endothelial progenitors in human postnatal bone marrow" J. Clin. Invest.; 109:1-10 (2002).

Reyes et al., "Characterization of multilineage mesodermal progenitor cells in adult marrow" Abstract No. 124, American Society for Hematology (2001).

Reyes et al., "Skeletal smooth and cardiac muscle differentiation from single adult marrow derived mesodermal progenitor cells" Abstract No. 2610, American Society for Hematology (2001).

Reyes et al., "In vitro and in vivo characterization of neural cells derived from mesenchymal stem cells" Abstract 2126, American Society for Hematology (2001).

Gupta et al., "Human bone marrow derived mesodermal progenitor cells (MPC) in vitro correct the biochemical abnormality in Hurler Syndrome" Abstract 1199, American Society for Hematology (2001).

Reyes et al., "Endothelial cells generated from human marrow derived mesenchymal stem cells (MSC)" Abstract No. 2276, American Society for Hematology (2001).

Zhao et al., "Immunohistochemical identification of multipotent adult progenitor cells from human bone marrow after transplantation into the rat brain" Brain Res Brain Res Protoc; 11:38-45 (2003).

Schwartz, R., "Multipotent adult progenitor cells from bone marrow differentiate into hepatocyte-like cells" J. Clin. Invest.; 109:1291-1302 (2002).

Zhao et al., "Human bone marrow stem cells exhibit neural phenotypes and ameliorate neurological deficits after grafting into the ischemic brain of rats" Exp Neurol; 174:11-20 (2002).

Qi et al., "Identification of genes responsible for osteoblast differentiation from human mesodermal progenitor cells" Nat. Acad. Sci. USA; 100:3305-3310 (2003).

Verfaillie, C. "Investigator Profile" Journal of Hematotherapy and Stem Cell Research; 11:441-444 (2002).

Verfaillie et al., "Stem cells: hype and reality" Hematology (Am Soc Hematol Educ Program); 369-391 (2002) PMID: 12446433 [PubMed—in process].

Verfaille, C., "Optimizing hematopoietic stem cell engraftment: a novel role for thrombopoeitin" J. Clin. Invest.; 110:303-304 (2002).

Verfaillie, C.M., "Meeting Report on an NHLBI Workshop on ex vivo expansion of stem cells, Jul. 29, 1999, Washington D.C. National Heart Lung and Blood Institute" Exp. Hematol.; 28:361-4 (2000).

Punzel et al., "The myeloid-lymphoid initiating cell (ML-IC) assay assesses the fate of multipotent human progenitors in vitro" Blood; 93:3750-3756 (1999).

Roy et al., "Expression and function of cell adhesion molecules on fetal liver, cord blood and bone marrow hematopoietic progenitors: implications for anatomical localization and developmental stage specific regulation of hematopoiesis" Exp. Hematol.; 27:302-312 (1999).

Verfaillie, C., "Stem cells in chronic myelogenous Leukemia" Hematol. Oncol. Clin. North Am.; 11:1079-114 (1997).

Prosper et al., "Phenotypic and functional characterization of long-term culture-initiating cells present in peripheral blood progenitor collections of normal donors treated with granulocyte colony-stimulating factor" Blood; 15:2033-2042 (1996).

Lodie et al., "Systematic analysis of reportedly distinct populations of multipotent bone marrow-derived stem cells reveals a lack of distinction" Tissue Engineering; 8:739-751 (2002).

Wade et al., "Scientists herald a versatile adult cell" The New York Times on the Web, Jan. 25, 2002.

Eglitis et al., "Hematopoietic cells differentiate into both microglia and macroglia in the brain of adult mice" Proc. Natl. Acad. Sci. USA; 94:4080-85 (1997).

Kopen et al., "Marrow stromal cells migrate throughout forebrain and cerebellum, and they differentiate into astrocytes after injection into neonatal mouse brains" Proc. Natl. Acad. Sci. USA; 96:10711-16 (1999).

Lagasse et al., "Purified hematopoietic stem cells can differentiate into hepatocytes in vivo" Nature Medicine; 6:1229-1234 (2000).

Wang, X. et al., "Cell fusion is the principal source of bone-marrow-derived hepatocytes" Nature; 422:897-901 (2003).

Anjos-Afonso and Bonnet, "Nonhematopoietic/endothelial SSE-1+ cells define the most primitive progenitors in the adult murine bone marrow mesenchymal compartment" Blood; 109:1298-1306 (2007).

Bertani et al., "Neurogenic potential of human mesenchymal stem cells revisited: analysis by immunostaining, time-lapse video and microarray" J Cell Sci.; 118:3925-36 (2005).

Bodnar et al., "Extension of life-span by introduction of telomerase into normal human cells" Science; 279:349-352 (1998).

Horwitz et al., "Clarification of the nomenclature for MSC: the international society for cellular therapy position paper" Cytotherapy; 7:393-395 (2005).

Lu et al., "Induction of bone marrow stromal cells to neurons: differentiation, transdifferentiation, or artifact" J Neurosci Res; 77:174-91 (2004).

Neuhuber et al., "Reevaluation of in vitro differentiation protocols for bone marrow stromal cells: disruption of actin cytoskeleton induces rapid morphological changes and mimics neuronal phenotype" J Neurosci Res; 77:192-204 (2004).

Zimmerman et al., "Lack of telomerase activity in human mesenchymal stem cells" Leukemia; 17:1146-1149 (2003).

Pagen Westphal, S., "Adult bone marrow eyed as source of stem cells" Boston Globe, Jan. 24, 2002.

Pagen Westphal, S., "Ultimate stem cell discovered" New Scientist, Jan. 23, 2002.

Rosford et al., "The octamer motif present in the Rex-1 promoter binds Oct. 1 and Oct. 3 expressed by EC cells and ES cells" Biochem. Biophys. Res. Comm.; 203:1795-1802 (1994).

Rosner et al., "Oct. 3 is a maternal factor required for the first mouse embryonic division" Cell; 64:1103-1110 (1991).

Pittenger et al., "Multilineage potential of adult human mesenchymal stem cells"; Science; 284:143-147 (1999).

Lamming et al., "Spontaneous circulation of myeloid-lymphoid-initiating cells and SCID-repopulating cells in sickle cell crisis" J. Clin. Invest.; 111:811-819 (2003).

Hilton et al., "Distribution and comparison of receptors for leukemia inhibitory factor on murine hemopoietic and hepatic cells" J. Cellular Physiology; 146:207-215 (1991).

Qi et al., "Identification of genes responsible for bone differentiation from human bone marrow derived multipotent adult stem cells (MASC)" Blood; 96:70-71 (2000).

Keene et al., "Phenotypic expression of transplanted human bone marrow-derived multipotent adult stem cells into the rat CNS" Exp. Neurology; 164:465 (2000).

Izadpanah et al., "Biologic properties of mesenchymal stem cells derived from bone marrow and adipose tissue" Journal of Cellular Biochemistry; 99:1285-1297 (2006).

Long et al., "Neural cell differentiation in vitro from adult human bone marrow mesenchymal stem cells" Stem Cells and Development; 14:65-69 (2005).

Moriscot et al., "Human bone marrow mesenchymal stem cell can express insulin and key transcription factors of the endocrine pancrease developmental pathway upon genetic and/or microenvironmental manipulation in vitro" Stem Cells; 23:594-604 (2005).

Sanchez-Ramos et al., "Adult bone marrow stromal cells differentiate into neural cells in vitro" Exp. Neurol.; 164:247-56 (2000).

Brazelton et al., "From marrow to brain: expression of neuronal phenotypes in adult mice" Science; 290:1775-9 (2000).

Clarke et al., "Generalized potential of adult neural stem cells" Science; 288: 1660-3 (2000).

Johansson et al., "Neural stem cells in the adult human brain" Exp. Cell. Res.; 253:733-6 (1999).

Mezey et al., "Turning blood into brain: cells bearing neuronal antigens generated in vivo from bone marrow" Science; 290:1779-82 (2000).

Morshead et al., "Hematopoietic competence is a rare property of neural stem cells that may depend on genetic and epigenetic alterations" Nat. Med.; 8:268-73 (2002).

Petersen et al., "Bone marrow as a potential source of hepatic oval cells" Science; 284:1168-70 (1999).

Scintu et al., "Differentiation of human bone marrow stem cells into cells with a neural phenotype: diverse effects of two specific treatments" BMC Neurosci.; 7:14 (2006).

Roobrouck et al., "Plasticity Between Human MSC and MAPC Mediated by Culture Conditions" Abstract, ISSCR, San Francisco Jun. 16-19, 2010.

U.S. Patent and Trademark Office, Office Action dated Jun. 24, 2005 in related U.S. Appl. No. 10/040,757.

U.S. Patent and Trademark Office, Office Action dated Jun. 27, 2008 in related U.S. Appl. No. 10/467,963.

U.S. Patent and Trademark Office, Office Action dated Oct. 15, 2009 in related U.S. Appl. No. 10/467,963.

U.S. Patent and Trademark Office, Office Action dated Apr. 7, 2008 in related U.S. Appl. No. 11/151,689.

U.S. Patent and Trademark Office, Office Action dated Jan. 4, 2006 in related U.S. Appl. No. 11/238,234.

U.S. Patent and Trademark Office, Office Action dated Aug. 29, 2006 in related U.S. Appl. No. 11/238,234.

U.S. Patent and Trademark Office, Office Action dated Apr. 3, 2007 in related U.S. Appl. No. 11/238,234.

U.S. Patent and Trademark Office, Office Action dated Oct. 7, 2008 in related U.S. Appl. No. 11/238,234.

* cited by examiner

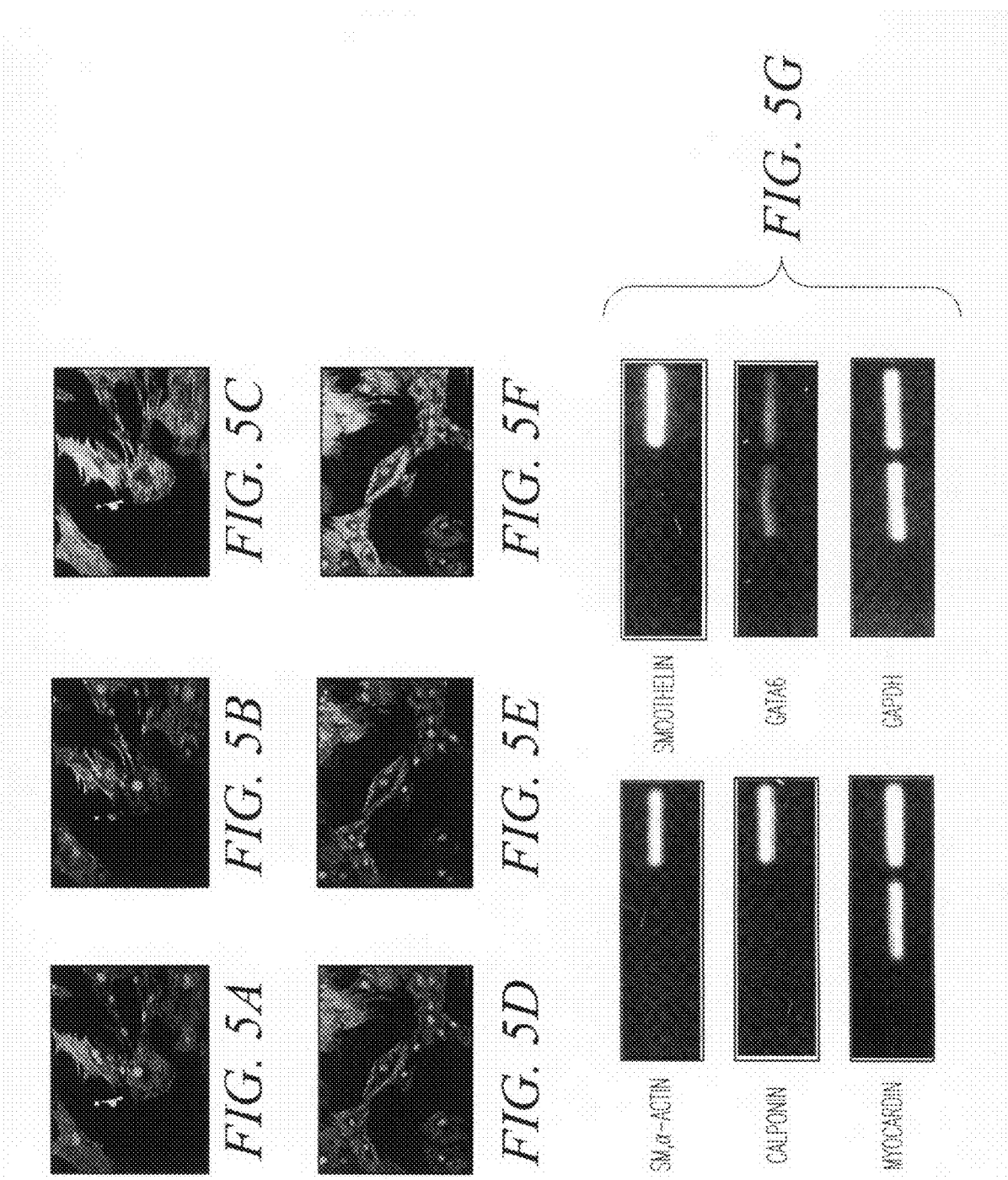

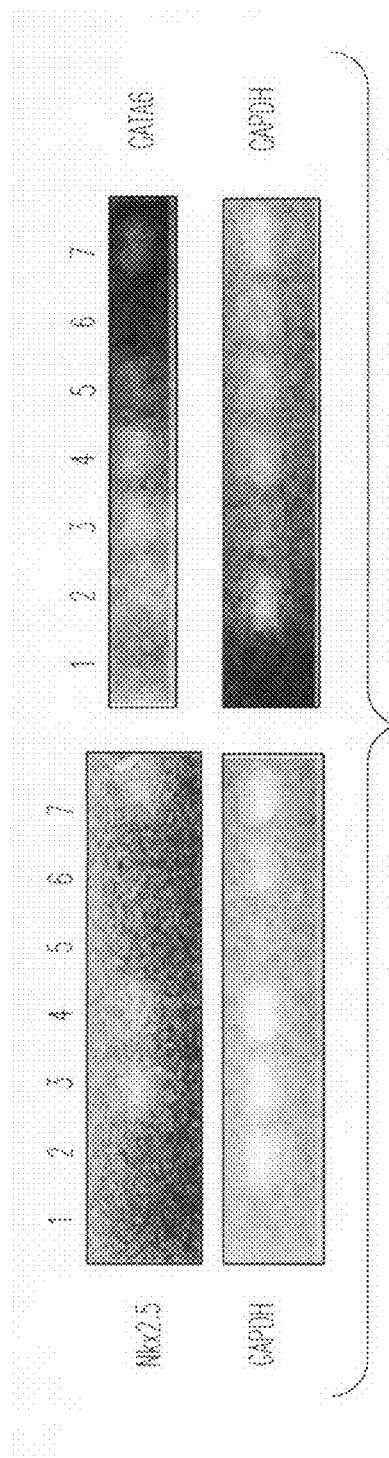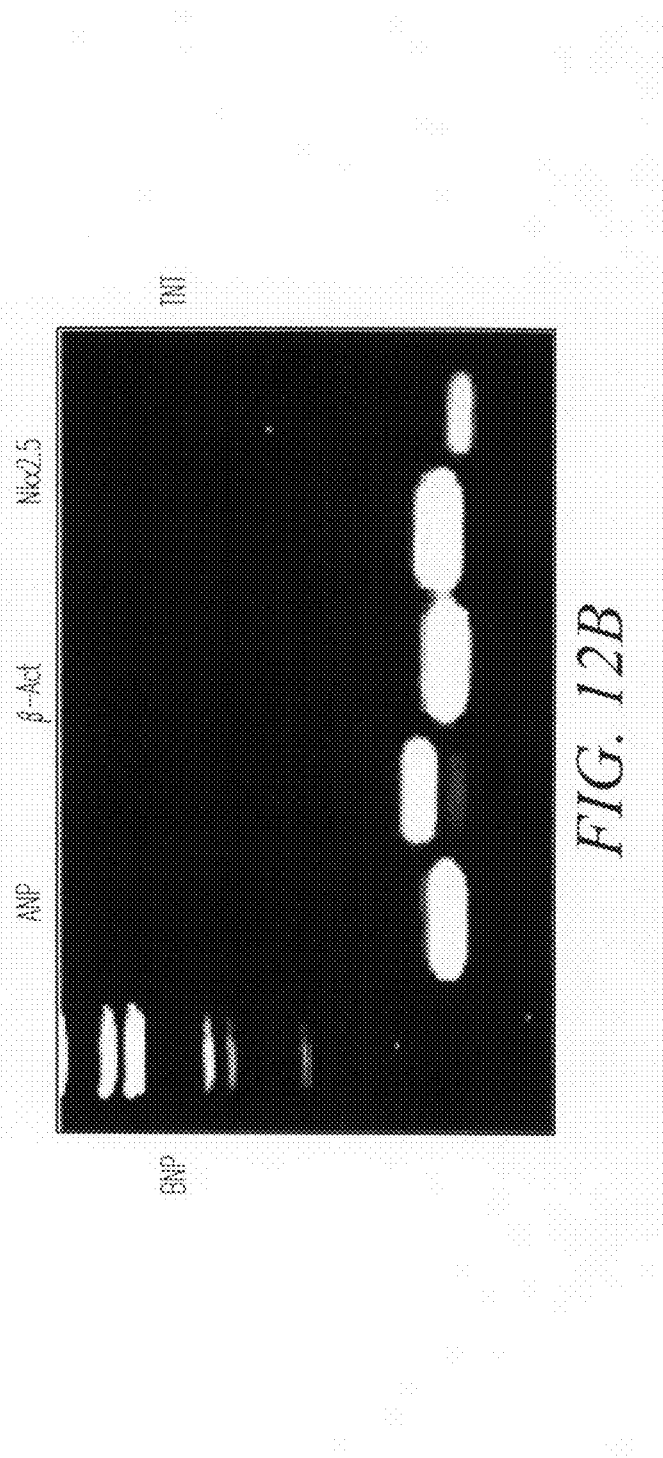
FIG. 12A
FIG. 12B

SEQUENCE LISTING

<160> NUMBER OF SEQ ID NOS: 78

<210> SEQ ID NO 1
<211> LENGTH: 20
<212> TYPE: DNA
<213> ORGANISM: Artificial Sequence
<220> FEATURE:
<223> OTHER INFORMATION: A synthetic primer

<400> SEQUENCE: 1
cttcggattt cgccttctcg                                             20

<210> SEQ ID NO 2
<211> LENGTH: 19
<212> TYPE: DNA
<213> ORGANISM: Artificial Sequence
<220> FEATURE:
<223> OTHER INFORMATION: A synthetic primer

<400> SEQUENCE: 2
gttccaggcc tacgagagg                                              19

<210> SEQ ID NO 3
<211> LENGTH: 21
<212> TYPE: DNA
<213> ORGANISM: Artificial Sequence
<220> FEATURE:
<223> OTHER INFORMATION: A synthetic primer

<400> SEQUENCE: 3
aaatggacct caaggcctac g                                           21

<210> SEQ ID NO 4
<211> LENGTH: 21
<212> TYPE: DNA
<213> ORGANISM: Artificial Sequence
<220> FEATURE:
<223> OTHER INFORMATION: A synthetic primer

<400> SEQUENCE: 4
gcagacctat gcacacttcc t                                           21

<210> SEQ ID NO 5
<211> LENGTH: 20
<212> TYPE: DNA
<213> ORGANISM: Artificial Sequence
<220> FEATURE:
<223> OTHER INFORMATION: A synthetic primer

<400> SEQUENCE: 5
gaggccctgc tgaacatcaa                                             20

<210> SEQ ID NO 6
<211> LENGTH: 20
<212> TYPE: DNA
<213> ORGANISM: Artificial Sequence
<220> FEATURE:
<223> OTHER INFORMATION: A synthetic primer

<400> SEQUENCE: 6
cccgcgacta cagccactac                                             20

<210> SEQ ID NO 7
<211> LENGTH: 21

```
<212> TYPE: DNA
<213> ORGANISM: Artificial Sequence
<220> FEATURE:
<223> OTHER INFORMATION: A synthetic primer

<400> SEQUENCE: 7
gtgttcccca cacggtcact a                                              21

<210> SEQ ID NO 8
<211> LENGTH: 21
<212> TYPE: DNA
<213> ORGANISM: Artificial Sequence
<220> FEATURE:
<223> OTHER INFORMATION: A synthetic primer

<400> SEQUENCE: 8
agaagacgac tgcggagtac a                                              21

<210> SEQ ID NO 9
<211> LENGTH: 23
<212> TYPE: DNA
<213> ORGANISM: Artificial Sequence
<220> FEATURE:
<223> OTHER INFORMATION: A synthetic primer

<400> SEQUENCE: 9
caaaactgtc gtgattccat gtc                                            23

<210> SEQ ID NO 10
<211> LENGTH: 19
<212> TYPE: DNA
<213> ORGANISM: Artificial Sequence
<220> FEATURE:
<223> OTHER INFORMATION: A synthetic primer

<400> SEQUENCE: 10
cgtgcagatg gacgaagac                                                 19

<210> SEQ ID NO 11
<211> LENGTH: 20
<212> TYPE: DNA
<213> ORGANISM: Artificial Sequence
<220> FEATURE:
<223> OTHER INFORMATION: A synthetic primer

<400> SEQUENCE: 11
gccatgatca agaaggacgg                                                20

<210> SEQ ID NO 12
<211> LENGTH: 21
<212> TYPE: DNA
<213> ORGANISM: Artificial Sequence
<220> FEATURE:
<223> OTHER INFORMATION: A synthetic primer

<400> SEQUENCE: 12
tgctctgggt tcgtcagagt c                                              21

<210> SEQ ID NO 13
<211> LENGTH: 22
<212> TYPE: DNA
<213> ORGANISM: Artificial Sequence
<220> FEATURE:
<223> OTHER INFORMATION: A synthetic primer

<400> SEQUENCE: 13
```

```
ggacaccacc caaatatcat ca                                              22

<210> SEQ ID NO 14
<211> LENGTH: 20
<212> TYPE: DNA
<213> ORGANISM: Artificial Sequence
<220> FEATURE:
<223> OTHER INFORMATION: A synthetic primer

<400> SEQUENCE: 14
cagcaacggc tactcacaaa                                                 20

<210> SEQ ID NO 15
<211> LENGTH: 19
<212> TYPE: DNA
<213> ORGANISM: Artificial Sequence
<220> FEATURE:
<223> OTHER INFORMATION: A synthetic primer

<400> SEQUENCE: 15
gtgatccggg tctggtttc                                                  19

<210> SEQ ID NO 16
<211> LENGTH: 20
<212> TYPE: DNA
<213> ORGANISM: Artificial Sequence
<220> FEATURE:
<223> OTHER INFORMATION: A synthetic primer

<400> SEQUENCE: 16
gggctgagtc tgaccacttc                                                 20

<210> SEQ ID NO 17
<211> LENGTH: 19
<212> TYPE: DNA
<213> ORGANISM: Artificial Sequence
<220> FEATURE:
<223> OTHER INFORMATION: A synthetic primer

<400> SEQUENCE: 17
cagagctgga ggcactgaa                                                  19

<210> SEQ ID NO 18
<211> LENGTH: 21
<212> TYPE: DNA
<213> ORGANISM: Artificial Sequence
<220> FEATURE:
<223> OTHER INFORMATION: A synthetic primer

<400> SEQUENCE: 18
aaagaccaac ctgcagctct g                                               21

<210> SEQ ID NO 19
<211> LENGTH: 20
<212> TYPE: DNA
<213> ORGANISM: Artificial Sequence
<220> FEATURE:
<223> OTHER INFORMATION: A synthetic primer

<400> SEQUENCE: 19
cacacacaca cacacgcatt                                                 20

<210> SEQ ID NO 20
<211> LENGTH: 24
<212> TYPE: DNA
<213> ORGANISM: Artificial Sequence
```

```
<220> FEATURE:
<223> OTHER INFORMATION: A synthetic primer

<400> SEQUENCE: 20
gaggcagagc tcctgactac aaac                                            24

<210> SEQ ID NO 21
<211> LENGTH: 21
<212> TYPE: DNA
<213> ORGANISM: Artificial Sequence
<220> FEATURE:
<223> OTHER INFORMATION: A synthetic primer

<400> SEQUENCE: 21
gtccctggat aacatcaccc a                                               21

<210> SEQ ID NO 22
<211> LENGTH: 19
<212> TYPE: DNA
<213> ORGANISM: Artificial Sequence
<220> FEATURE:
<223> OTHER INFORMATION: A synthetic primer

<400> SEQUENCE: 22
gttggtatcc ggggacttc                                                  19

<210> SEQ ID NO 23
<211> LENGTH: 22
<212> TYPE: DNA
<213> ORGANISM: Artificial Sequence
<220> FEATURE:
<223> OTHER INFORMATION: A synthetic primer

<400> SEQUENCE: 23
ggagtcagca gatggatgaa ct                                              22

<210> SEQ ID NO 24
<211> LENGTH: 19
<212> TYPE: DNA
<213> ORGANISM: Artificial Sequence
<220> FEATURE:
<223> OTHER INFORMATION: A synthetic primer

<400> SEQUENCE: 24
gcatcacaca ggctggaac                                                  19

<210> SEQ ID NO 25
<211> LENGTH: 22
<212> TYPE: DNA
<213> ORGANISM: Artificial Sequence
<220> FEATURE:
<223> OTHER INFORMATION: A synthetic primer

<400> SEQUENCE: 25
agctggattg agggacttac tg                                              22

<210> SEQ ID NO 26
<211> LENGTH: 21
<212> TYPE: DNA
<213> ORGANISM: Artificial Sequence
<220> FEATURE:
<223> OTHER INFORMATION: A synthetic primer

<400> SEQUENCE: 26
tgctctgggt tcgtcagagt c                                               21
```

<210> SEQ ID NO 27
<211> LENGTH: 21
<212> TYPE: DNA
<213> ORGANISM: Artificial Sequence
<220> FEATURE:
<223> OTHER INFORMATION: A synthetic primer

<400> SEQUENCE: 27
ccttggaagc ttagccaggt c                                              21

<210> SEQ ID NO 28
<211> LENGTH: 19
<212> TYPE: DNA
<213> ORGANISM: Artificial Sequence
<220> FEATURE:
<223> OTHER INFORMATION: A synthetic primer

<400> SEQUENCE: 28
tgaccaaaca gcccttctg                                                 19

<210> SEQ ID NO 29
<211> LENGTH: 17
<212> TYPE: DNA
<213> ORGANISM: Artificial Sequence
<220> FEATURE:
<223> OTHER INFORMATION: A synthetic primer

<400> SEQUENCE: 29
atggccaggc ttcctgg                                                   17

<210> SEQ ID NO 30
<211> LENGTH: 20
<212> TYPE: DNA
<213> ORGANISM: Artificial Sequence
<220> FEATURE:
<223> OTHER INFORMATION: A synthetic primer

<400> SEQUENCE: 30
gcccaggaca gttctcagtt                                                20

<210> SEQ ID NO 31
<211> LENGTH: 17
<212> TYPE: DNA
<213> ORGANISM: Artificial Sequence
<220> FEATURE:
<223> OTHER INFORMATION: A synthetic primer

<400> SEQUENCE: 31
tccagagcgt cgccaag                                                   17

<210> SEQ ID NO 32
<211> LENGTH: 24
<212> TYPE: DNA
<213> ORGANISM: Artificial Sequence
<220> FEATURE:
<223> OTHER INFORMATION: A synthetic primer

<400> SEQUENCE: 32
tgcaggacta tcttggagtt ctca                                           24

<210> SEQ ID NO 33
<211> LENGTH: 20
<212> TYPE: DNA
<213> ORGANISM: Artificial Sequence
<220> FEATURE:
<223> OTHER INFORMATION: A synthetic primer

<400> SEQUENCE: 33
tgggtcatgg agagcagagg                                            20

<210> SEQ ID NO 34
<211> LENGTH: 20
<212> TYPE: DNA
<213> ORGANISM: Artificial Sequence
<220> FEATURE:
<223> OTHER INFORMATION: A synthetic primer

<400> SEQUENCE: 34
acgactccac cttcgatcac                                            20

<210> SEQ ID NO 35
<211> LENGTH: 25
<212> TYPE: DNA
<213> ORGANISM: Artificial Sequence
<220> FEATURE:
<223> OTHER INFORMATION: A synthetic primer

<400> SEQUENCE: 35
ttctgttacc atcaggaaca aacct                                      25

<210> SEQ ID NO 36
<211> LENGTH: 21
<212> TYPE: DNA
<213> ORGANISM: Artificial Sequence
<220> FEATURE:
<223> OTHER INFORMATION: A synthetic primer

<400> SEQUENCE: 36
gttccacaaa tcttggcctt t                                          21

<210> SEQ ID NO 37
<211> LENGTH: 19
<212> TYPE: DNA
<213> ORGANISM: Artificial Sequence
<220> FEATURE:
<223> OTHER INFORMATION: A synthetic primer

<400> SEQUENCE: 37
tccagttctc ccgcgaagt                                             19

<210> SEQ ID NO 38
<211> LENGTH: 20
<212> TYPE: DNA
<213> ORGANISM: Artificial Sequence
<220> FEATURE:
<223> OTHER INFORMATION: A synthetic primer

<400> SEQUENCE: 38
caggcaagtc actgtgtggc                                            20

<210> SEQ ID NO 39
<211> LENGTH: 21
<212> TYPE: DNA
<213> ORGANISM: Artificial Sequence
<220> FEATURE:
<223> OTHER INFORMATION: A synthetic primer

<400> SEQUENCE: 39
aagtccagga gattcccatg g                                          21

<210> SEQ ID NO 40

```
<211> LENGTH: 20
<212> TYPE: DNA
<213> ORGANISM: Artificial Sequence
<220> FEATURE:
<223> OTHER INFORMATION: A synthetic primer

<400> SEQUENCE: 40
attcttcccc atgaggctct                                               20

<210> SEQ ID NO 41
<211> LENGTH: 20
<212> TYPE: DNA
<213> ORGANISM: Artificial Sequence
<220> FEATURE:
<223> OTHER INFORMATION: A synthetic primer

<400> SEQUENCE: 41
catgggagtt cctgtcatcc                                               20

<210> SEQ ID NO 42
<211> LENGTH: 18
<212> TYPE: DNA
<213> ORGANISM: Artificial Sequence
<220> FEATURE:
<223> OTHER INFORMATION: A synthetic primer

<400> SEQUENCE: 42
ccgagtgaac gtcgtcct                                                 18

<210> SEQ ID NO 43
<211> LENGTH: 20
<212> TYPE: DNA
<213> ORGANISM: Artificial Sequence
<220> FEATURE:
<223> OTHER INFORMATION: A synthetic primer

<400> SEQUENCE: 43
catctcccac ttggtgttcc                                               20

<210> SEQ ID NO 44
<211> LENGTH: 20
<212> TYPE: DNA
<213> ORGANISM: Artificial Sequence
<220> FEATURE:
<223> OTHER INFORMATION: A synthetic primer

<400> SEQUENCE: 44
tccactggga ccgtctgttc                                               20

<210> SEQ ID NO 45
<211> LENGTH: 19
<212> TYPE: DNA
<213> ORGANISM: Artificial Sequence
<220> FEATURE:
<223> OTHER INFORMATION: A synthetic primer

<400> SEQUENCE: 45
ggagctcccg tgttgatct                                                19

<210> SEQ ID NO 46
<211> LENGTH: 18
<212> TYPE: DNA
<213> ORGANISM: Artificial Sequence
<220> FEATURE:
<223> OTHER INFORMATION: A synthetic primer

<400> SEQUENCE: 46
```

```
gtcccgtcct cccagctt                                                    18

<210> SEQ ID NO 47
<211> LENGTH: 19
<212> TYPE: DNA
<213> ORGANISM: Artificial Sequence
<220> FEATURE:
<223> OTHER INFORMATION: A synthetic primer

<400> SEQUENCE: 47
cgtggtccgt cttggcttt                                                   19

<210> SEQ ID NO 48
<211> LENGTH: 20
<212> TYPE: DNA
<213> ORGANISM: Artificial Sequence
<220> FEATURE:
<223> OTHER INFORMATION: A synthetic primer

<400> SEQUENCE: 48
cgttggaact gatggagttg                                                  20

<210> SEQ ID NO 49
<211> LENGTH: 20
<212> TYPE: DNA
<213> ORGANISM: Artificial Sequence
<220> FEATURE:
<223> OTHER INFORMATION: A synthetic primer

<400> SEQUENCE: 49
gaagacccgg gtatctttgg                                                  20

<210> SEQ ID NO 50
<211> LENGTH: 21
<212> TYPE: DNA
<213> ORGANISM: Artificial Sequence
<220> FEATURE:
<223> OTHER INFORMATION: A synthetic primer

<400> SEQUENCE: 50
agcaggagtg tcactgtggt c                                                21

<210> SEQ ID NO 51
<211> LENGTH: 18
<212> TYPE: DNA
<213> ORGANISM: Artificial Sequence
<220> FEATURE:
<223> OTHER INFORMATION: A synthetic primer

<400> SEQUENCE: 51
gcatggagcg gttgatct                                                    18

<210> SEQ ID NO 52
<211> LENGTH: 20
<212> TYPE: DNA
<213> ORGANISM: Artificial Sequence
<220> FEATURE:
<223> OTHER INFORMATION: A synthetic primer

<400> SEQUENCE: 52
caggcaagtc actgtgtggc                                                  20

<210> SEQ ID NO 53
<211> LENGTH: 20
<212> TYPE: DNA
```

```
<213> ORGANISM: Artificial Sequence
<220> FEATURE:
<223> OTHER INFORMATION: A synthetic primer

<400> SEQUENCE: 53
ttatgcagcg tgcaatgagt                                              20

<210> SEQ ID NO 54
<211> LENGTH: 20
<212> TYPE: DNA
<213> ORGANISM: Artificial Sequence
<220> FEATURE:
<223> OTHER INFORMATION: A synthetic primer

<400> SEQUENCE: 54
gagctcagtc ccagttccaa                                              20

<210> SEQ ID NO 55
<211> LENGTH: 20
<212> TYPE: DNA
<213> ORGANISM: Artificial Sequence
<220> FEATURE:
<223> OTHER INFORMATION: A synthetic primer

<400> SEQUENCE: 55
ggtcaaggca gaacagaagc                                              20

<210> SEQ ID NO 56
<211> LENGTH: 20
<212> TYPE: DNA
<213> ORGANISM: Artificial Sequence
<220> FEATURE:
<223> OTHER INFORMATION: A synthetic primer

<400> SEQUENCE: 56
atccaatccg acagttcctg                                              20

<210> SEQ ID NO 57
<211> LENGTH: 20
<212> TYPE: DNA
<213> ORGANISM: Artificial Sequence
<220> FEATURE:
<223> OTHER INFORMATION: A synthetic primer

<400> SEQUENCE: 57
tctatcctct cctccagcca                                              20

<210> SEQ ID NO 58
<211> LENGTH: 20
<212> TYPE: DNA
<213> ORGANISM: Artificial Sequence
<220> FEATURE:
<223> OTHER INFORMATION: A synthetic primer

<400> SEQUENCE: 58
caacaggtgc aagaacagga                                              20

<210> SEQ ID NO 59
<211> LENGTH: 21
<212> TYPE: DNA
<213> ORGANISM: Artificial Sequence
<220> FEATURE:
<223> OTHER INFORMATION: A synthetic primer

<400> SEQUENCE: 59
cagcgcctct aatcctctcc t                                            21
```

```
<210> SEQ ID NO 60
<211> LENGTH: 20
<212> TYPE: DNA
<213> ORGANISM: Artificial Sequence
<220> FEATURE:
<223> OTHER INFORMATION: A synthetic primer

<400> SEQUENCE: 60
tatccctggc agttctgagg                                            20

<210> SEQ ID NO 61
<211> LENGTH: 18
<212> TYPE: DNA
<213> ORGANISM: Artificial Sequence
<220> FEATURE:
<223> OTHER INFORMATION: A synthetic primer

<400> SEQUENCE: 61
cctcaagggc ggcaagaa                                              18

<210> SEQ ID NO 62
<211> LENGTH: 18
<212> TYPE: DNA
<213> ORGANISM: Artificial Sequence
<220> FEATURE:
<223> OTHER INFORMATION: A synthetic primer

<400> SEQUENCE: 62
cctcaggatg gggcagat                                              18

<210> SEQ ID NO 63
<211> LENGTH: 19
<212> TYPE: DNA
<213> ORGANISM: Artificial Sequence
<220> FEATURE:
<223> OTHER INFORMATION: A synthetic primer

<400> SEQUENCE: 63 cttttttcagc tttctcttg                                            19

<210> SEQ ID NO 64
<211> LENGTH: 18
<212> TYPE: DNA
<213> ORGANISM: Artificial Sequence
<220> FEATURE:
<223> OTHER INFORMATION: A synthetic primer

<400> SEQUENCE: 64
acccctagtt catcctca                                              18

<210> SEQ ID NO 65
<211> LENGTH: 21
<212> TYPE: DNA
<213> ORGANISM: Artificial Sequence
<220> FEATURE:
<223> OTHER INFORMATION: A synthetic primer

<400> SEQUENCE: 65
ctcctactcc agcccctacc c                                          21

<210> SEQ ID NO 66
<211> LENGTH: 24
<212> TYPE: DNA
<213> ORGANISM: Artificial Sequence
<220> FEATURE:
```

```
<223> OTHER INFORMATION: A synthetic primer

<400> SEQUENCE: 66
cctgctgacg tcttcgattt gtta                                          24

<210> SEQ ID NO 67
<211> LENGTH: 20
<212> TYPE: DNA
<213> ORGANISM: Artificial Sequence
<220> FEATURE:
<223> OTHER INFORMATION: A synthetic primer

<400> SEQUENCE: 67
caggtgctgc aagtcttcct                                               20

<210> SEQ ID NO 68
<211> LENGTH: 20
<212> TYPE: DNA
<213> ORGANISM: Artificial Sequence
<220> FEATURE:
<223> OTHER INFORMATION: A synthetic primer

<400> SEQUENCE: 68
gaagtccctg gaagccagat                                               20

<210> SEQ ID NO 69
<211> LENGTH: 20
<212> TYPE: DNA
<213> ORGANISM: Artificial Sequence
<220> FEATURE:
<223> OTHER INFORMATION: A synthetic primer

<400> SEQUENCE: 69
gttcaagcca atccactggt                                               20

<210> SEQ ID NO 70
<211> LENGTH: 20
<212> TYPE: DNA
<213> ORGANISM: Artificial Sequence
<220> FEATURE:
<223> OTHER INFORMATION: A synthetic primer

<400> SEQUENCE: 70
cagtcacacc tgagcagcat                                               20

<210> SEQ ID NO 71
<211> LENGTH: 19
<212> TYPE: DNA
<213> ORGANISM: Artificial Sequence
<220> FEATURE:
<223> OTHER INFORMATION: A synthetic primer

<400> SEQUENCE: 71
agctcacgcg tcatcagag                                                19

<210> SEQ ID NO 72
<211> LENGTH: 19
<212> TYPE: DNA
<213> ORGANISM: Artificial Sequence
<220> FEATURE:
<223> OTHER INFORMATION: A synthetic primer

<400> SEQUENCE: 72
cactcaccgc agtggtagg                                                19
```

```
<210> SEQ ID NO 73
<211> LENGTH: 20
<212> TYPE: DNA
<213> ORGANISM: Artificial Sequence
<220> FEATURE:
<223> OTHER INFORMATION: A synthetic primer

<400> SEQUENCE: 73
cactgagcac caggttgtgt                                                    20

<210> SEQ ID NO 74
<211> LENGTH: 21
<212> TYPE: DNA
<213> ORGANISM: Artificial Sequence
<220> FEATURE:
<223> OTHER INFORMATION: A synthetic primer

<400> SEQUENCE: 74
cctgttgctg tagccaaatt c                                                  21

<210> SEQ ID NO 75
<211> LENGTH: 20
<212> TYPE: DNA
<213> ORGANISM: Artificial Sequence
<220> FEATURE:
<223> OTHER INFORMATION: A synthetic primer

<400> SEQUENCE: 75
tttgctgcaa tcgtctgagt                                                    20

<210> SEQ ID NO 76
<211> LENGTH: 20
<212> TYPE: DNA
<213> ORGANISM: Artificial Sequence
<220> FEATURE:
<223> OTHER INFORMATION: A synthetic primer

<400> SEQUENCE: 76
ggaattcaga ccaggaaacg                                                    20

<210> SEQ ID NO 77
<211> LENGTH: 20
<212> TYPE: DNA
<213> ORGANISM: Artificial Sequence
<220> FEATURE:
<223> OTHER INFORMATION: A synthetic primer

<400> SEQUENCE: 77
gtgcagacct tctccaacct                                                    20

<210> SEQ ID NO 78
<211> LENGTH: 21
<212> TYPE: DNA
<213> ORGANISM: Artificial Sequence
<220> FEATURE:
<223> OTHER INFORMATION: A synthetic primer

<400> SEQUENCE: 78
gccttctgac acagacttgg t                                                  21
```

SWINE MULTIPOTENT ADULT PROGENITOR CELLS

RELATED APPLICATIONS

This application is a continuation under 35 U.S.C. §111(a) of International Application No. PCT/US2005/038979, filed Oct. 26, 2005 and published in English as WO 2006/047743 on May 4, 2006, which application claims priority from U.S. Provisional Application Ser. No. 60/622,183 filed Oct. 26, 2004, which application is herein incorporated by reference.

GOVERNMENT FUNDING

The invention described herein was developed with support from the National Institutes of Health grant number R01 HL 67828. The U.S. Government may have certain rights in the invention.

FIELD OF THE INVENTION

The present invention relates generally to swine multipotent adult progenitor cells (sMAPCs) and clinical and preclinical uses for those cells.

BACKGROUND OF THE INVENTION

Stem Cells

The embryonic stem (ES) cell has unlimited self-renewal and can differentiate into all tissue types. ES cells are derived from the inner cell mass of the blastocyst or primordial germ cells from a post-implantation embryo (embryonic germ cells or EG cells). ES and EG cells have been derived from mouse, and, more recently, from non-human primates and humans. When introduced into blastocysts, ES cells can contribute to all tissues. A drawback to ES cell therapy is that, when transplanted in post-natal animals, ES and EG cells generate teratomas (Bjorklund 2002).

ES (and EG) cells can be identified by positive staining with the antibodies SSEA 1 (mouse) and SSEA 4 (human). At the molecular level, ES and EG cells express a number of transcription factors specific for these undifferentiated cells. These include Oct-4 and rex-1. Rex expression depends on Oct-4. Also found are the LIF-R (in mouse) and the transcription factors sox-2 and rox-1. Rox-1 and sox-2 are also expressed in non-ES cells. Another hallmark of ES cells is the presence of telomerase, which provides these cells with an unlimited self-renewal potential in vitro.

Oct-4 (Oct 3 in humans) is a transcription factor expressed in the pregastrulation embryo, early cleavage stage embryo, cells of the inner cell mass of the blastocyst, and embryonic carcinoma (EC) cells (Nichols J., et al 1998), and is downregulated when cells are induced to differentiate. Expression of Oct-4 plays a role in determining early steps in embryogenesis and differentiation. Oct-4, in combination with Rox-1, causes transcriptional activation of the Zn-finger protein Rex-1, also required for maintaining ES in an undifferentiated state (Rosfjord and Rizzino A. 1997; Ben-Shushan E, et al. 1998). In addition, sox-2, expressed in ES/EC, but also in other more differentiated cells, is needed together with Oct-4 to retain the undifferentiated state of ES/EC (Uwanogho D et al. 1995). Maintenance of murine ES cells and primordial germ cells requires LIF.

The Oct-4 gene (Oct 3 in humans) is transcribed into at least two splice variants in humans, Oct 3A and Oct 3B. The Oct 3B splice variant is found in many differentiated cells, whereas the Oct 3A splice variant (also previously designated Oct 3/4) is reported to be specific for the undifferentiated embryonic stem cell (Shimozaki et al. 2003).

Adult stem cells have been identified in most tissues. Hematopoietic stem cells are mesoderm-derived and have been purified based on cell surface markers and functional characteristics. The hematopoietic stem cell, isolated from bone marrow, blood, cord blood, fetal liver and yolk sac, is the progenitor cell that reinitiates hematopoiesis for the life of a recipient and generates multiple hematopoietic lineages. Hematopoietic stem cells can repopulate the erythroid, neutrophil-macrophage, megakaryocyte and lymphoid hemopoietic cell pool. Stem cells which differentiate only to form cells of hematopoietic lineage, however, are unable to provide a source of cells for repair of other damaged tissues, for example, heart.

Neural stem cells were initially identified in the subventricular zone and the olfactory bulb of fetal brain. Several studies in rodents, and more recently also non-human primates and humans, have shown that stem cells continue to be present in adult brain. These stem cells can proliferate in vivo and continuously regenerate at least some neuronal cells in vivo. When cultured ex vivo, neural stem cells can be induced to proliferate, as well as to differentiate into different types of neurons and glial cells. When transplanted into the brain, neural stem cells can engraft and generate neural cells and glial cells.

Mesenchymal stem cells, originally derived from the embryonal mesoderm and isolated from adult bone marrow, can differentiate to form muscle, bone, cartilage, fat, marrow, stroma, and tendon. During embryogenesis, the mesoderm develops into limb-bud mesoderm, tissue that generates bone, cartilage, fat, skeletal muscle and possibly endothelium. Mesoderm also differentiates to visceral mesoderm, which can give rise to cardiac muscle, smooth muscle, or blood islands consisting of endothelium and hematopoietic progenitor cells. Primitive mesodermal or mesenchymal stem cells, therefore, could provide a source for a number of cell and tissue types. Of the many mesenchymal stem cells that have been described, all have demonstrated limited differentiation to form only those differentiated cells generally considered to be of mesenchymal origin. To date, the most potent mesenchymal stem cell reported is the cell isolated by Pittenger, et al. (1999) and U.S. Pat. No. 5,827,740 (SH2$^+$ SH4$^+$ CD29$^+$ CD44$^+$ CD71$^+$ CD90$^+$ CD106$^+$ CD120a$^+$ CD124$^+$ CD14$^-$ CD34$^-$ CD45$^-$). This cell is capable of differentiating to form a number of cell types of mesenchymal origin, but is apparently limited in differentiation potential to cells of the mesenchymal lineage, as the team who isolated it noted that hematopoietic cells were never identified in the expanded cultures.

Until recently, it was thought that organ-specific stem cells could only differentiate into cells of the same tissue. A number of recent publications have suggested that adult organ-specific stem cells may be capable of differentiating into cells of different tissues. A number of studies have shown that cells transplanted at the time of a bone marrow transplant can differentiate into skeletal muscle (Ferrari, 1998; Gussoni, 1999). Jackson published that muscle satellite cells can differentiate into hemopoietic cells (Jackson, 1999). Other studies have shown that stem cells from one embryonal layer (for instance splanchnic mesoderm) can differentiate into tissues thought to be derived during embryogenesis from a different embryonal layer. For instance, in humans that underwent marrow transplantation, endothelial cells are at least in part derived from the marrow donor (Takahashi, 1999 and 2000). There are also reports that in rodents and humans hepatic epithelial cells and biliary duct epithelial cells are derived from the donor marrow (Petersen, 1999; Theise 2000a and 2000b). Finally, Clarke et al. reported that neural stem cells injected into blastocysts can contribute to all tissues of the chimeric mouse (Clarke 2000). Most of these studies have not conclusively demonstrated that a single cell can differentiate into tissues of different organs. Indeed most investigators did not identify the phenotype of the initiating cell.

Non-embryonic multipotent stem cells that are not lineage-specific or tissue-specific have been reported to occur in various tissues of human, rat and mouse (PCT/US00/21387; PCT/US02/04652). For example, this type of stem cell has been reported to occur in placenta (U.S. 2004/0028660; U.S. 2004/0048372; U.S. 2003/0032179), cord blood (U.S. 2002/0164794), and bone marrow (U.S. 2004/0058412; U.S. 2003/0059414).

SUMMARY OF THE INVENTION

The present invention provides isolated non-ES, non-EG, non-germ swine cells, wherein the cells can differentiate into at least two embryonic germ layer lineages, including ectodermal, endodermal, and mesodermal cell types (referred to herein as sMAPC). sMAPCs have the capacity to be induced to differentiate in vitro, ex vivo or in vivo. sMAPCs can differentiate into all cell types of a body, such as a mammalian body, including a human. For example, sMAPCs can differentiate to cartilage (chondrocyte), osteoblast, adipocyte, fibroblast, marrow stroma, skeletal muscle, endothelial, neural, hepatocyte (hepatic), pancreatic, hematopoietic, glial, neuronal, oligodendrocyte, blood vessel, cardiomyocyte (cardiac muscle), ocular, epithelial, or smooth muscle cell types. The cells of the invention include clonal or nonclonal populations of sMAPC, including populations of sMAPCs enriched to various degrees. sMAPC can express Oct 3a (Oct 3/4) and active telomerase. In addition, the cells maintain telomere length after extended in vitro culture (for example, cells that have undergone at least about 50 or more population doublings). sMAPC have a surface phenotype equivalent to human MAPCs, can be distinguished from swine hematopoietic stem cells by the absence of CD45 and MHC class II expression. The cells can be genetically modified to express a preselected gene or produce a protein of interest (e.g., a cytokine or growth factor).

One embodiment provides compositions containing the sMAPCs described herein and a carrier, including a pharmaceutically acceptable carrier or cell culture medium. Another embodiment includes compositions containing differentiated progeny or tissues derived from sMAPCs. One embodiment provides a method to prepare a composition comprising mixing the sMAPCs described herein with a carrier, including a pharmaceutically acceptable carrier or cell culture medium.

One embodiment provides a method of treating a disease or injury by administering to a subject an amount of sMAPC or progeny differentiated therefrom effective to treat the disease or injury. The method can be used to treat any subject, including, but not limited to, mammals, such as a human or swine. The disease includes, but is not limited to, cardiovascular disease, liver disease, renal disease, genetic disease, or diabetes. The disease also includes infection (e.g., hepatitis). The injury includes, but is not limited to, traumatic injury, mechanical injury, including, but not limited to, surgical injury, diet induced injury (including, but not limited to, chemicals, drugs, and/or alcohol induced injury). sMAPCs, progeny differentiated therefrom, or a combination thereof can be administered by a variety of techniques including, but not limited to, local or systemic injection. Additionally, the cells of the invention can be encapsulated prior to administration.

Another embodiment provides a bioreactor containing sMAPCs, progeny differentiated therefrom, or a combination thereof. For example, a bioreactor can include hepatocytes or renal cells differentiated from sMAPCs for use in an in vivo or extracorporeal liver or kidney assist device to treat, for example, a human with liver or kidney failure.

One embodiment provides a method for determining whether swine cell-based therapy is effective to treat an injury or disease in a subject by administering to a non-human subject having said injury or disease sMAPCs or progeny differentiated therefrom and determining whether one or more of the symptoms associated with the injury or disease are ameliorated. The subject can include, but is not limited to, swine. The administration routes include, but are not limited to, local or systemic administration and the cells can be encapsulated prior to administration. The disease includes, but is not limited to, cardiac, renal, hepatic, pancreatic or metabolic disease. For example, the hepatic disease includes, but is not limited to, cirrhosis or hepatitis, and the cardiac disease includes, but is not limited to, congestive heart failure, coronary artery disease, myocardial infarction, hypertension, restenosis, angina pectoris, rheumatic heart disease, congenital heart defect, ischemia, atherosclerosis, cardiac arrhythmia, myocarditis, or endocarditis. The disease also includes infection (e.g., hepatitis). The injury includes, but is not limited to, traumatic injury, mechanical injury, including, but not limited to, surgical injury, diet induced injury (including, but not limited to, chemicals, drugs, and/or alcohol induced injury).

Another embodiment provides methods to isolate and expand a population of MAPCs, for example, swine MAPCs. One embodiment provides a method to isolate non-ES, non-EG, non-germ swine cells that differentiate into at least two ectodermal, endodermal, and mesodermal cell types comprising: a) obtaining tissue from a swine; b) establishing a population of adherent cells; c) depleting said population of $CD45^+$ cells; and d) culturing $CD45^-$ cells in media supplemented with growth factors. In one embodiment, the step of depleting comprises culturing the cells in media supplemented with growth factors, or using negative or positive selection using monoclonal or polyclonal antibodies. In one embodiment the growth factor comprises PDGF, EGF or a combination thereof. Another embodiment further comprises incubating the tissue at 4° C. for 36 to 48 hours prior to establishing a population of adherent cells (this incubation can also apply to MAPC isolation from any subject).

One embodiment provides a non-human animal, including, but not limited to, swine, containing exogenous sMAPCs. Such an animal can be used in the preclinical investigation of treatments for human disease, such as cardiovascular disease.

Another embodiment provides for the use of sMAPCs or progeny differentiated therefrom in medical therapy. In one embodiment, the medical therapy is the treatment of a cardiac, renal, hepatic, pancreatic or metabolic disease. Another embodiment provides for the use of sMAPCs or progeny differentiated therefrom to prepare a medicament useful for treating a cardiac, renal, hepatic, pancreatic or metabolic disease. In one embodiment, the medicament includes a carrier, including a pharmaceutically acceptable carrier.

Other aspects of the invention are described in or are obvious from the following disclosure, and are within the ambit of the invention.

BRIEF DESCRIPTION OF THE FIGURES

FIG. 5 depicts in vitro differentiation of sMAPCS to phenotypic smooth muscle-like cells. sMAPCs (about 60 PDs and about 100 PDs) were plated at about 2,000 cells/cm$^2$ in FN-coated wells in MAPC basal medium with 10 ng/ml PDGF and 5 ng/ml TGF-β for 12 days. (a) Cultures were fixed with −20° C. methanol on day 12 and double stained with (a) anti-caldesmin labeled with Cy3, (b) anti-SM22 labeled with Cy2, (c) Overlay of (a) and (b), (d) anti-SM-a-actin labeled with Cy3, (e) anti-Calponin labeled with Cy2, (f) Overlay of (d) and (e), nuclei were stained by DAPI. (g) Smooth muscle differentiation cultures were evaluated by RT-PCR for Myocardin, Calponin, SM-a-actin, GATA6 and smoothelin. Magnification: a-d, ×40. (Representative example of 12 experiments from 3 donors.)

FIG. 12 depicts MAPC expression of cardiomyocyte specific transcripts. A: Q-RT-PCR on rat MAPC (rMAPC) differentiation at d6: lane 1: NTC, lane 2 undiff MAPC, lane 3 and 4: 2.5 and 10 ng/ml activin+5AZA; lane 6 and 7: 2.5 and 10 ng/ml activin, no 5AZA. B: sMAPC treated with 10 ng/ml Dkk-1 and 0.75% DMSO (days 1-2), 10 ng/ml DKK1, BMP2 and FGF8, 100 ng/ml FGF4 100, ascorbic acid (days 3-21). RT-PCR was performed on d23.

DETAILED DESCRIPTION OF THE INVENTION

Figure 1A:
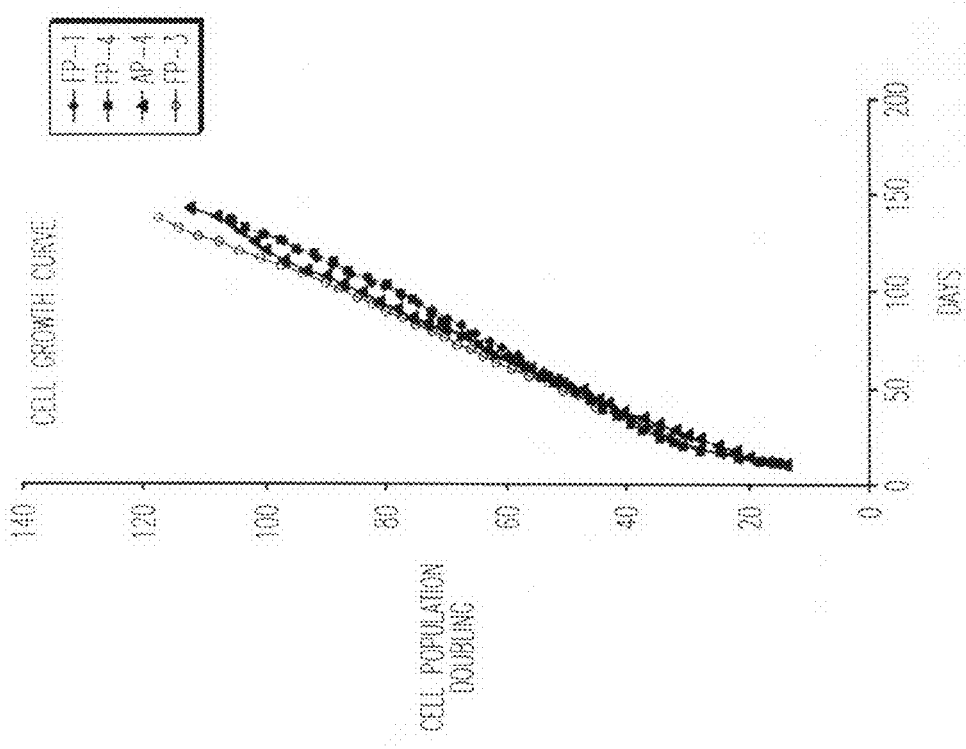
FIG. 1 depicts sMAPCs. Swine BMMNCs were plated with EGF, PDGF-BB in FN-coated flasks. After 3-4 weeks, appeared sMAPCs were plated at 1 cell/well in FN-coated 48 well plates in the same medium and expanded at 500 cells/cm$^2$. (a) Cells were enumerated at each passage under a haemocytometer (three fetal and 1 adult cell lines are listed). (b) sMAPC single cell derived colony, replated and expanded again at 500 cells/cm$^2$. (c) sMAPC morphology at 81 cell population doublings.

Introduction to Multipotent Adult Progenitor Cells (MAPCs)

MAPC is an acronym for an adult stem cell (non-ES, non-EG, non-germ) that has the capacity to differentiate into cell types of all three primitive germ layers (Verfaillie, C. M. 2002; Jahagirdar, B. N. et al. 2001). Genes that characterize the undifferentiated state of ES cells were also found in these adult cells (Oct 3/4, rex-1, rox-1, sox-2). These cells are capable of indefinite culture without loss of their differentiation potential and show efficient, long term, engraftment and differentiation along multiple developmental lineages in NOD-SCID mice without evidence of teratoma formation (Reyes, M. and C. M. Verfaillie 2001).

The biological potency of these cells has been demonstrated in various animal models, including mouse and rat and xenogenic engraftment of human stem cells in rat or NOD/SCID mice (Reyes, M. and C. M. Verfaillie 2001; Jiang, Y. et al. 2002). In an elegant demonstration of the clonal potency of this cell population, single genetically marked MAPCs were injected into mouse blastocysts, the blastocysts were implanted, and embryos developed (Jiang, Y., et al. 2002). Post-natal analysis in highly chimeric animals demonstrated reconstitution of all tissues and organs, including liver. Dual staining experiments demonstrated that the gene marked cells contributed to a significant percentage of apparently functional cardiomyocytes in these animals. These animals did not show any heart abnormalities or irregularities in either the embryologic or adult state. Furthermore, no abnormalities or organ dysfunction were observed in any of the animals.

MAPCs are further characterized as cells that constitutively express Oct-4 and high levels of telomerase (Jiang, Y. et al., 2002). MAPCs derived from human, mouse, rat or other mammals appear to be the only normal, non-malignant, somatic cell (i.e., non-germ cell) known to date to express very high levels of telomerase even in late passage cells. The telomeres are extended in MAPCs and the cells are karyotypically normal. They have utility in the repopulation of organs, either in a self-renewing state or in a differentiated state compatible with the organ of interest. They have the capacity to replace cell types that could have been damaged, died, or otherwise might have an abnormal function because of genetic or acquired disease.

Human MAPCs are described in U.S. patent application Ser. No. 10/048,757 (PCT/US00/21387 (published as WO 01/11011)) and Ser. No. 10/467,963 (PCT/US02/04652 (published as WO 02/064748)), the contents of which are incorporated herein by reference for their description of MAPCs. MAPCs have been identified in other mammals. Murine MAPCs, for example, are also described in PCT/US00/21387 (published as WO 01/11011) and PCT/US02/04652 (published as WO 02/064748). Rat MAPCs are also described in WO 02/064748. These methods, along with the characterization of MAPCs disclosed therein, are incorporated herein by reference.

MAPCs can be isolated from multiple sources, including bone marrow, muscle, brain, liver, spinal cord, blood or skin. For example, MAPCs can be derived from bone marrow aspirates, which can be obtained by standard means known to those of skill in the art (see, for example, Muschler, G. F. et al. 1997; Batinic, D. et al. 1990). It is therefore now possible for one of skill in the art to obtain bone marrow aspirates, brain or liver biopsies, and other organs, and isolate the cells using positive or negative selection techniques known to those of skill in the art, relying upon the genes that are expressed (or not expressed) in these cells (e.g., by functional or morphological assays).

Swine MAPCs of the Invention

Specifically described herein is the isolation and characterization of fetal and adult sMAPCs from swine bone marrow. Swine MAPCs (sMAPCs) may proliferate for more than 100 population doublings without cytogenetic abnormalities, and are CD45 and major histocompatibility complex class II negative and express Oct 3A. sMAPCs are also shown to be multipotent. Cells, methods and compositions are provided for therapeutic (clinical and preclinical), diagnostic and research uses of sMAPCs.

Therapeutic applications include the transplantation of sMAPCs to injured and diseased tissue. In some such embodiments, the cells differentiate and provide replacements for cells lost to injury. For example, the sMAPCs occupy the region of the injury or disease to take over the function of lost or damaged cells or are used to secrete proteins or other factors needed in the damaged or diseased tissue. Differentiation can occur in vivo, ex vivo or in vitro. In some embodiments, cells from a particular host are used to transplant into a different region of the host. The present invention also provides methods for allotransplantation (e.g., between a donor sibling and a recipient sibling or between an immunologically matched or partially matched donor and recipient, etc.). The present invention further provides methods for xenotransplantation (e.g., transplantation of cells from a different species).

Large animal models are also provided for the preclinical investigation and analysis of MAPC based therapies. For example, the isolation of swine MAPCs provides for a large animal model for preclinical investigation for safety and effectiveness of MAPCs in disease models, including, but not limited to, cardiovascular diseases.

Definitions

As used herein, the terms below are defined by the following meanings:

As used herein, "sMAPC" is an acronym for a swine multipotent adult "progenitor cell." It refers to a multipotent non-embryonic stem (non-ES), non-germ, non-embryonic germ (non-EG) cell that is capable of self renewal and that can give rise to cell types of more than one embryonic lineage. For example, sMAPCs can give rise to cells of at least two or all three primitive germ layers (endoderm, mesoderm and ectoderm) upon differentiation. Like embryonic stem cells, sMAPCs can express Oct 3A and telomerase. Telomerase or Oct 3/4 have been recognized as genes that characterize the undifferentiated state. Telomerase is needed for self renewal without replicative senescence. sMAPCs are negative for cell surface expression of CD44, CD45 and MHC class I and II under the specific assay conditions shown in Example 1. sMAPC can be derived from any tissue, including, but are not limited to bone marrow, muscle, brain, blood, umbilical cord, including cord blood, or placenta. The term "adult," with respect to MAPC is non-restrictive. It refers to a non-embryonic somatic cell.

MAPCs, such as sMAPCs, injected into a mammal can migrate to and assimilate within multiple organs. MAPCs are also self-renewing. As such, they have utility in the repopulation of organs, either in a self-renewing state or in a differentiated state compatible with the organ of interest. They have the capacity to replace cell types that have been damaged (due to disease or injury), died, or otherwise have an abnormal function because of genetic or acquired disease. Or, as discussed below, they may contribute to the preservation of healthy cells or production of new cells in a tissue.

"Multipotent," with respect to MAPC or sMAPCs, refers to the ability to give rise to cell types of more than one embryonic lineage. sMAPCs can form cell lineages of all three primitive germ layers (i.e., endoderm, mesoderm and ectoderm).

"Expansion" refers to the propagation of cells without differentiation.

"Progenitor cells" are cells produced during differentiation of a stem cell that have some, but not all, of the characteristics of their terminally-differentiated progeny. Defined progenitor cells, such as "liver progenitor cells," are committed to a lineage, but not to a specific or terminally-differentiated cell type. The term "progenitor" as used in the acronym "MAPC" or "sMAPC" does not limit these cells to a particular lineage.

"Self-renewal" refers to the ability to produce replicate daughter cells having differentiation potential that is identical to those from which they arose. A similar term used in this context is "proliferation."

"Engraft" or "engraftment" refers to the process of cellular contact and incorporation into an existing tissue or site of interest. In one embodiment, greater than about 5%, greater than about 10%, greater than about 15%, greater than about 20%, greater than about 25%, greater than about 30%, greater than about 35%, greater than about 40%, greater than about 45%, greater than about 50%, greater than about 55%, greater than about 60%, greater than about 65%, greater than about 70%, greater than about 75%, greater than about 80%, greater than about 85%, greater than about 90%, greater than about 95% or about 100% of administered sMAPCs or progeny derived therefrom engraft in tissues of the subject. In another embodiment, less than about 5%, less than about 2.5%, less than about 2%, less than about 1.5% or less than about 1% of administered sMAPCs or progeny derived therefrom engraft in tissues of the subject.

Persistence refers to the ability of cells to resist rejection and remain or increase in number over time (e.g., days, weeks, months, years) in vivo. Thus, by persisting, sMAPCs or progeny differentiated therefrom can populate tissues or remain in vivo.

"Immunologic tolerance" refers to the survival (in amount and/or length of time) of foreign (e.g., allogeneic or xenogeneic) tissues, organs or cells in recipient subjects. This survival is often a result of the inhibition of a graft recipient's ability to mount an immune response that would otherwise occur in response to the introduction of foreign cells. Immune tolerance can encompass durable immunosuppression of days, weeks, months or years. Included in the definition of immunologic tolerance is NK-mediated immunologic tolerance. This term also encompasses instances where the graft is tolerant of the host.

The term "isolated" refers to a cell or cells which are not associated with one or more cells or one or more cellular components that are associated with the cell or cells in vivo.

An "enriched population" means a relative increase in numbers of, for example, sMAPC relative to one or more non-sMAPC cell types in vivo or in cultures, including primary cultures, of different levels of purity.

"Cytokines" refer to cellular factors that induce or enhance cellular movement, such as homing of sMAPCs or other stem cells, progenitor cells or differentiated cells. Cytokines may also stimulate such cells to divide.

"Differentiation factors" refer to cellular factors, preferably growth factors or angiogenic factors that induce lineage commitment.

A "subject" is a vertebrate, preferably a mammal, more preferably a human. Mammals include, but are not limited to, humans, farm animals, sport animals and pets. Included in the terms animals or pets are, but not limited to, dogs, cats, horses, rabbits, mice, rats, sheep, goats, cows and birds.

As used herein, "treat," "treating" or "treatment" includes treating, reversing, preventing, ameliorating, or inhibiting an injury or disease-related condition or a symptom of an injury or disease-related condition.

An "effective amount" generally means an amount which provides the desired effect. For example, an effective dose is an amount sufficient to effect a beneficial or desired result, including a clinical result. The dose could be administered in one or more administrations and can include any preselected amount of cells. The precise determination of what would be considered an effective dose may be based on factors individual to each subject, including size, age, injury or disease being treated and amount of time since the injury occurred or the disease began. One skilled in the art, particularly a physician, would be able to determine the number of cells that would constitute an effective dose. Doses can vary depending on the mode of administration, e.g., local or systemic; free or encapsulated. The effect can be engraftment or other clinical endpoints, such as reversal or treatment of liver failure. Other effects can include providing mature cells, recruiting endogenous cells, effecting angiogenesis, and/or providing pancreatic progenitors.

"Co-administer" can include simultaneous and/or sequential administration of two or more agents.

Administered sMAPCs or progeny differentiated therefrom may contribute to the generation or function of tissues by differentiating into various cells in vivo. Alternatively, or in addition, administered cells may contribute to the generation of tissues by secreting cellular factors that aid in homing and recruitment of endogenous MAPCs or other stem cells, or other more differentiated cells. Alternatively, or in addition, sMAPCs or progeny differentiated therefrom may secrete factors that act on endogenous stem or progenitor cells causing them to differentiate. Further, sMAPCs or progeny differentiated therefrom may secrete factors that act on stem, progenitor or differentiated cells, causing them to divide. Thus, sMAPCs or progeny differentiated therefrom may provide benefit through trophic influences. Examples of trophic influences include, but are not limited to, improving cell survival and homing of cells to desired sites. Additionally, sMAPCs or progeny differentiated therefrom may provide for angiogenesis or reduce or prevent apoptosis. Therapeutic benefit may be achieved by a combination of the above pathways.

The terms "comprises", "comprising", and the like can have the meaning ascribed to them in U.S. Patent Law and can mean "includes", "including" and the like. As used herein, "including" or "includes" or the like means including, without limitation.

Isolation and Growth of sMAPCs

Described herein are MAPCs isolated from swine (sMAPC), specifically from swine bone marrow. sMAPCs were isolated from swine bone marrow (BM) obtained from fetal pigs (gestational age about 10 weeks) and 20 postnatal pigs (age about 40 days). sMAPC can be derived from any tissue. These include, but are not limited to bone marrow, muscle, brain, umbilical cord, including cord blood, or placenta. Additionally, positive or negative selection or a combination of positive and negative selection may also be used to isolate sMAPCs. For example, positive selection isolates cells by using a combination of cell-specific markers known in the art and negative selection isolates cells by using any of the various monoclonal or polyclonal antibodies known in the art (see, for example, Leukocyte Typing V, Schlossman, et al., Eds. (1995) Oxford University Press) and are commercially available from a number of sources.

Techniques for mammalian cell separation from a mixture of cell populations have also been described by Schwartz, et al., in U.S. Pat. No. 5,759,793 (magnetic separation), Basch, et al. (1983) (immunoaffinity chromatography), and Wysocki and Sato (1978) (fluorescence-activated cell sorting).

Methods of MAPC isolation for humans and mouse are described in U.S. patent application Ser. No. 10/048,757 (PCT/US00/21387 (published as WO 01/11011)) and for rat in U.S. patent application Ser. No. 10/467,963 (PCT/US02/04652 (published as WO 02/064748)), and these methods, along with the characterization of MAPCs disclosed therein, are incorporated herein by reference.

Initially, sMAPCs are maintained and allowed to expand in culture medium that is established in the art and commercially available from the American Type Culture Collection (ATCC). Such media include, but are not limited to, Dulbecco's Modified Eagle's Medium® (DMEM), DMEM F12 medium®, Eagle's Minimum Essential Medium®, F-12K medium®, Iscove's Modified Dulbecco's Medium®, RPMI-1640 medium®.

sMAPCs can be maintained and expanded on fibronectin-coated plates in medium containing about 40-60%, including 60%, DMEM-LG and about 40-60%, including 40%, MCDB-201 supplemented with 1× ITS (or 10-50 μg/ml insulin, 0-10 μg/ml transferrin and/or 2-10 ng/ml selenium), 0.5× LA-BSA (or 0.1 to 5 μg/ml BSA and/or 2-10 μg/ml linoleic acid), 0.1 mM ascorbic acid 2-phosphate, about 50 to about 100 U penicillin and about 500 to about 1,000 U streptomycin, and 5 to 15 ng/ml each hu-PDGF-BB and hu-EGF. The medium can also contain 0-2% fetal calf serum, 0.005-0.15 μM dexamethasone.

Once established in culture, cells can be frozen and stored as frozen stocks using DMEM with about 40% FCS and about 10% DMSO. Other methods for preparing frozen stocks for cultured cells are also available to those of skill in the art.

Also contemplated is supplementation of cell culture medium with mammalian sera. Sera often contain cellular factors and components that are necessary for viability and expansion. Examples of sera include fetal bovine serum (FBS), bovine serum (BS), calf serum (CS), fetal calf serum (FCS), newborn calf serum (NCS), goat serum (GS), horse serum (HS), human serum, chicken serum, porcine serum, sheep serum, rabbit serum, serum replacements, and bovine embryonic fluid. It is understood that sera can be heat-inactivated at 55-65° C. if deemed necessary to inactivate components of the complement cascade.

Additional supplements can also be used advantageously to supply the cells with the necessary trace elements for optimal growth and expansion. Such supplements include insulin, transferrin, sodium selenium and combinations thereof. These components can be included in a salt solution such as Hanks' Balanced Salt Solution® (HBSS), Earle's Salt Solution®, antioxidant supplements, MCDB-201® supplements, phosphate buffered saline (PBS), ascorbic acid and ascorbic acid-2-phosphate, as well as additional amino acids. Many cell culture media already contain amino acids, however some require supplementation prior to culturing cells. Such amino acids include, but are not limited to, L-alanine, L-arginine, L-aspartic acid, L-asparagine, L-cysteine, L-cystine, L-glutamic acid, L-glutamine, L-glycine, L-histidine, L-isoleucine, L-leucine, L-lysine, L-methionine, L-phenylalanine, L-proline, L-serine, L-threonine, L-tryptophan, L-tyrosine, and L-valine. It is well within the skill of one in the art to determine the proper concentrations of these supplements.

Antibiotics are also typically used in cell culture to mitigate bacterial, mycoplasmal, and fungal contamination. Typically, antibiotics or anti-mycotic compounds used are mixtures of penicillin/streptomycin, but can also include, but are not limited to, amphotericin (Fungizone®), ampicillin, gentamicin, bleomycin, hygromycin, kanamycin, mitomycin, mycophenolic acid, nalidixic acid, neomycin, nystatin, paromomycin, polymyxin, puromycin, rifampicin, spectinomycin, tetracycline, tylosin, and zeocin.

Hormones can also be advantageously used in cell culture and include, but are not limited to, D-aldosterone, diethylstilbestrol (DES), dexamethasone, β-estradiol, hydrocortisone, insulin, prolactin, progesterone, somatostatin/human growth hormone (HGH), thyrotropin, thyroxine, and L-thyronine.

Lipids and lipid carriers can also be used to supplement cell culture media, depending on the type of cell and the fate of the differentiated cell. Such lipids and carriers can include, but are not limited to cyclodextrin (α, β, γ), cholesterol, linoleic acid conjugated to albumin, linoleic acid and oleic acid conjugated to albumin, unconjugated linoleic acid, linoleic-oleic-arachidonic acid conjugated to albumin, oleic acid unconjugated and conjugated to albumin, among others.

Also contemplated is the use of feeder cell layers. Feeder cells are used to support the growth of fastidious cultured cells, including stem cells. Feeder cells are normal cells that have been inactivated by γ-irradiation. In culture, the feeder layer serves as a basal layer for other cells and supplies cellular factors without further growth or division of their own (Lim, J. W. and Bodnar, A. 2002). Examples of feeder layer cells are typically human diploid lung cells, mouse embryonic fibroblasts, Swiss mouse embryonic fibroblasts, but can be any post-mitotic cell that is capable of supplying cellular components and factors that are advantageous in allowing optimal growth, viability, and expansion of stem cells. In many cases, feeder cell layers are not necessary to keep the stem cells in an undifferentiated, proliferative state, as leukemia inhibitory factor (LIF) has anti-differentiation properties. Often, supplementation of a defined concentration of LIF is all that is necessary to maintain stem cells in an undifferentiated state.

Cells in culture can be maintained either in suspension or attached to a solid support, such as extracellular matrix components and synthetic or biopolymers. Stem cells often require additional factors that encourage their attachment to a solid support, such as type I, type II, and type IV collagen, concanavalin A, chondroitin sulfate, fibronectin, "superfibronectin" and fibronectin-like polymers, gelatin, laminin, poly-D and poly-L-lysine, thrombospondin, and vitronectin.

The maintenance conditions of stem cells can also contain cellular factors that allow stem cells, such as sMAPCs, to remain in an undifferentiated form. Specifically, these cellular factors or components allow the stem cells to remain multipotent, constitutively express Oct 4 (oct3A), maintain high levels of telomerase, and remain negative for CD44, CD45, HLA (i.e., MHC class I and MHC class II) expression. It is advantageous under conditions where the cell must remain in an undifferentiated state of self-renewal for the medium to contain epidermal growth factor (EGF), platelet derived growth factor (PDGF), leukemia inhibitory factor (LIF; in certain species), or combinations thereof. It is apparent to those skilled in the art that supplements that allow the cell to self-renew, but not differentiate, should be removed from the culture medium prior to differentiation.

Stem cell lines and other fastidious cells often benefit from co-culturing with another cell type. Such co-culturing methods arise from the observation that certain cells can supply yet-unidentified cellular factors that allow the stem cell to differentiate into a specific lineage or cell type. These cellular factors can also induce expression of cell-surface receptors, some of which can be readily identified by monoclonal antibodies. Generally, cells for co-culturing are selected based on the type of lineage one skilled in the art wishes to induce, and it is within the capabilities of the skilled artisan to select the appropriate cells for co-culture.

Methods of identifying and subsequently separating differentiated cells from their undifferentiated counterparts can be carried out by methods well known in the art. Cells that have been induced to differentiate can be identified by selectively culturing cells under conditions whereby differentiated cells outnumber undifferentiated cells. Similarly, differentiated cells can be identified by morphological changes and characteristics that are not present on their undifferentiated counterparts, such as cell size, the number of cellular processes (i.e. formation of dendrites and/or branches), and the complexity of intracellular organelle distribution. Also contemplated are methods of identifying differentiated cells by their expression of specific cell-surface markers such as cellular receptors and transmembrane proteins. Monoclonal antibodies against these cell-surface markers can be used to identify differentiated cells. Detection of these cells can be achieved through fluorescence activated cell sorting (FACS), and enzyme-linked immunosorbent assay (ELISA). From the standpoint of transcriptional up-regulation of specific genes, differentiated cells often display levels of gene expression that are different from undifferentiated cells. Reverse-transcription polymerase chain reaction (RT-PCR) can also be used to monitor changes in gene expression in response to differentiation. In addition, whole genome analysis using microarray technology can be used to identify differentiated cells.

Accordingly, once differentiated cells are identified, they can be separated from their undifferentiated counterparts, if necessary. The methods of identification detailed above also provide methods of separation, such as FACS, preferential cell culture methods, ELISA, magnetic beads, and combinations thereof. A preferred embodiment of the invention envisions the use of FACS to identify and separate cells based on cell-surface antigen expression.

Additional Culture Methods

The density at which MAPCs are cultured can vary from about 100 cells/cm$^2$ or about 150 cells/cm$^2$ to about 10,000 cells/cm$^2$, including about 200 cells/cm$^2$ to about 1500 cells/cm$^2$ to about 2,000 cells/cm$^2$. The density can vary between species. Additionally, optimal density can vary depending on culture conditions and source of cells. It is within the skill of the ordinary artisan to determine the optimal density for a given set of culture conditions and cells.

Also, effective atmospheric oxygen concentrations of less than about 10%, including about 3-5%, can be used at any time during the isolation, growth and differentiation of MAPCs in culture.

Isolating and culturing MAPCs at 5% $O_2$ was shown to result in fewer cytogenetic abnormalities. Additionally, it resulted in a slight change in the phenotype of MAPCs. When rodent MAPCs are isolated and maintained at 5% $O_2$, Oct 4 transcript levels approach those of embryonic stem (ES) cells (50-80%), and >90% of cells express nuclear Oct 4 protein by immunohistochemistry. 5%-$O_2$ derived rodent MAPCs also express Rex1 at levels approaching that of ES cells, suggesting that Oct 4 is functional within these cells. However, Nanog mRNA remains almost undetectable. Low-$O_2$ derived mouse MAPCs are Sca1, Thy1, CD34, CD31, MHC-class I and II, CD44 negative, but cKit positive. Although mouse MAPCs express Oct 4 mRNA at levels similar to ES cells, they do not form embryoid bodies or teratomas (5×10$^6$ MAPCs grafted under the skin of 5 nude mice).

Inducing MAPCs to Differentiate

Using appropriate growth factors, chemokines and/or cytokines, MAPCs can be induced to differentiate to form a number of cell lineages, including, for example, cells of mesodermal, neuroectodermal and endodermal origin. For example, as demonstrated herein below, sMAPCs were shown to have the capacity to differentiate to cartilage cells, endothelial cells, neural cells, hepatocytes, cardiomyocytes and smooth muscle cells. Differentiation conditions were similar to those described for human and rodent MAPCs (PCT/US0021387 (published as WO 01/11011) and PCT/US02/04652 (published as WO 02/064748), which are incorporated herein by reference.

Administration of sMAPCs

For the purposes described herein, either autologous, allogeneic or xenogeneic sMAPCs can be administered to a subject, either in differentiated or undifferentiated form, genetically altered or unaltered, by direct injection to a tissue site, systemically, on or around the surface of an acceptable matrix, encapsulated or in combination with a pharmaceutically acceptable carrier.

sMAPCs can be administered to a subject by a variety of methods known in the art. sMAPCs can be administered to a subject by localized or systemic injection. sMAPCs can also be administered by surgical intramyocardial injection, transendocardial injection, intracoronary injection, transvascular injection, intramuscular injection, and intravenous injection. sMAPCs may be administered within or in proximity to the site requiring new cells, mass, or enhanced function alternatively they can be administered at a remote location.

In one embodiment, a cell suspension is drawn up into a syringe and administered to a subject. Multiple injections may be made using this procedure. The use of such cellular suspension procedures provides many advantages. For example, these methods direct cells to any predetermined site and are relatively non-traumatic.

Typically, the number of cells transplanted into a subject will be a "therapeutically effective amount." As used herein, a "therapeutically effective amount" refers to the number of transplanted cells that are required to effect treatment of the particular injury, or disease for which treatment is sought. For example, where the treatment is for tissue injury, transplantation of a therapeutically effective amount of cells will typically produce a reduction in the amount and/or severity of the symptoms associated with the injury. Persons of skill in the art will understand how to determine proper cell dosages.

As desired, sMAPCs and their progeny can be induced to proliferate and/or differentiate in vivo by administering to the host, any growth factor(s), cytokine(s) or pharmaceutical composition(s) that will induce proliferation and differentiation of the cells. These growth factor(s), cytokine(s) or pharmaceutical composition(s) include any growth factor, cytokine or pharmaceutical composition known in the art, including the growth factors and cytokines described herein for in vitro proliferation and differentiation.

sMAPCs, as well as damaged tissue, including damaged cardiac tissue, secrete cytokines that have beneficial effects, including recruitment of reparative cells (e.g., MAPCs, hematopoietic, mesenchymal cells) to the damaged tissue by "homing" mechanisms and modulation of inflammatory processes. For example, "homing" of stem cells to injured or diseased tissues concentrates the implanted cells in an environment favorable to their growth and function. Pretreatment of a patient with cytokine(s) to promote homing is another alternative contemplated in the methods of the present invention. Furthermore, differentiation of sMAPCs to a desired phenotype can be enhanced when differentiation factors are employed. Thus, the present invention includes the administration of sMAPCs to a subject in need thereof in the presence of cytokines, growth factors and/or differentiation factors (endogenous cytokines, growth factors and/or differentiation factors or cytokines, growth factors and/or differentiated factors administered to the subject prior to, after, and/or in conjunction with sMAPC administration) to enhance homing of sMAPCs to damaged or abnormal tissues or organs, and to enhance differentiation of sMAPCs into cells of a desired lineage.

Cytokines include, but are not limited to, stromal cell derived factor-1 (SDF-1), stem cell factor (SCF), angiopoietin-1, placenta-derived growth factor (PlGF) and granulocyte-colony stimulating factor (G-CSF). Cytokines also include any which promote the expression of endothelial adhesion molecules, such as ICAMs, VCAMs, and others, which facilitate the homing process.

Differentiation of sMAPCs to a desired phenotype can be enhanced when differentiation factors are employed. For example, differentiation factors promoting muscle formation include, but are not limited to, vascular endothelial growth factor (VEGF), fibroblast growth factors (e.g., FGF4, FGF8, bFGF) Wnt11, DKK1, ascorbic acid, isoproterenol and endothelin.

The viability of newly forming tissues can be enhanced by angiogenesis. Differentiation factors promoting angiogenesis include, but are not limited to, VEGF, aFGF, angiogenin, angiotensin-1 and -2, betacellulin, bFGF, Factor X and Xa, HB-EGF, PDGF, angiomodulin, angiotropin, angiopoetin-1, prostaglandin E1 and E2, steroids, heparin, 1-butyryl-glycerol and nicotinic amide.

Factors that decrease apoptosis can also promote the formation of new tissue. Factors that decrease apoptosis include, but are not limited to, β-blockers, angiotensin-converting enzyme inhibitors (ACE inhibitors), carvedilol, angiotensin II type I receptor antagonists, caspase inhibitors, cariporide, and eniporide.

Exogenous factors (e.g., cytokines, growth factors, differentiation factors and anti-apoptosis factors) can be administered prior to, after or concomitantly with sMAPCs. For example, a form of concomitant administration would comprise combining a factor of interest in the sMAPC suspension media prior to administration. Doses for administrations are variable, may include an initial administration followed by subsequent administrations; but nonetheless, can be ascertained by the skilled artisan, from this disclosure, the documents cited herein, and the knowledge in the art.

A method to potentially increase cell survival is to incorporate sMAPCs into a suitable matrix implant, including, but not limited to, a biopolymer or synthetic polymer or polymer matrix (so as to encapsulate the cells prior to introduction into the body of the subject, such as within a polymer capsule). Depending on the subject's condition, the site of injection might prove inhospitable for cell seeding and growth because of scarring or other impediments. Examples of biopolymer include, but are not limited to, cells mixed with biopolymers such as fibronectin, fibrin, fibrinogen, thrombin, collagen, and proteoglycans, which may be chemically modified or shaped. This could be constructed with or without cytokines, differentiation or additional genetic material. Additionally, these could be in suspension, but residence time at sites subjected to flow would be nominal.

Another alternative is a three-dimension gel with cells entrapped within the interstices of the cell/biopolymer admixture. Again differentiation factors or cytokines could be included within the gel. These could be delivered by injection by various routes.

An issue concerning the therapeutic use of stem cells is the quantity of cells necessary to achieve an optimal effect. The quantity of cells to be administered will vary for the subject being treated. In one embodiment, about $10^4$ to about $10^8$, more preferably about $10^5$ to about $10^7$, and most preferably about $3 \times 10^7$ cells and optionally, 50 to 500 µg/kg per day of a cytokine can be administered to a human subject. However, the precise determination of what would be considered an effective dose may be based on factors individual to each patient, including their size, age, size of the infarct or other organ damage, and amount of time since the damage or disease began. Therefore, dosages can be readily ascertained by those skilled in the art from this disclosure and the knowledge in the art.

Another issue regarding the use of stem cells is the purity of the population. Bone marrow cells, for example, comprise mixed populations of cells, which can be purified to a degree sufficient to produce a desired effect. Those skilled in the art can readily determine the percentage of sMAPCs in a population of cells using various well-known methods, such as fluorescence activated cell sorting (FACS). Preferable ranges of purity in populations comprising sMAPCs are 50-55%, 55-60%, and 65-70%. More preferably the purity is 70-75%, 75-80%, 80-85%; and most preferably the purity is 85-90%, 90-95%, and 95-100%. Preferred ranges of purity in populations comprising sMAPCs also include 1-5%, 5-10%, 10-15%, 15-20%, 20-25%, 25-30%, 30-35%, 35-40%, 40-45% and 45-50%. Purity of sMAPCs can be determined according to the cell surface marker profile within a population. For example, a population comprising cells which are at least 50% $CD44^-$, $CD45^-$ and $HLA^-$, or any other disclosed marker, contain sMAPCs of sufficient purity. Dosages can be readily adjusted by those skilled in the art (e.g., a decrease in purity may require an increase in dosage).

The skilled artisan can readily determine the amount of cells and optional additives, vehicles, and/or carrier in compositions to be administered in methods of the invention. Typically, any additives (in addition to the active stem cell(s) and/or cytokine(s)) are present in an amount of 0.001 to 50 wt % solution, and the active ingredient is present in the order of micrograms to milligrams, such as about 0.0001 to about 5 wt %, preferably about 0.0001 to about 1 wt %, most preferably about 0.0001 to about 0.05 wt % or about 0.001 to about 20 wt %, preferably about 0.01 to about 10 wt %, and most preferably about 0.05 to about 5 wt %. Of course, for any composition to be administered to an animal or human, and for any particular method of administration, it is preferred to determine therefore toxicity, such as by determining the lethal dose (LD) and $LD_{50}$ in a suitable animal model, e.g., rodent, such as mouse, and the dosage of the composition(s), concentration of components therein and timing of administering the composition(s), which elicit a suitable response. Such determinations do not require undue experimentation from the knowledge of the skilled artisan, this disclosure and the documents cited herein. Furthermore, the timing of sequential administrations can be ascertained without undue experimentation.

When administering a therapeutic composition of the present invention, it will generally be formulated in a unit dosage injectable form (solution, suspension, emulsion). The pharmaceutical formulations suitable for injection include sterile aqueous solutions and dispersions. The carrier can be a solvent or dispersing medium containing, for example, water, saline, phosphate buffered saline, polyol (for example, glycerol, propylene glycol, liquid polyethylene glycol, and the like) and suitable mixtures thereof.

Additionally, various additives which enhance the stability, sterility, and isotonicity of the compositions, including antimicrobial preservatives, antioxidants, chelating agents, and buffers, can be added. Prevention of the action of microorganisms can be ensured by various antibacterial and antifungal agents, for example, parabens, chlorobutanol, phenol, sorbic acid, and the like. In many cases, it will be desirable to include isotonic agents, for example, sugars, sodium chloride, and the like. Prolonged absorption of the injectable pharmaceutical form can be brought about by the use of agents delaying absorption, for example, aluminum monostearate and gelatin. According to the present invention, however, any vehicle, diluent, or additive used would have to be compatible with the cells.

Sterile injectable solutions can be prepared by incorporating the cells utilized in practicing the present invention in the required amount of the appropriate solvent with various amounts of the other ingredients, as desired.

In one embodiment, sMAPCs can be administered initially, and thereafter maintained by further administration of sMAPCs. For instance, sMAPCs can be administered by one method of injection, and thereafter further administered by a different or the same type of method. For example, sMAPCs can be administered by surgical myocardial injection to bring cardiovascular function to a suitable level. The patient's levels can then be maintained, for example, by intravenous injection, although other forms of administration, dependent upon the patient's condition, can be used.

It is noted that human subjects are treated generally longer than experimental animals, such that treatment has a length proportional to the length of the disease process and effectiveness. Thus, one of skill in the art can scale up from animal experiments to humans, by techniques from this disclosure and documents cited herein and the knowledge in the art, without undue experimentation.

Examples of compositions comprising sMAPCs include liquid preparations for administration, including suspensions; and, preparations for intramuscular or intravenous administration (e.g., injectable administration), such as sterile suspensions or emulsions. Such compositions may be in admixture with a suitable carrier, diluent, or excipient such as sterile water, physiological saline, glucose, dextrose, or the like. The compositions can also be lyophilized. The compositions can contain auxiliary substances such as wetting or emulsifying agents, pH buffering agents, gelling or viscosity enhancing additives, preservatives, flavoring agents, colors, and the like, depending upon the route of administration and the preparation desired. Standard texts, such as "REMINGTON'S PHARMACEUTICAL SCIENCE", 17th edition, 1985, incorporated herein by reference, may be consulted to prepare suitable preparations, without undue experimentation.

Compositions of the invention are conveniently provided as liquid preparations, e.g., isotonic aqueous solutions, suspensions, emulsions or viscous compositions, which may be buffered to a selected pH. Liquid preparations are normally easier to prepare than gels, other viscous compositions, and solid compositions. Additionally, liquid compositions are somewhat more convenient to administer, especially by injection. Viscous compositions, on the other hand, can be formulated within the appropriate viscosity range to provide longer contact periods with specific tissues.

The choice of suitable carriers and other additives will depend on the exact route of administration and the nature of the particular dosage form, e.g., liquid dosage form (e.g., whether the composition is to be formulated into a solution, a suspension, gel or another liquid form, such as a time release form or liquid-filled form).

Solutions, suspensions and gels normally contain a major amount of water (preferably purified, sterilized water) in addition to the cells. Minor amounts of other ingredients such as pH adjusters (e.g., a base such as NaOH), emulsifiers or dispersing agents, buffering agents, preservatives, wetting agents and jelling agents (e.g., methylcellulose), may also be present. The compositions can be isotonic, i.e., they can have the same osmotic pressure as blood and lacrimal fluid.

The desired isotonicity of the compositions of this invention may be accomplished using sodium chloride, or other pharmaceutically acceptable agents such as dextrose, boric acid, sodium tartrate, propylene glycol or other inorganic or organic solutes. Sodium chloride is preferred particularly for buffers containing sodium ions.

Viscosity of the compositions, if desired, can be maintained at the selected level using a pharmaceutically acceptable thickening agent. Methylcellulose is preferred because it is readily and economically available and is easy to work with. Other suitable thickening agents include, for example, xanthan gum, carboxymethyl cellulose, hydroxypropyl cellulose, carbomer, and the like. The preferred concentration of the thickener will depend upon the agent selected. The point is to use an amount, which will achieve the selected viscosity. Viscous compositions are normally prepared from solutions by the addition of such thickening agents.

A pharmaceutically acceptable preservative or cell stabilizer can be employed to increase the life of the compositions. Preferably, if preservatives are necessary, it is well within the purview of the skilled artisan to select compositions that will not affect the viability or efficacy of the MAPCs as described in the present invention.

Those skilled in the art will recognize that the components of the compositions should be selected to be chemically inert. This will present no problem to those skilled in the chemical and pharmaceutical arts, or problems can be readily avoided by reference to standards texts or simple experiments.

Compositions can be administered in dosages and by techniques well known to those skilled in the medical and veterinary arts taking into consideration such factors as the age, sex, weight, and condition of the particular subject, and the composition form used for administration (e.g., solid vs. liquid). Dosages for humans or other mammals can be determined without undue experimentation by the skilled artisan, from this disclosure, the documents cited herein, and knowledge in the art.

Suitable regimes for initial administration and further doses for sequential administrations also are variable, may include an initial administration followed by subsequent administrations; but nonetheless, can be ascertained by the skill artisan, from this disclosure, the documents cited herein, and the knowledge in the art.

Approaches for Transplantation to Prevent Immune Rejection

In some embodiments, it may be desired that the sMAPCs (or progeny differentiated therefrom) be treated or otherwise altered prior to transplantation/administration in order to reduce the risk of stimulating a host immunological response against the transplanted cells. Any method known in the art to reduce the risk of stimulating a host immunological response may be employed. The following provides a few such examples.

1. Universal donor cells: sMAPCs can be manipulated to serve as universal donor cells. Although undifferentiated sMAPCs do not express MHC-I or -II antigens, some differentiated progeny may express one or both of these antigens. sMAPCs can be modified to serve as universal donor cells by eliminating MHC-I or MHC-II antigens, and potentially introducing the MHC-angtigens from the prospective recipient so that the cells do not become easy targets for NK-mediated killing, or become susceptible to unlimited viral replication or malignant transformation. Elimination of MHC-antigens can be accomplished, for example, by homologous recombination or by introduction of point-mutations in the promoter region or by introduction of a point mutation in the initial exon of the antigen to introduce a stop-codon, such as with chimeroplasts. Transfer of the host MHC-antigen(s) can be achieved by retroviral, lentiviral, adeno associated virus or other viral transduction or by transfection of the target cells with the MHC-antigen cDNAs.

2. Intrauterine transplant to circumvent immune recognition: sMAPCs can be used in an intrauterine transplantation setting to correct genetic abnormalities, or to introduce cells that will be tolerated by the host prior to immune system development.

3. Hematopoietic Chimerism and Tolerance Induction: Benefit would be achieved through use of a stem cell, capable of reconstituting the immune system that did not carry risk of graft-versus-host response. The graft-versus-host reaction is due to contaminating T cells inherent in the bone marrow graft. Although purification of hematopoietic stem cells from bone marrow is routine, their successful engraftment in the patient requires accompaniment by accessory T cells. Thus, a balance must be achieved between the beneficial engraftment value of T cells and the detrimental effect of graft-versus-host response.

MAPCs, including sMAPCs, and ES cells represent a stem cell population which can be delivered without risk of graft-versus-host reactivity, as they can be expanded free of hematopoietic cell types, including T cells. This greatly reduces clinical risk. The transient elimination of NK cell activity during the acute phase of cell delivery increases the frequency of primitive stem cell engraftment and hematopoietic reconstitution to a clinically useful threshold without risk of long term immunosuppression.

As MAPC or ES engraft and contribute to hematopoiesis, the newly formed T cells undergo thymic and peripheral self versus non-self education consistent with host T cells. Co-exposure of newly created naive T cells of donor and host origin results in reciprocal depletion of reactive cells; hence tolerance to T cells expressing allogeneic or xenogeneic antigens derived from a MAPC or ES donor can be achieved. A patient can thus be rendered tolerant to the cellular and molecular components of the MAPC or ES donor immune system, and would accept a cell, tissue or organ graft without rejection.

4. Encapsulation: In some embodiments, the sMAPCs are encapsulated (generally with a capsule that is permeable to nutrients and oxygen while allowing appropriate cellular products to be released into the blood stream or to adjacent tissues). The primary goal in encapsulation as a cell therapy is to protect allogeneic and xenogeneic cell transplants from destruction by the host immune response, thereby eliminating or reducing the need for immuno-suppressive drug therapy. Techniques for microencapsulation of cells are known to those of skill in the art (see, for example, Chang, P. et al. 1999; Matthew, H. W. et al. 1991; Yanagi, K. et al. 1989; Cai Z. H. et al. 1988; Chang, T. M. 1992). Materials for microencapsulation of cells include, for example, polymer capsules, alginate (e.g., alginate bead), alginate-poly-L-lysine-alginate microcapsules, polysaccharide hydrogels, chitosand, a layered matrix or alginate and polylysine, a photopolymerizable poly(ethylene glycol) (PEG) polymer (Novocell, Inc.), a polyanionic material termed Biodritin (U.S. Pat. No. 6,281,341), polyacrylates, a photopolymerizable poly(ethylene glycol) polymer, barium poly-L-lysine alginate capsules, calcium or barium alginate capsules, polyacrylonitrile/polyvinylchloride (PAN/PVC) hollow fibers, and polyethersulfone (PES) hollow fibers. U.S. Pat. No. 5,639,275, for example, describes improved devices and methods for long-term, stable expression of a biologically active molecule using a biocompatible capsule containing genetically engineered cells.

Another approach to encapsulate cells involves the use of photolithography techniques adapted from the semiconductor industry to encapsulate living cells in silicon capsules that have pores only a few nanometers wide (Desai 2002).

Also, suitable immune-compatible polycations, including but not limited to, poly-1-lysine (PLL) polycation or poly-1-ornithine or poly(methylene-co-guanidine)hydrochloride, may be used to encapsulate cells. Additionally, the sMAPCs may be encapsulated by membranes prior to implantation (e.g., biocompatible semipermeable membranes (e.g., the membrane lets nutrients, cellular factors and oxygen pass in and out of the blood stream, and preferably keeps out the antibodies and T cells of the immune system, which may destroy the cells)) to, for example, surround cells, sometimes within a capillary device, to create a miniature articial organ, such as one that would include functional pancreas, liver or kidney cells (e.g., a pancreatic, liver or kidney artificial device). The encapsulation provides a barrier to the host's immune system and inhibits graft rejection and inflammation. It is contemplated that any of the many methods of cell encapsulation available may be employed. In some instances, cells are individually encapsulated (microencapsulation). In other instances, many cells are encapsulated within the same membrane (macroencapsulation). Membranes can be used in a perfusion device, a capsule that is grafted to an artery where it makes direct contact with the body's circulating blood; in this way, the device can draw nutrients from the blood and release factors to circulate throughout the body. Another method provides for coating a small group of cells (macroencapsulation) or individual cells (microencapsulation) and implanting them inside the abdominal cavity. In these devices nutrients and factors would be exchanged by way of the body fluids permeating the tissues in which they are implanted. In embodiments in which the cells are removed following implantation, the relatively large size of a structure encapsulating many cells within a single membrane provides a convenient means for retrieval of the implanted cells. Several methods of cell encapsulation are well known in the art, such as those described in European Patent Publication No. 301,777 or U.S. Pat. Nos. 4,353,888; 4,744,933; 4,749,620; 4,814,274; 5,084,350; 5,089,272; 5,578,442; 5,639,275; and 5,676,943, each of which is incorporated herein by reference.

A. Bioreactors/Bioartificial Organs

One embodiment includes a bioreactor containing sMAPCs (e.g., a bioreactor containing pig liver cells for filtering and oxygenating the blood, wherein the bioreactor includes an outer shell (such as a plastic out shell) and hollow semi-permeable membrane fibers which are seeded with cells). In one embodiment, sMAPCs of the invention are incorporated in a bioreactor or an artificial organ, for in vivo or extracorporeal uses, such as for a bioartificial kidney (see, for example, U.S. Pat. No. 6,150,164) or a bioartificial liver. The bioreactor may be used to culture sMAPCs to produce cell products (e.g., the sMAPCs of the invention may also be used to express or provide one or more desired factors to a filtered biological fluid that is to be returned to a subject or otherwise manipulated or analyzed) or to functionally act on substances, such as toxins normally metabolized by, for example, the liver. The bioreactor may serve as, or be an integral part of, a liver or kidney assist device to treat a patient in need thereof.

One embodiment of the invention provides an extracorporeal Liver Assist Device (LAD) including sMAPCs or differentiated progeny. An extracorporeal Liver Assist Device (LAD) is a bioartificial liver (see, for example, U.S. Patent application publication number 20030228685 and Allen, J. W. et al. 2001; "HepatAssist" (Circe Biomedical); Rozga, J. et al. 1994; Nyberg, S. L. 1992) device that is designed to serve as a temporary liver support system for patients with acute or chronic liver failure. The LAD would function as a temporary support designed to provide hepatic function until liver transplantation or the regeneration of the patient's own liver. The principal goal of the LAD is to circulate a patient's plasma extracorporeally through a bioreactor that contains metabolically active hepatocytes, such as sMAPCs that have been induced to differentiate to hepatocytes. A conventional liver assist device includes a rigid, plastic outer shell and hollow semi-permeable membrane fibers which are seeded with cells. The fibers may be treated with collagen, lectin, laminin, or fibronectin, for the attachment of cells or left untreated. Bodily fluid is perfused through the device for detoxification according to well known procedures and then returned to the patient.

For example, a hemodialysis-type catheter pumps blood out of the patient's body and into an ultrafiltration generator, which separates the blood into plasma and its cellular components (blood cells). The plasma is then carried to the LAD. The LAD incorporates isolated hepatocytes, such as differentiated sMAPCs, into a bioreactor (e.g., hollow fiber, flat plate and monolayer, perfused bed or scaffold type bioreactor) to provide the synthetic functions of a normal liver. As the plasma is filtered through the LAD, the plasma is metabolically treated by the hepatocytes generated from sMAPCs, just as blood is filtered through the liver (to detoxify substances in the circulating plasma of patients in liver failure). After the plasma passes through the LAD, it is recombined with its cellular components and is returned to the patient's body.

5. Natural Killer (NK) Cell Function:

Any means, such as an agent, which inhibits NK cell function, including depleting NK cells from a population of cells, may also be administered to prevent immune rejection, increase engraftment or increase immune tolerance. Such an agent includes an anti-NK cell antibody, irradiation or any other method which can inhibit NK cell function. NK function inhibition is further described in PCT Application No. PCT/US2005/015740, filed May 5, 2005, which application is incorporated herein by reference for teaching methods of inhibiting NK cells to aid in stem cell persistence in vivo.

In one embodiment of the invention at least one agent for inhibiting NK cell function, including inhibition of NK cell-mediated cytotoxicity, is administered. NK cell function can be negated by NK depletion using either genetic (recipients deficient in NK cells) or epigenetic (in vivo depletion/inactivation with, for example, an anti-NK antibody) means. Any material capable of inhibiting NK cell function can be used (e.g., multimeric compounds that bind to P-Selectin Glycoprotein 1 (PSGL-1) on the surface of T cells or NK cells (U.S. Pat. Pub. No. 2004/0116333) or modulation of SH2-containing inositol phophatase (SHIP) expression or function (U.S. Pat. Pub. No. 2002/0165192)). Any means/agent including, but not limited to, chemical (e.g., a chemical compound, including, but not limited to, a pharmaceutical, drug, small molecule), protein (e.g., anti-NK cell antibody), peptide, microorganism, biologic, nucleic acid (including genes coding for recombinant proteins, or antibodies), or genetic construct (e.g., vectors, such as expression vectors, including but not limited to expression vectors which lead to expression of an antagonist against NK cell activity) can be used to inhibit NK cell function.

There are several antibodies available in the art which inhibit NK cell function, including but not limited to anti-human thymocyte globulin (ATG; U.S. Pat. No. 6,296,846), TM-β1 (anti-IL-2 receptor β chain Ab), anti-asialo-GM1 (immunogen is the glycolipid GA1), anti-NK1.1 antibodies or monoclonal anti-NK-cell antibodies (5E6; Pharmingen, Piscataway, N.J.). Additionally, antibodies directed against, for example, a natural cytotoxicity receptor (NCR), including, for example, NKp46, or an antibodies directed against a leukocyte-associated Ig like receptor family, including, for example, LAIR-1, or antibodies directed against a member of the killer cell immunoglobulin-like receptor (KIR) family, including, for example, KIR2DL1, KIR2DL2 or KR2DL3 are available to the art worker or can be made by methods available to an art worker and are useful in the present invention.

Additionally, a means, such as an agent which can cross-link LAIR-1 molecules on NK cells may be used to inhibit NK cell function. Also, irradiation (lethal, sub-lethal, and/or localized irradiation) may be used to inhibit NK cell function. In one embodiment, the means for inhibiting NK cell function is an antibody which is reactive with Natural Killer cells. Additionally, a means for inhibiting NK cell function can include agents that modulate the immune system, such as those developed for immunosuppression. It should be noted that any of these means/agents can be used alone or in combination.

Thus, there is also provided herein a method to increase immunologic tolerance in a subject to sMAPCs and other cells comprising administering a population of the sMAPCs and an effective amount of an agent for inhibiting Natural Killer cell function to the subject, so that immunologic tolerance to the sMAPCs increases compared to the method without administration of the inhibiting agent.

6. Gene Therapy:

sMAPCs can be extracted and isolated from the body, grown in culture in the undifferentiated state or induced to differentiate in culture, and genetically altered using a variety of techniques, especially viral transduction. Uptake and expression of genetic material is demonstrable, and expression of foreign DNA is stable throughout development. Retroviral and other vectors for inserting foreign DNA into stem cells are available to those of skill in the art. (Mochizuki, H. et al. 1998; Robbins, P. et al. 1997; Bierhuizen, M. et al. 1997; Douglas, J. et al. 1999; Zhang, G. et al. 1996). Once transduced using a retroviral vector, enhanced green fluorescent protein (eGFP) expression persists in terminally differentiated muscle cells, endothelium and c-Kit positive cells derived from isolated MAPCs, demonstrating that expression of retroviral vectors introduced into MAPC persists throughout differentiation. Terminal differentiation was induced from cultures initiated with about 10 eGFP$^+$ cells previously transduced by retroviral vector and sorted a few weeks into the initial MAPC culture period.

Monitoring of Subject After Administration of sMAPCs or Progeny Differentiated Therefrom Following transplantation, the growth or differentiation of the administered sMAPCs or progeny differentiated therefrom or the therapeutic effect of the sMAPCs or progeny may be monitored. For example, blood glucose, serum glucose and/or serum insulin may be monitored or muscle function may be tested.

The functionality of MAPCs to treat a cardiac disease may be monitored by various well-known techniques such as scintigraphy, myocardial perfusion imaging, gated cardiac blood-pool imaging, first-pass ventriculography, right-to-left shunt detection, positron emission tomography, single photon emission computed tomography, magnetic resonance imaging, harmonic phase magnetic resonance imaging, echocardiography, electrocardiography, analysis of cardiac function-specific proteins in the serum of the subject and myocardial perfusion reserve imaging.

Following administration, the immunological tolerance of the subject to the sMAPCs or progeny may be tested by various methods known in the art to assess the subject's immunological tolerance to sMAPCs. In cases where the subject's tolerance of sMAPCs is suboptimal (e.g., the subject's immune system is rejecting the exogenous sMAPCs), therapeutic adjunct immunosuppressive treatment, which is known in the art, of the subject may be performed.

Genetically-Modified sMAPCs sMAPCs or differentiated progeny derived therefrom can be genetically altered ex vivo, eliminating one of the most significant barriers for gene therapy. For example, a subject's bone marrow aspirate is obtained, and from the aspirate sMAPCs are isolated. The sMAPCs are then genetically altered to express one or more preselected gene products. The sMAPCs can then be screened or selected ex vivo to identify those cells which have been successfully altered, and these cells can be introduced into a subject or can be differentiated and introduced into a subject, either locally or systemically. Alternately, sMAPCs can be differentiated and then the differentiated cells can be genetically altered prior to administration. In either case, the cells provide a stably-transfected source of cells that can express a preselected gene product.

Methods for Genetically Altering sMAPCs

Cells isolated by the methods described herein, or their differentiated progeny, can be genetically modified by introducing DNA or RNA into the cell by a variety of methods available to those of skill in the art. These methods are generally grouped into four major categories: (1) viral transfer, including the use of DNA or RNA viral vectors, such as retroviruses, including lentiviruses (Mochizuki, H., et al., 1998; Martin, F., et al. 1999; Robbins, et al. 1997; Salmons, B. and Gunzburg, W. H., 1993; Sutton, R., et al., 1998; Kafri, T., et al., 1999; Dull, T., et al., 1998), Simian virus 40 (SV40), adenovirus (see, for example, Davidson, B. L., et al., 1993; Wagner, E., et al., 1992; Wold, W., *Adenovirus Methods and Protocols*, Humana Methods in Molecular Medicine (1998), Blackwell Science, Ltd.; Molin, M., et al., 1998; Douglas, J., et al., 1999; Hofmann, C., et al., 1999; Schwarzenberger, P., et al., 1997), alpha virus, including Sindbis virus (U.S. Pat. No. 5,843,723; Xiong, C., et al., 1989; Bredenbeek, P. J., et al., 1993; Frolov, I., et al., 1996), herpes virus (Laquerre, S., et al., 1998) and bovine papillomavirus, for example; (2) chemical transfer, including calcium phosphate transfection and DEAE dextran transfection methods; (3) membrane fusion transfer, using DNA-loaded membranous vesicles such as liposomes (Loeffler, J. and Behr, J., 1993), red blood cell ghosts and protoplasts, for example; and (4) physical transfer techniques, such as microinjection, microprojectile J. Wolff in "Gene Therapeutics" (1994) at page 195. (see J. Wolff in "Gene Therapeutics" (1994) at page 195; Johnston, S. A., et al., 1993; Williams, R. S., et al., 1991; Yang, N. S., et al., 1990), electroporation, nucleofection or direct "naked" DNA transfer.

Cells can be genetically altered by insertion of pre-selected isolated DNA, by substitution of a segment of the cellular genome with pre-selected isolated DNA, or by deletion of or inactivation of at least a portion of the cellular genome of the cell. Deletion or inactivation of at least a portion of the cellular genome can be accomplished by a variety of means, including but not limited to genetic recombination, by anti-sense technology (which can include the use of peptide nucleic acids or PNAs), or by ribozyme technology, for example. Insertion of one or more pre-selected DNA sequences can be accomplished by homologous recombination or by viral integration into the host cell genome. Methods of non-homologous recombination are also known, for example, as described in U.S. Pat. Nos. 6,623,958, 6,602,686, 6,541,221, 6,524,824, 6,524,818, 6,410,266, 6,361,972, the contents of which are specifically incorporated by reference for their entire disclosure relating to methods of non-homologous recombination.

The preselected gene sequence can also be incorporated into the cell, particularly into its nucleus, using a plasmid expression vector and a nuclear localization sequence. Methods for directing polynucleotides to the nucleus have been described in the art. For example, signal peptides can be attached to plasmid DNA, as described by Sebestyen, et al. (1998), to direct the DNA to the nucleus for more efficient expression.

The genetic material can be introduced using promoters that will allow for the gene of interest to be positively or negatively induced using certain chemicals/drugs, to be eliminated following administration of a given drug/chemical, or can be tagged to allow induction by chemicals (including but not limited to the tamoxifen responsive mutated estrogen receptor) in specific cell compartments (including, but not limited to, the cell membrane).

Any of these techniques can also be applied to introduce a transcriptional regulatory sequence into sMAPCs or progeny to activate a desired endogenous gene. This can be done by both homologous (e.g., U.S. Pat. No. 5,641,670) or non-homologous (e.g., U.S. Pat. No. 6,602,686) recombination. These patents are incorporated by reference for teaching of methods of endogenous gene activation.

Successful transfection or transduction of target cells can be demonstrated using genetic markers, in a technique that is known to those of skill in the art. The green fluorescent protein of *Aequorea victoria*, for example, has been shown to be an effective marker for identifying and tracking genetically modified hematopoietic cells (Persons, D., et al., 1998). Alternative selectable markers include the β-Gal gene, the truncated nerve growth factor receptor, drug selectable markers (including but not limited to NEO, MTX, hygromycin).

In another embodiment, the sMAPCs are derived from transgenic animals, and thus, are in a sense already genetically modified. There are several methods presently used for generating transgenic animals. The technique used most often is direct microinjection of DNA into single-celled fertilized eggs. Other techniques include retroviral-mediated transfer, or gene transfer in embryonic stem cells. Use of these transgenic animals has certain advantages including the fact that there is no need to transfect healthy cells. sMAPCs derived from transgenic animals will exhibit stable gene expression. Using transgenic animals, it is possible to breed in new genetic combinations. The transgenic animal may have integrated into its genome any useful gene.

When the genetic modification is for the production of a biologically active substance, the substance will generally be one that is useful for the treatment of a given injury and/or disease. For example, it may be desired to genetically modify cells so they secrete a certain growth factor, growth factor receptor or cytokine.

Protein Transduction

Proteins can be transferred directly to MAPCs when they are linked to a protein transduction domain (PTD), small cationic peptide domains that can freely and rapidly cross cell membranes. Several PTDs such as poly-arginine (poly-arginine-mediated protein transduction) and HIV-derived Tat have been identified that allow a fused protein to efficiently cross cell membranes. A distinct advantage of protein transduction is that the transduced proteins are present in the cells only transiently, a feature which depends on the intrinsic turnover of the expressed protein. In addition, intracellular concentration of the transduced protein can be controlled by varying the amount of protein added.

Use of sMAPCs

A. Animal Models

Animals can be used as models of human disease or disease of animals. Useful animal models for human diseases include, but are not limited to, cancer, autoimmune, diabetes, atherosclerosis and other cardiovascular diseases, Down Syndrome, muscular dystrophy, obesity, deafness, inherited syndromes and neurodegenerative disease. Many of these disease can be created in animal models by transgenic technologies (e.g., genetic manipulations are done to develop animals (e.g., mice, rats, rabbits, sheep and pigs) that acquire heritable diseases similar to some of those with which humans are afflicted). Examples of animal models include, but are not limited to, induction of cancer in a mouse to simulate cancer in a human; a genetic disease in a pure-bred dog that is similar to a human disease; simulating a heart attack in a canine model, and organ transplanting between 2 pigs (or two different animal species). Several U.S. Patents describing various animal models for disease include, but are not limited to, U.S. Pat. Nos. 4,736,866; 5,175,383; 5,175,384; 5,175,385; 5,183,949; 5,387,742; 5,633,425; 5,625,125; 5,625,124; 5,602,309; 5,602,307; 5,602,306; 5,602,299; 5,569,827; 5,569,824; 5,550,316; 5,565,186; 5,491,283; 5,489,743; 5,476,995; 5,589,604; 5,322,775; 5,639,940; 5,625,126; and 5,602,306. Animal models allow for the study of the way the disease progresses and what factors are important to the disease process. The model can also be used to study disease treatment, for example, the animal model can be used to study whether sMAPCs can prevent, ameliorate, treat or cure diseases.

Swine MAPCs can be used in an animal model for the investigation and analysis of cell based therapies. For example, the isolation of swine MAPCs provides for an animal model, including a large animal model, for preclinical investigation for safety and effectiveness of the MAPCs in disease models, including, but not limited to, cardiovascular disease, liver disease, renal disease, or diabetes cancer, autoimmune, Down Syndrome, muscular dystrophy, obesity, deafness, inherited syndromes and neurodegenerative disease. Thus, the animal model is directed towards the ability to mimic certain diseases (e.g., a surgically induced/created myocardial infarction) and/or injuries in animals and investigate the role of MAPC based therapy in the treatment of the diseases and/or injuries. These diseases and/or injuries can be created, for example, by diet, drugs, chemicals, environment, infection, trauma, surgery, genetic alteration and/or genetic defects.

For example, sMAPCs and a pig model for cardiac disease (e.g., induced MI) may be used in the study of cardiac diseases and the regeneration of cardiac tissue by administering sMAPCs to the animal with the disease. Experimental and clinical evidence demonstrates that cellular transplantation improves the LV contractile performance of failing hearts. The majority of these studies use a rodent as the animal model. However, there is a need in the art for data from larger animals (between the mouse and human). This is because there are instances in which beneficial effects occurred in mouse models that were not observed in human clinical trials. It is known there are differences between mouse heart and human heart, anatomically and physiologically. Also, the heart is not a heterogeneous organ, and the inner layers of the left ventricle are more vulnerable to oxidative stress and other disease insults. In addition, in the heart with post-infarction LV remodeling, it is known that periscar areas are dysfunctioned and the expansion of this area is thought to be related to the development of heart failure. The small size of the mouse heart makes it difficult to evaluate the functional consequences of cell transplantation with spatial differentiation. Furthermore, the establishment of the sMAPC cell line makes it possible to examine the feasibility of using banked (frozen) cell products as an-off-the-shelf product for myocardial repair. The frozen banked cells would make cells rapidly available (i.e., following urgent revascularization) for transplantation without the time delays incurred during marrow extraction and cell line expansion.

Additionally, transplanted cells can be used for diagnostic and/or research purposes. For example, in some embodiments, sMAPCs are transplanted into a host, such as a pig, and the host is exposed to stimuli (e.g., drugs, diets, aging, hormones, etc.) so that the effect of the stimuli on differentiation, proliferation, homing, grafting and function of the MAPCs can be monitored. In some embodiments, the transplanted cells may contain a transgene that, upon expression, provides a marker. The marker may be used to identify the cells in the host or to identify an effect on the transplanted cells caused by their environment.

One embodiment provides a method to determine the efficacy of sMAPCs to treat a disease or injury by administering sMAPCs to a non-human animal model for said disease or injury and evaluating said animal to determine if one or more symptoms of said disease or injury is ameliorated by said administration. Another embodiment provides a non-human animal comprising exogenous sMAPCs. Another embodiment provides a method to prepare a non-human animal comprising administering sMAPCs to a non-human.

B. Therapeutic Uses sMAPCs differentiate to form all three germ cell layers. For example, sMAPCs can be induced to differentiate into chondrocytes, hepatocytes, endothelial cells, cardiomyocytes, smooth muscle cells, and neural cells. As such, sMAPCs or progeny differentiated therefrom can be used to treat essentially any injury or disease, particularly a disease associated with pathological organ or tissue physiology or morphology which is amenable to treatment by transplantation in any mammalian species, preferably in a human subject (e.g., xenogeneic transplantation). Administered sMAPCs may contribute to generation of new tissue by differentiating in vivo. For example, sMAPCs can be used to repopulate heart muscle cells, or cells or any other organ or tissue, by either direct injection into the area of tissue damage or by systemic injection, allowing the cells to home to the tissue or organ. This method can be particularly effective if combined with angiogenesis. Both methods of injection and methods for promoting angiogenesis are known to those of skill in the art. sMAPCs provide a broader differentiation range to provide a more varied source of cells for cardiac or other tissue repair utilizing these techniques.

Alternatively, or in addition, administered sMAPCs may contribute to generation of new tissue by secreting cellular factors that aid in homing and recruitment of endogenous MAPCs or other stem cells, such as cardiac, hematopoietic or mesenchymal stem cells, or other more differentiated cells, such as myoblasts or myocytes.

Alternatively, or in addition, sMAPCs may secrete factors that act on endogenous stem or progenitor cells in the target tissue causing them to differentiate in the target site, thereby enhancing function.

sMAPC or differentiated progeny, such as osteoblasts, can be used to treat osteoporosis, Paget's disease, bone fracture, osteomyelitis, osteonecrosis, achondroplasia, osteogenesis imperfecta, hereditary multiple exostosis, multiple epiphyseal dysplasia, Marfan's syndrome, mucopolysaccharidosis, neurofibromatosis or scoliosis, reconstructive surgery for localized malformations, spina bifida, hemivertebrae or fused vertebrae, limb anomalies, reconstruction of tumor-damaged tissue, and reconstruction after infection, such as middle ear infection.

sMAPC or differentiated progeny, such as chondrocytes, can be used to treat age-related diseases or injuries, sports-related injuries, or specific diseases such as rheumatoid arthritis, psoriasis arthritis, Reiter's arthritis, ulcerative colitis, Crohns' disease, ankylosing spondylitis, osteoarthritis, reconstructive surgery of the outer ear, reconstructive surgery of the nose, and reconstructive surgery of the cricoid cartilage.

sMAPC or differentiated progeny, such as adipocytes, can be used in resculpting during reconstructive or cosmetic surgery, as well as for the treatment of Type II diabetes. In reconstructive surgery, adipocytes differentiated from sMAPCs can be used for breast reconstruction after mastectomy, for example, or for reshaping tissue lost as a result of other surgery, such as tumor removal from the face or hand. In cosmetic surgery, adipocytes differentiated from MAPCs can be used in a variety of techniques, such as breast augmentation, or for reduction of wrinkles in aging skin. Adipocytes thus derived can also provide an effective in vitro model system for the study of fat regulation.

sMAPC or differentiated progeny, such as fibroblasts, can be used for cell therapy or tissue repair to promote wound healing or to provide connective tissue support, such as scaffolding for cosmetic surgery.

sMAPC or differentiated progeny, such as skeletal muscle cells, can be used for cell therapy or tissue repair in the treatment of Duchene muscular dystrophy, Becker muscular dystrophy, myotonic dystrophy, skeletal myopathy, and reconstructive surgery to repair skeletal muscle damage.

sMAPC or differentiated progeny, such as smooth muscle cells, can be used in cell therapy or tissue repair in the treatment of developmental abnormalities of the gastrointestinal system, such as oesophageal atresia, intestinal atresia, and intussusception, as well as for replacement of tissues after surgery for bowel infarction or colocolostomy.

Smooth muscle cells formed from the sMAPCs can also be used for bladder or uterine reconstruction, for neovascularization, for repair of vessels damaged by, for example, atherosclerosis or aneurysm. Smooth muscle precursor cells (mesangial cells) can be used as an in vitro model for glomerular diseases or for cell therapy or tissue regeneration in diabetic neuropathy. Smooth muscle precursors can also be used to repair macula densa of the distal convoluted tubule or juxtaglomerular tissues, which play a role in blood pressure regulation.

sMAPC or differentiated progeny, such as cardiomyocytes, can be useful for cell therapy or tissue repair for treating heart tissue damaged following myocardial infarction, in conjunction with congestive heart failure, during valve replacement, by congenital heart anomalies, or resulting from cardiomyopathies or endocarditis. Cells can be delivered locally, especially by injection, for increased effectiveness.

MAPCs or differentiated progeny, such as neuroectodermal cells, such as microglial cells, can be used to treat spinal cord injuries and neurodegenerative disorders, such as Huntingtons disease, Parkinsons disease, Multiple Sclerosis, and Alzheimers disease, as well as repair of tissues damaged during infectious disease affecting the central nervous system. Microglial cells that have been genetically altered to produce cytokines can also be used for transplantation for the treatment of infectious disease in the central nervous system where access is limited due to the blood-brain barrier. Glial cells can also be used to produce growth factors or growth factor inhibitors for regeneration of nerve tissue after stroke, as a consequence of multiple sclerosis, amylotropic lateral sclerosis, and brain cancer, as well as for regeneration after spinal cord injury. MAPCs induced to form oligodendrocytes and astrocytes, for example, can be used for transplant into demyelinated tissues, especially spinal cord, where they function to myelinate the surrounding nervous tissues. This technique has been demonstrated effective in mice, using embryonic stem cells as the source of oligodendrocyte and astrocyte precursors (Brustle, O., et al., *Science* (1999) 285: 754-756). The MAPCs of the present invention exhibit the broad range of differentiation characteristic of embryonic cells, but provide the added advantage of contributing autologous cells for transplant.

The cells of the present invention can be used in cell replacement therapy and/or gene therapy to treat congenital neurodegenerative disorders or storage disorders such as, for instance, mucopolysaccharidosis, leukodystrophies (globoid-cell leukodystrophy, Canavan disease), fucosidosis, GM2 gangliosidosis, Niemann-Pick, Sanfilippo syndrome, Wolman disease, and Tay Sacks. They can also be used for traumatic disorders such as stroke, CNS bleeding, and CNS trauma; for peripheral nervous system disorders such as spinal cord injury or syringomyelia; for retinal disorders such as retinal detachment, macular degeneration and other degenerative retinal disorders, and diabetic retinopathy.

sMAPC or differentiated progeny, such as stromal cells, can be used as transplant cells for post-chemotherapy bone marrow replacement, as well as for bone marrow transplantation. In breast cancer, for example, a bone marrow aspirate is obtained from a patient prior to an aggressive chemotherapy regimen. Such chemotherapy is damaging to tissues, particularly to bone marrow. MAPCs isolated from the patient's bone marrow can be expanded in culture to provide enough autologous cells for re-population of the bone marrow cells. Because these cells can differentiate to multiple tissues types, cells introduced either locally or systemically provide an added advantage by migrating to other damaged tissues, where cellular factors in the tissue environment induce the cells to differentiate and multiply.

sMAPC or differentiated progeny, such as endothelial cells, can be used in the treatment of Factor VIII deficiency, as well as to produce angiogenesis for neovascularization. Endothelial cells can also provide an in vitro model for tumor suppression using angiogenic inhibitors, as well as an in vitro model for vasculitis, hypersensitivity and coagulation disorders. Using these cultured endothelial cells and rapid screening methods known to those of skill in the art, thousands of potentially useful therapeutic compounds can be screened in a more timely and cost-effective manner.

sMAPC or differentiated progeny, such as hematopoietic cells, can be used to repopulate the bone marrow after high dose chemotherapy. Prior to chemotherapy, a bone marrow aspirate is obtained from the patient. Stem cells are isolated by the method of the present invention, and are grown in culture and induced to differentiate. A mixture of differentiated and undifferentiated cells is then reintroduced into the patient's bone marrow space. Clinical trials are currently underway using hematopoietic stem cells for this purpose. The stem cells of the present invention, however, provide the additional benefit of further differentiation to form cells that can replace those damaged by chemotherapy in other tissues as well as in bone marrow. Hematopoietic cells derived from the MAPCs can be further differentiated to form blood cells to be stored in blood banks, alleviating the problem of a limited supply of blood for transfusions.

sMAPC or differentiated progeny, such as ectodermal cells, can be used in cell replacement therapy and/or gene therapy to treat or alleviate symptoms of skin disorders such as alopecia, skin defects such as burn wounds, and albinism.

sMAPC or differentiated progeny, such as endodermal epithelial cells, can be used in cell replacement therapy and/or gene therapy to treat or alleviate symptoms of several organ diseases. The cells could be used to treat or alleviate congenital liver disorders, for example, storage disorders such as mucopolysaccharidosis, leukodystrophies, GM2 gangliosidosis; increased bilirubin disorders, for instance Crigler-Najjar syndrome; ammonia disorders such as inborn errors of the urea-cycle, for instance Ornithine decarboxylase deficiency, citrullinemia, and argininosuccinic aciduria; inborn errors of amino acids and organic acids such as phenylketoinuria, hereditary tyrosinemia, and Alpha1-antitrypsin deficiency; and coagulation disorders such as factor VIII and IX deficiency. The cells can also be used to treat acquired liver disorders due to viral infections. The cells of the present invention can also be used in ex vivo applications such as to generate an artificial liver (akin to kidney dialysis), to produce coagulation factors and to produce proteins or enzymes generated by liver epithelium.

These epithelial cells of the present invention can also be used in cell replacement therapy and/or gene therapy to treat or alleviate symptoms of biliary disorders such as biliary cirthosis and biliary atresia.

The epithelial cells of the present invention can also be used in cell replacement therapy and/or gene therapy to treat or alleviate symptoms of pancreas disorders such as pancreatic atresia, pancreas inflammation, Alpha1-antitrypsin deficiency, and diabetes (subcutaneous implantation or intra-pancreas or intra-liver implantation). Further, the epithelial cells of the present invention can also be used in cell replacement therapy and/or gene therapy to treat or alleviate symptoms of gut epithelium disorders such as gut atresia, inflammatory bowel disorders, bowel infarcts, and bowel resection.

For example, diseases treatable by sMAPC based therapy include, but are not limited to, genetic diseases, degenerative diseases, cardiovascular diseases, metabolic storage diseases, neural diseases, cancer and renal, pancreatic, cardiac, hepatic, hematological, pulmonary, brain, gastrointestinal, muscular, endocrine, neural, metabolic, dermal, cosmetic, ophthalmological, and vascular diseases. In one embodiment, sMAPCs or progeny differentiated therefrom are administered to treat a renal, hepatic, pancreatic, cardiac, genetic and/or hematological disease. MAPCs can also be used to treat blindness, caused by, but not limited to, neuroretinal disease caused by among other things macular degeneration, diabetic retinopathy, glaucoma, retinitis pigmentosa.

Examples of renal diseases which can be treated using sMAPCs or progeny differentiated therefrom include, but are not limited to, acute kidney failure, acute nephritic syndrome, analgesic nephropathy, atheroembolic kidney disease, chronic kidney failure, chronic nephritis, congenital nephrotic syndrome, end-stage kidney disease, Goodpasture's syndrome, IgM mesangial proliferative glomerulonephritis, interstitial nephritis, kidney cancer, kidney damage, kidney infection, kidney injury, kidney stones, lupus nephritis, membranoproliferative glomerulonephritis I, membranoproliferative glomerulonephritis II, membranous nephropathy, necrotizing glomerulonephritis, nephroblastoma, nephrocalcinosis, nephrogenic diabetes insipidus, IgA-mediated nephropathy, nephrosis, nephrotic syndrome, polycystic kidney disease, post-streptococcal glomerulonephritis, reflux nephropathy, renal artery embolism, renal artery stenosis, renal papillary necrosis, renal tubular acidosis type I, renal tubular acidosis type II, renal underperfusion and renal vein thrombosis.

Examples of pancreatic diseases which can be treated using sMAPCs or progeny differentiated therefrom include, but are not limited to, diabetes (including Type 1, Type 2, MODY and other genetic causes of diabetes), pancreatic atresia, pancreas inflammation, alpha 1-antitrypsin deficiency, acute, chronic or hereditary pancreatitis, pancreatic cancer (including endocrine tumors of the pancreas), pancreas malfunction due to cystic fibrosis or Shwachman Diamond syndrome, pancreatic insufficiency or pancreatic enzyme deficiency, pancreatic cysts, hyperinsulinism, pancreatic digestive diseases, genetic disorders of the exocrine pancreas and pancreatic injury, including, but not limited to, injury as a result of physical trauma (including, but not limited to, surgery), chemical, radiological, aging, and disease.

Examples of hepatic diseases which can be treated using sMAPCs or progeny differentiated therefrom include, but are not limited to, hepatitis C infection, hepatic cirrhosis, primary sclerosing cholangitis, hepatocellular carcinoma, alcoholic liver disease, and hepatitis B.

In the case of cardiac disease, diseases which can be treated using sMAPCs or progeny differentiated therefrom include, but are not limited to, myocarditis, cardiomyopathy, heart failure, damage caused by heart attacks, hypertension, atherosclerosis, heart valve dysfunction. Progeny can include cardiomyocytes that repopulate the injured tissue or endothelial cells that provide neo-vascularization to the tissue.

In one embodiment, sMAPC-based therapies can be used to treat damage resulting from disease states including, but not limited to, congestive heart failure, coronary artery disease, myocardial infarction, myocardial ischemia, effects of atherosclerosis or hypertension, cardiomyopathy, cardiac arrhythmias, infective myocarditis, hypersensitivity myocarditis, autoimmune endocarditis, and congenital heart disease.

Cardiac injury, such as MI, promotes tissue responses that enhance myogenesis using implanted sMAPCs. Thus, administration of sMAPCs can, for example, reduce the degree of scar formation, augment ventricular function, and compensate for weakened cardiac muscle, thereby improving cardiac function. New muscle is thereby created within an infarcted myocardial segment. Preferably, sMAPCs can be directly infiltrated into the zone of infarcted tissue. In preferred embodiments, engraftment of sMAPCs is within cardiac muscle in acute myocardial infarction.

In the case of degenerative myocardial disease, sMAPCs provide for both myocyte replacement and stimulation of angiogenesis. Improved cardiac function can be indicated, for example, by increased perfusion. This therapy can be used as a stand alone therapy or in conjunction with revascularization therapies. sMAPCs also offer the advantage of forming vascular structures to furnish and supply blood to the emerging cardiac muscle mass.

In the case of cardiac diseases, the invention provides several methods of treatment. One embodiment provides a method of providing cardiac muscle to a subject in need thereof by administering to the subject, in an amount effective to provide new cardiac muscle, isolated sMAPCs.

Another embodiment provides a method of increasing cardiac muscle mass by contacting an amount of isolated sMAPCs with existing cardiac muscle effective to generate new cardiac muscle.

Also provided is a method of producing cardiac muscle cells in a subject by administering to the subject, in proximity to existing cardiac muscle and in an amount effective to produce cardiac muscle cells, isolated sMAPCs.

Additionally, sMAPCs programmed to differentiate into endothelial and/or smooth muscle cell lineages along with fibrillar biopolymeric matrices may be used as a stand alone therapy or in addition to other therapies so as to form tissue engineered blood vessels. For example, one embodiment provides a method of producing a tissue-engineered blood vessel by entrapping at least endothelial and smooth muscle cells derived from sMAPCs in a biopolymeric matrix (including, but not limited to, fibrin, fibrinogen and thrombin, laminin, collagen, proteoglycans, amphiphilic di-block copolymers or amphiphilic tri-block copolymers) and culturing the cells on the outer surface of a porous tube (e.g., porous plastic, including, but not limited to, polyethylene), wherein medium comprising a tactic factor (including, but not limited to, VEGF) is present inside the tube, such that a bilayered structure is formed, thereby producing a tissue-engineered blood vessel. The tissue-engineered blood vessel can then be implanted into a subject.

Another method of cardiac therapy involves the administration of cardiac tissue developed in vitro from sMAPCs (i.e., a bioengineered heart muscle/cardiac patch). For example, sMAPCs can be differentiated to form cardiomyocytes, which can then generate cardiac tissue/muscle. This tissue can then be administered/transplanted into a subject.

sMAPC-based therapies are not limited to improvement of cardiac muscle pathologies, but can be extended to any type of muscular disorder in which the primary pathology is loss of striated muscle mass and/or function. This would include, but is not limited to, muscle degeneration, muscular dystrophies, trauma, myasthenia gravis, and toxin-induced muscle abnormalities. Thus, in another embodiment, the present invention comprises methods of increasing striated muscle tissue mass by contacting a suitable amount of sMAPCs with existing striated muscle tissue and generating viable striated muscle tissue.

Examples of hematological and/or genetic diseases which can be treated using sMAPCs or progeny derived therefrom include, but are not limited to, coagulation disorders/coagulation factor deficiencies such as hemophilia and lysosomal storage diseases/enzyme deficiencies, such as Gaucher disease.

Additionally, genetically engineered sMAPCs which selectively express an endogenous or transgene, can be used to treat disease in a subject.

In utero transplantation of a population of sMAPCs to form chimerism of cells or tissues, thereby producing cells in prenatal or postnatal subjects following transplantation, wherein the cells produce therapeutic enzymes proteins or other products in the subject so that genetic defects are corrected can also be used for treatment of a subject.

Additionally, a method of using the cells for gene therapy in a subject in need of therepeuctic treatment, involving genetically altering the cells by introducing into the cell an isolated pre-selected DNA encoding a desired gene product and introducing the cells into the body of the subject to produce the desired gene product is provided.

Also provided is a method of repairing damaged tissue in a subject in need of such repair by expanding a population of sMAPCs in culture and contacting an effective amount of the expanded cells with the damaged tissue of the subject.

sMAPCs can also be used as antigen-presenting cells when genetically altered to produce an antigenic protein. Administration of such cells provides for a safe method for vaccine delivery.

EXAMPLES

The following examples are provided in order to demonstrate and further illustrate certain embodiments and aspects of the present invention and are not to be construed as limiting the scope thereof.

Materials and Methods

Chemicals and Cytokines Used

MCDB-201, retinoic acid (RA), DMSO, human (hu) EGF (epidermal growth factor), LA-BSA and ITS were obtained from Sigma, low glucose DMEM were obtained from Gibco BRL and hu-PDGF-BB (platelet-derived growth factor BB), hu-VEGF-165 (vascular endothelial growth factor), hu-HGF (hepatocyte growth factor), hu-bFGF (basic fibroblast growth factor), hu-FGF-4 (Fibroblast growth factor-4), hu-Noggin were obtained from R&D Systems. Fetal bovine serum was obtained from Hyclone.

Antibodies Used

Antibodies against NF-200 (N5389, 1:400), S100b (S-2657; 1:400) S100A2 (S-6797, 1:400), Tyrosine hydroxylase (TH) (T-2928, 1:1000), Serotonin (S-5545, 1:500), MAP2 (M4403, 1:200), α-SM-actin (C6198), calponin (C2687), and vWF (F3520, 1:200) were from Sigma. Polyclonal antibodies against Oct-3/4 (sc8630, 1:300), HNF-1 (sc8986, 1:300), HNF-1 (sc8986; 1:300), Tau (sc1995, 1:200), Ve-Cadherin (sc6458, 1:200) and Flk-1 (C1158, 1:200) were from Santa Cruz Biotechnology. Antibodies against CD31 (RDI-RTCD31-3A 1:200), CD45 (RDI-PIGCD45-E4 1:200), CD44 (RDI-PIGCD44abrt, 1:200), MHC Class I (PT85A, 1:200) and MHC Class II (TH81A5; 1:200) were from Research Diagnostics Inc. Monoclonal antibodies against GFAP (Glial Fibrillary Acidic protein) (Z0334, 1:400), polyclonal vWF (A0082 1:200) and Albumin (A0001, 1:200) were from DAKO. Antibodies against smoothelin (MAB3242) and against Caldesmon (MAB3576) were from Chemicon International. Monoclonal antibodies against porcine VCAM-1 (APG106, 1:200) were from Antigenix America Inc. Monoclonal antibodies against porcine albumin (A100-110F, 1:200) and Cytokeratin 18 (03-10500, 1:200) were from Bethyl Laboratories Inc. and US Biomax, respectively. Goat Anti-SM22 alpha polyclonal antibody was from Genetex (GTX10135). Secondary anti mouse/goat/rabbit Alexa Fluor 488 or 594 were from Molecular Probe.

Control Cell Populations

Since swine ES cells do not exist, the human embryonic stem cell line HP9 was used as a reference control for self-renewal markers for the swine system. Swine mesenchymal stem cells (swMSCs) were isolated and identified as describe (Liu J., et al. 2004).

Karyotyping

Cells, plated at about 500 cells/cm² 48 hours prior to harvesting, were subjected to 100 μl/ml clocemid incubation for 2-3 hours and collected with Trypsin-EDTA followed by lysis with a hypotonic solution and fixation in alcohol. Metaphases were analyzed after Geimsa (Leishmania) staining.

Telomere Length and Telomerase Activity

Telomere length and telomerase activity was measured by means of the telomere length assay kit from Pharmingen (Frankin Lakes, N.J.) according to the manufacture's recommendations.

RNA Isolation and Q-RT-PCR

RNA was extracted from sMAPCs or cells differentiated therefrom utilizing the RNeasy RNA isolation kit (Qiagen). The mRNA was purified from genomic DNA via Turbo DNase Set (Ambion). The mRNA was reverse transcribed, and cDNA underwent 40 rounds of amplification (ABI PRISM 7700; Perkin Elmer/Applied Biosystems) with the following reaction conditions: 40 cycles of a two-step polymerase chain reaction (PCR; 95° C. for 15 seconds, 60° C. for 60 seconds) after initial denaturation (95° C. for 10 min) with 2 μl of DNA solution, 1×TaqMan SYBR Green Universal Mix PCR reaction buffer. Primers used for amplification are listed in Table 1 (concentration: 150 nM). The mRNA levels were normalized using GAPDH as a housekeeping gene and compared with levels in adult or fetal swine tissues. Primer specificity was confirmed by product sequencing.

TABLE 1

PCR Primers

| | Forward | Reverse |
|---|---|---|
| OCT-3a | CTTCGGATTTCGCCTTCTCG (SEQ ID NO:1) | CCTTGGAAGCTTAGCCAGGTC (SEQ ID NO:27) |
| Rex-1 | AGCTCACGCGTCATCAGAG (SEQ ID NO:71) | CACTCACCGCAGTGGTAGG (SEQ ID NO:72) |
| GAPDH | CACTGAGCACCAGGTTGTGT (SEQ ID NO:73) | CCTGTTGCTGTAGCCAAATTC (SEQ ID NO:74) |
| HNF-1a | GTTCCAGGCCTACGAGAGG (SEQ ID NO:2) | TGACCAAACAGCCCTTCTG (SEQ ID NO:28) |
| HNF-3b | AAATGGACCTCAAGGCCTACG (SEQ ID NO:3) | ATGGCCAGGCTTCCTGG (SEQ ID NO:29) |
| Albumin | GCAGACCTATGCACACTTCCT (SEQ ID NO:4) | GCCCAGGACAGTTCTCAGTT (SEQ ID NO:30) |
| CK18 | GAGGCCCTGCTGAACATCAA (SEQ ID NO:5) | TCCAGAGCGTCGCCAAG (SEQ ID NO:31) |
| CK19 | CCCGCGACTACAGCCACTAC (SEQ ID NO:6) | TGCAGGACTATCTTGGAGTTCTCA (SEQ ID NO:32) |
| CYP2B6 | GTGTTCCCCACACGGTCACTA (SEQ ID NO:7) | TGGGTCATGGAGAGCAGAGG (SEQ ID NO:33) |

TABLE 1-continued

PCR Primers

| | Forward | Reverse |
|---|---|---|
| PECAM | AGAAGACGAGTGCGGAGTACA (SEQ ID NO:8) | ACGACTCCACCTTCGATCAC (SEQ ID NO:34) |
| FLK-1 | CAAAACTGTCGTGATTCCATGTC (SEQ ID NO:9) | TTCTGTTACCATCAGGAACAAACCT (SEQ ID NO:35) |
| FLT-1 | CGTGCAGATGGACGAAGAC (SEQ ID NO:10) | GTTCCACAAATCTTGGCCTTT (SEQ ID NO:36) |
| Tie-1 | GCCATGATCAAGAAGGACGG (SEQ ID NO:11) | TCCAGTTCTCCCGCGAAGT (SEQ ID NO:37) |
| vWF | TGCTCTGGGTTCGTCAGAGTC (SEQ ID NO:12) | CAGGCAAGTCACTGTGTGGC (SEQ ID NO:38) |
| Tek | GGACACCACCCAAATATCATCA (SEQ ID NO:13) | AAGTCCAGGAGATTCCCATGG (SEQ ID NO:39) |
| VE-Cadherin | CAGCAACGGCTACTCACAAA (SEQ ID NO:14) | ATTCTTCCCCATGAGGCTCT (SEQ ID NO:40) |
| Islet-1 | GTGATCCGGGTCTGGTTTC (SEQ ID NO:15) | CATGGGAGTTCCTGTCATCC (SEQ ID NO:41) |
| OTX-2 | GGGCTGAGTCTGACCACTTC (SEQ ID NO:16) | CCGAGTGAACGTCGTCCT (SEQ ID NO:42) |
| NF200 | CAGAGCTGGAGGCACTGAA (SEQ ID NO:17) | CATCTCCCACTTGGTGTTCC (SEQ ID NO:43) |
| MAP-2 | AAAGACCAACCTGCAGCTCTG (SEQ ID NO:18) | TCCACTGGGACCGTCTGTTC (SEQ ID NO:44) |
| NCAM | CACACACACACACACGCATT (SEQ ID NO:19) | GGAGCTCCCGTGTTGATCT (SEQ ID NO:45) |
| MBP | GAGGCAGAGCTCCTGACTACAAAC (SEQ ID NO:20) | GTCCCGTCCTCCCAGCTT (SEQ ID NO:46) |
| Tau | GTCCCTGGATAACATCACCCA (SEQ ID NO:21) | CGTGGTCCGTCTTGGCTTT (SEQ ID NO:47) |
| PAX-6 | GTTGGTATCCGGGGACTTC (SEQ ID NO:22) | CGTTGGAACTGATGGAGTTG (SEQ ID NO:48) |
| GFAP | GTGCAGACCTTCTCCAACCT (SEQ ID NO:77) | GCCTTCTGACACAGACTTGGT (SEQ ID NO:78) |
| Myocardin | GGAGTCAGCAGATGGATGAACT (SEQ ID NO:23) | GAAGACCCGGGTATCTTTGG (SEQ ID NO:49) |
| Smoothelin | GCATCACACAGGCTGGAAC (SEQ ID NO:24) | AGCAGGAGTGTCACTGTGGTC (SEQ ID NO:50) |

TABLE 1-continued

PCR Primers

| | Forward | Reverse |
|---|---|---|
| Calponin | AGCTGGATTGAGGGAC TTACTG (SEQ ID NO:25) | GCATGGAGCGGTTGAT CT (SEQ ID NO:51) |
| Smooth a-actin | TGCTCTGGGTTCGTCA GAGTC (SEQ ID NO:26) | CAGGCAAGTCACTGTG TGGC (SEQ ID NO:52) |
| GATA6 | TTTGCTGCAATCGTCT GAGT (SEQ ID NO:75) | GGAATTCAGACCAGGA AACG (SEQ ID NO:76) |
| Nkx2.5 | TTATGCAGCGTGCAAT GAGT (SEQ ID NO:53) | GAGCTCAGTCCCAGTT CCAA (SEQ ID NO:54) |
| cardiac-troponin-T | GGTCAAGGCAGAACA GAAGC (SEQ ID NO:55) | ATCCAATCCGACAGTT CCTG (SEQ ID NO:56) |
| atrial natriuretic peptide (ANP) | TCTATCCTCTCCTCCA GCCA (SEQ ID NO:57) | CAACAGGTGCAAGAAC AGGA (SEQ ID NO:58) |
| BNP | CAGCGCCTCTAATCCT CTCCT (SEQ ID NO:59) | TATCCCTGGCAGTTCT GAGG (SEQ ID NO:60) |
| cardiac myosin heavy chain (cMHC) | CCTCAAGGGCGGCAA GAA (SEQ ID NO:61) | CCTCAGGATGGGGCAG AT (SEQ ID NO:62) |
| phospholamban protein | CTTTTTCAGCTTTCTC TTG (SEQ ID NO:63) | ACCCCTAGTTCATCCT CA (SEQ ID NO:64) |
| GATA-4 | CTCCTACTCCAGCCCC TACCC (SEQ ID NO:65) | CCTGCTGACGTCTTCG ATTTGTTA (SEQ ID NO:66) |
| Collagen type II | CAGGTGCTGCAAGTCT TCCT (SEQ ID NO:67) | GAAGTCCCTGGAAGCC AG AT (SEQ ID NO:68) |
| Aggrecan | GTTCAAGCCAATCCAC TGGT (SEQ ID NO:69) | CAGTCACACCTGAGCA GCAT (SEQ ID NO:70) |

Immunofluorescence/Immunohistochemistry

For staining of cytoskeleton proteins, cells were fixed with −20° C. methanol for 2 minutes and treated with 0.1% triton X-100 for 15 minutes. For other intracellular molecules, cells were fixed with 4% Paraformaldehyde at room temperature (RT) for 15 minutes and treated with 0.1% triton X-100 for 15 minutes. For cell surface markers, cells were fixed with 4% Paraformaldehyde at RT for 15 minutes. For cell nuclear markers, cells were fixed with 4% Paraformaldehyde at RT for 15 minutes and treated with 0.5% triton X-100 for 30 minutes. Fixed cells were blocked by 0.4% fish gelatin in PBS for 30 minutes and incubated sequentially with primary antibodies for 1 hour at RT and immunofluorescent secondary antibodies for 45 minutes at RT. Nuclei were counterstained with 4',6'-diamino-2-phenylindole (DAPI, D3571 molecular probe). Between each steps, fixed cells were washed with PBS 3 times.

For immunohistochemistry (Jiang, Y. et al. 2002a), fixed cells were blocked by 0.4% fish gelatin in PBS for 30 minutes and incubated sequentially with primary antibodies for I hour at RT and secondary biotinylated antibodies for 45 minutes at RT followed by incubating the samples for 30 minutes in 0.3% $H_2O_2$, 30 minutes with Vectastain ABC reagent and 5 minutes with Peroxidase substrate solution RT. Nuclei were counterstained with 4',6'-diamino-2-phenylindole (DAPI, D3571 molecular probe). Between each step, fixed cells were washed with PBS 3 times.

Fluorescence-Activated Cell Sorting Analysis

For FACS analysis, about 10,000 sMAPCs cells were detached by Trypsin-EDTA, centrifuged at about 1200 rpm for about 5 minutes and suspended in 100 µl PBS. Suspended cells were sequentially incubated with primary antibodies (about 1 µg of primary antibody) and immunofluorescent (e.g., phycoerythrin (PE) or fluoresceine (FITC) coupled) secondary antibodies for 30 minutes at 4° C. Between each step, cells were washed with PBS and resuspended in 100 µl PBS to be analyzed with a FACSCalibur (Becton Dickinson). Table 2 provides an example of FACS settings for one experiment. These parameters are varied based on the negative control (e.g., isotype control) and positive control (e.g., pig blood labeled with CD45, CD44 and MHC Class I and II conjugated with FITC).

TABLE 2

FACS Settings

| Cytometer Type: | FACSCalibur | | | |
|---|---|---|---|---|
| Detector/Amps: | | | | |
| Param | Detector | Voltage | AmpGain | Mode |
| P1 | FSC | E-1 | 4.1 | Lin |
| P2 | SSC | 197 | 1 | Log |
| P3 | FL1 | 325 | 1 | Log |
| P4 | FL2 | 550 | 1 | Log |
| P5 | FL3 | 650 | 1 | Lin |
| P6 | FL2-A | | 1 | Lin |
| P7 | FL2-W | | 1 | Lin |
| Threshold: | | | | |
| Primary Parameter: | | FSC | | |
| Value: | | 52 | | |
| Secondary Parameter: | | None | | |
| Compensation: | | | | |
| FL1 | | 0.0% FL2 | | |
| FL2 | | 0.0% FL1 | | |
| FL2 | | 0.0% FL3 | | |
| FL3 | | 0.0% FL2 | | |

Example 1

Isolation and Culture of Swine MAPCs

For isolation of sMAPCS, the following protocol was followed: Humeri from fetal pigs (about 10 week gestational age) and adults pigs (about 40 days) were excised and incubated in a 1× PBS solution containing 5% BSA for about 36 to about 48 hours at 4° C. BM was flushed from the humeri using a 5% BSA, 1× PBS solution, and bone marrow mononuclear cells (BMMNCs) were isolated by Ficoll-HistoPaque density gradient centrifugation (Histopaq-1077) as described in Reyes M. et al. To isolate sMAPCs, swine BMMNCs were plated on 10 ng/ml fibronectin-coated T 150 flasks at approximately 2×10⁵ cells/cm² in MAPC medium (60% DMEM-LG/ 40% MCDB-201 supplemented with 1× ITS, 0.5× LA-BSA, 0.1 mM ascorbic acid 2-phosphate, 100 U penicillin and 1,000 U streptomycin, and 2% fetal bovine serum (FBS; Hyclone) with 10 ng/ml each hu-PDGF-BB and hu-EGF.

After swine BMMNCs were plated, many of the cells were floating in the medium, these were removed by changing the media. A few of the cells attached to the bottom of the T150 flask and began to proliferate and form colonies with homogenous morphology (initial cells). Once initial colonies formed, cells were recovered by short term trypsinization (less than 1 minute with 0.25% Trypsin-EDTA) and replated at 200 cells/cm$^2$ until small colonies could again be detected. After the second passage (about 9 to 12 days), cells were subcloned at about 1 cell per well in 96 well plates in MAPC medium. Once clones began to proliferate, wells with only 1 clone were selected to be expanded, by detaching cells with a brief incubation with Trypsin-EDTA (for less than two minutes at room temperature with 0.25% Trypsin-EDTA) and plating cells at about 500 cells/cm$^2$. Cells were maintained between 500 and 4,000 cells/cm$^2$. All cultures were maintained at 5.5% $CO_2$, 20% $O_2$ and 37° C.

Figure 1B:
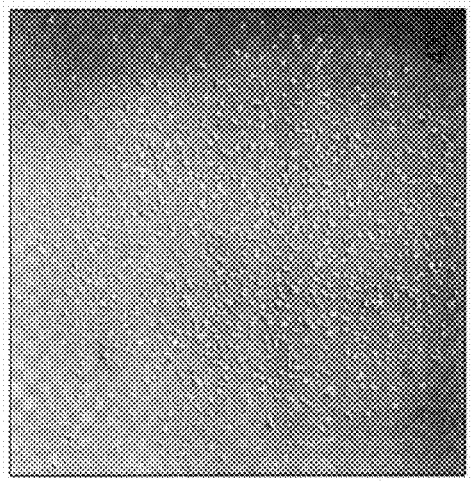
Figure 1C:
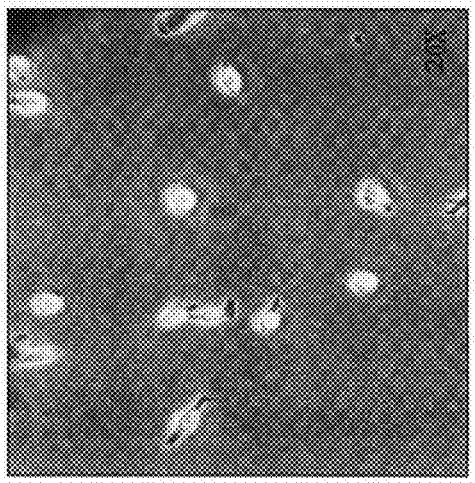

Population doubling (PD) time was 24 h for the initial 30-40 PDs (PDs, as discussed herein, were counted starting from the initial culture), and 36-48 h when cultures reached >40 PD (Figure la). As shown in FIG. 1, sMAPCs were round or triangular, lightly adherent, less than 10 μm in diameter, and exhibited a high nucleus to cytoplasm ratio. During growth, sMAPCs had an instinctive ability to separate from each other following cell division, even in high cell density cultures (FIGS. 1b and 1c). When cultures were allowed to grow to very high densities, proliferation slowed down, demonstrating contact inhibition.

As discussed herein, sMAPCs cultured at low densities (about 250 to about 500 cells/cm$^2$) maintain Oct3a/4 levels, maintain telomere lengths, telomerase activity, and possess the machinery for tri-lineage differentiation.

Example 2

Characterization of Swine MAPCs

Figure 2A:
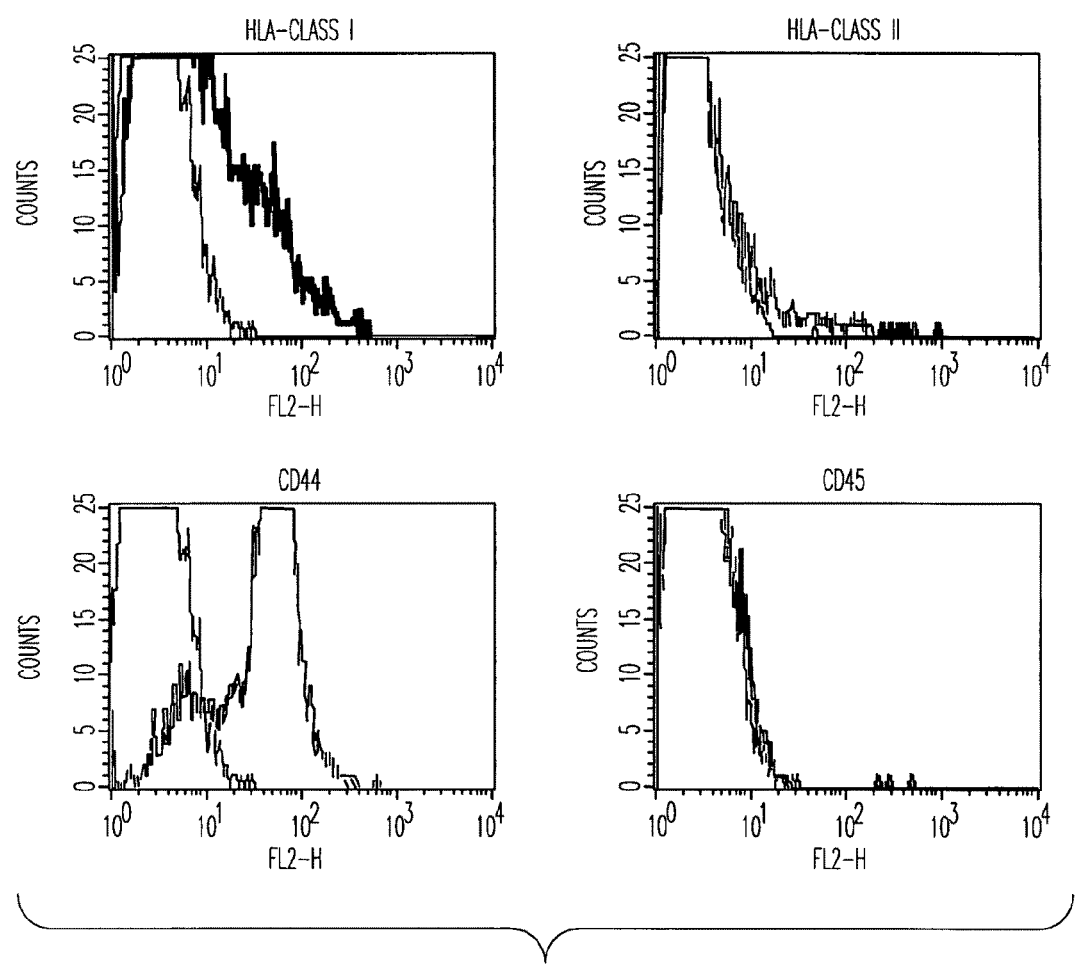
FIG. 2 depicts the results of a FACS analysis. sMAPCs cultured for both about 30 PDs (a) and about 80 PDs (b) population doublings were labeled with FITC-coupled antibodies against HLA-Class I, II, CD44, CD45 or immunoglobulin isotype control antibodies. Cells were analyzed using FACS-Calibur. Black line, control immunoglobulin; Grey line, specific antibody.
Figure 2B:
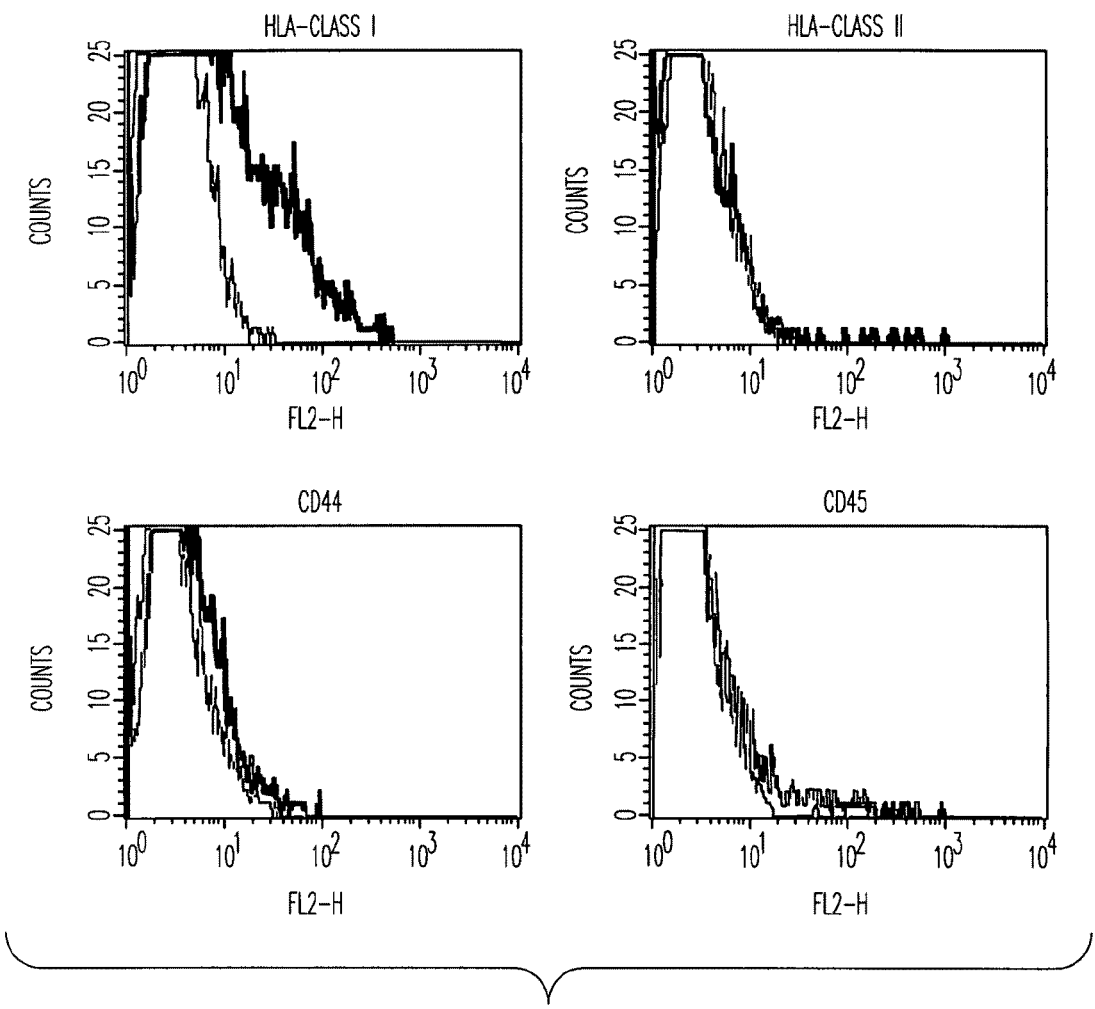
Figure 3A:
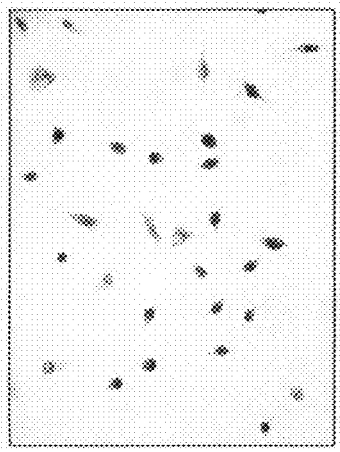
FIG. 3 depicts characterization of sMAPCs. (a) undifferentiated sMAPCs were fixed by 4% paraformaldehyde and stained for Oct-4. (b) Quantitative RT-PCR for Oct-4, Rex-1 and GAPDH. Lane 1, ladder; lane 2, no template control; lane 3, sMAPCs; lane 4, ES cells. (c) an example of sMAPC karyotyping. (d) Telomere length of sMAPCs cultured for 1 (lane 1), 65 (lane 2) and 85 (lane 3) population doublings (PD).
Figure 3B:
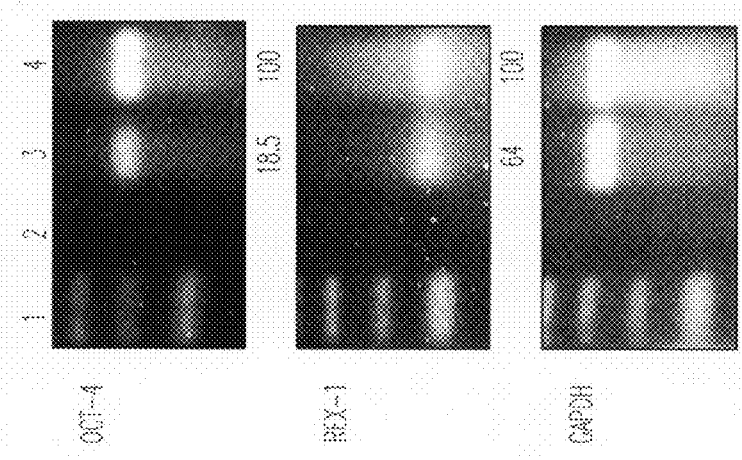

Phenotypic analysis of the cultured cells after 50 PDS indicated a homogenous population of cells that was CD44, CD45, MHC-I and-II negative (FIG. 2a), while cells analyzed prior to 50 PDs were mixed MHC-I and CD44 positive and negative (FIG. 2b). Using primers designed against human ES cell specific Oct 3a, which also identifies swine Oct 3a (determined using testicular swine tissue and confirmed by sequencing), Oct-3a was detected in the sMAPCs at levels of about 1 to about 10% those identified in human ES cells (Oct 3a could not be detected in swine MSCs) (FIG. 3b). The expression of Oct3a in sMAPCs was also confirmed by immunohistochemistry (FIG. 3a). They can also differentiate into three germ layer cell types (as demonstrated by a significant up-regulation of transcription factors and other lineage specific proteins in a time dependent fashion similar to development, measured by Q-RT-PCR as well as immunohistochemistry).

While the cells were not tested for the expression of rox-1, sox-2, SSEA, or LIF-R, these proteins are expressed in other MAPCs, as disclosed in PCT/US/00/21387 (published as WO 01/11011) and PCT/US02/04652 (published as WO 02/064748), which applications and publications are incorporated by reference herein, and such proteins may be expressed in swine cells.

Besides phenotypic analysis, telomere lengths were evaluated at about 1, about 65 and about 85 PDs. No telomere shortening was observed, irrespective of the donor age of the swine from which MAPCs were isolated (FIG. 3d). Moreover, telomere length did not differ between MAPCs isolated from 40 old day swine or swine at gestational age 10 w. In addition, significantly higher levels of telomerase activity could be measured in the sMAPC populations, again irrespective of the age of the donor animal, compared with sMSCs. The results indicate the self-renewal properties of the sMAPCs.

Figure 3C:
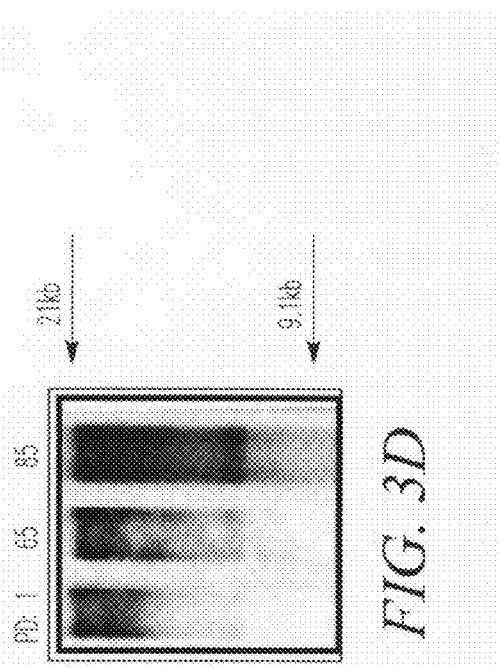
Figure 3D:
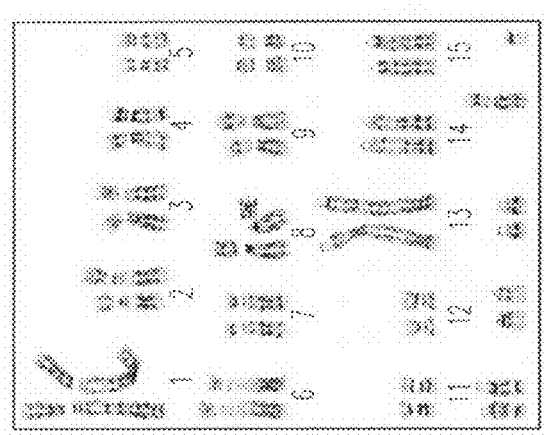

Cytogenetic analysis of cultured cells at 60 PDs, 90PDs and 120 PDs showed that cells were diploid and contained no cytogenetic abnormalities (based on 20 metaphase analyzed per sample) (FIG. 3c).

When established populations of sMAPCs were grown at high confluence (>4,000 cells/cm$^2$) for about 6 PDs, they became morphologically larger. This was associated with acquisition of CD44 and MHC-class I antigens on the cell membrane, and loss of Oct 3a expression by Q-RT-PCR. Additionally, the cells could only differentiate into mesenchymal lineages (e.g., SMCs and chondroblasts), but not endothelium, hepatocyte- or neuron-like cells. When cultures were subsequently replated at low cell densities (about 100 to about 500 cells/cm$^2$) and grown to about 4,000 cells/cm$^2$ for each passage for >5 passages, they did not re-acquire the typical small MAPC morphology, remained CD44 and MHC-class I positive and Oct 3a low, nor were the cells capable of differentiating to cells other than mesenchymnal cells. Finally, cells allowed to grow at high density for several passages and then passed at low densities for 10-20 PDs demonstrated telomere shortening.

Example 3

Differentiation of sMAPCs

Methods of differentiating MAPCs are available in the art (see for example, PCT/US02/04652 (published as WO 02/064748) and PCT/US00/21387 (published as WO 01/11011) which applications and publications are herein incorporated by reference for these methods). The in vitro differentiation capabilities of sMAPCs were evaluated using a fetal and a post-natal sMAPC population, and each differentiation was performed about 5 times at PDs of about 60-100.

The single cell derived sMAPCs described above were tested for their ability to differentiate to chondroblasts, smooth muscle cells, endothelium, neuroectoderm, and endoderm. Differentiation conditions were similar to those described for human and rodent MAPCs (PCT/US0021387 (published as WO 01/11011) and PCT/US02/04652 (published as WO 02/064748)), which are incorporated herein by reference.

A. Chondroblast Differentiation:

1. sMAPCs were cultured in serum free basal medium, 10 ng/ml TGF-β3+10 ng/ml IGF for 10 days followed by 10 ng/ml BMP6 up to day 21 plated at 8×10$^4$ cells/cm$^2$ on matrigel and col I. After 21 days, cultures were evaluated by Q-RT-PCR for collagen type II and agrecan and stained with alcian blue stain. These studies showed that sMAPC can differentiate into cartilage cells expressing high levels of Col-II and agrecan, and staining of the tissue revealed presence of alcian blue.

Figure 4B:
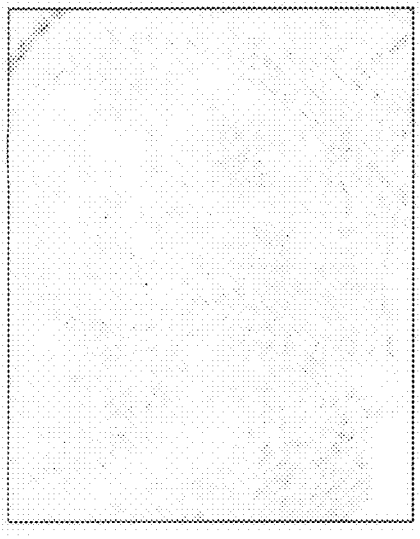
FIG. 4 depicts in vitro differentiation of sMAPCs to phenotypic chondroblast-like cells. 5×10$^5$ sMAPCs (about 60 PDs, about 80 PDs, and about 100 PDs) were cultured in 1 mL MAPC basal medium with 10 ng/ml TGFβ-1 and 100 ng/ml BMP4, in the tip of a 15 ml conical tube and briefly spun to allow aggregation of the cells in micromass suspension culture for 21 days. Cultures were fixed and stained with H&E staining (a) and alcian blue (b) to demonstrate chondroblast cartilage matrix production (c) Chondroblast differentiation was evaluated by RT-PCR for collagen type II and aggrecan transcripts. Lane 1: no template control; Lane 2: undifferentiated sMAPCs; Lane 3: chondroblast differentiation at day 21; Lane 4: pig cartilage tissue (positive control) (Representative example of 12 experiments from 3 donors.)
Figure 4A:
Figure 4C:
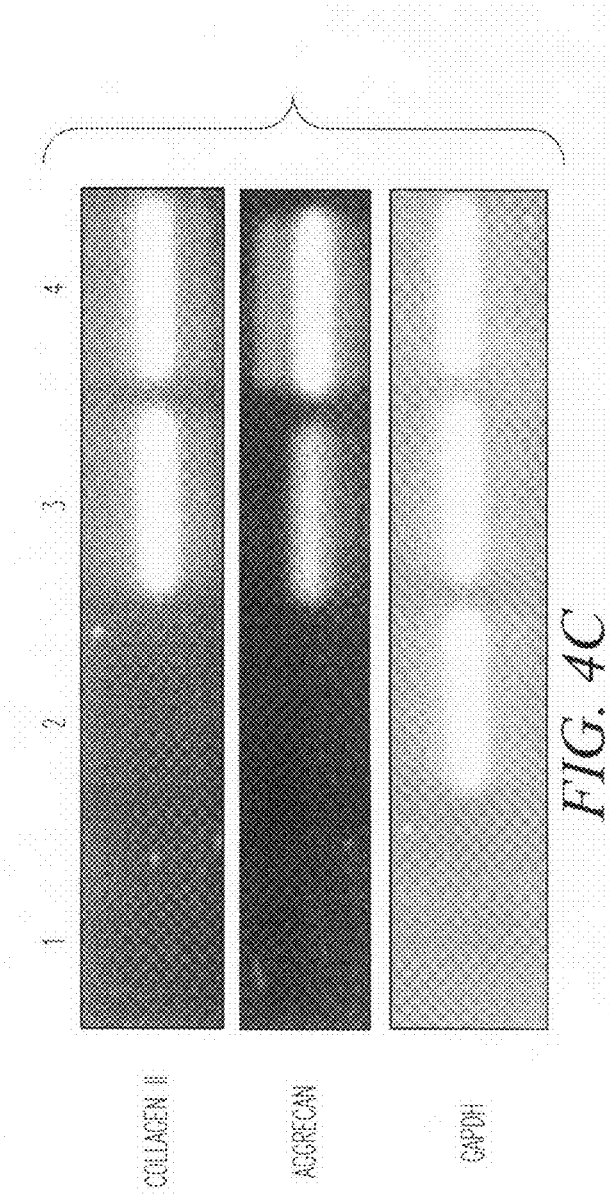

2. 5×10$^5$ sMAPCs were cultured in 1 ml MAPC basal medium (MAPC complete or expansion medium without serum, hu-EGF and hu-PDGF) with 10 ng/ml TGFβ-1 and 100 ng/ml BMP4, in the tip of a 15 ml conical tube and briefly spun to allow aggregation of the cells in micromass suspension culture. Media were changed every 4 days. After 21 days, cultures were evaluated by Q-RT-PCR and for collagen type II and aggrecan transcripts and stained with alcian blue.

sMAPCs took on an early chondrocyte phenotype in response to TGFβ-1 and BMP4. Differentiating cells expressed aggrecan and collagen mRNA and generated alcian blue staining matrix, demonstrating cartilage matrix production (FIG. 4).

Figure 6A:
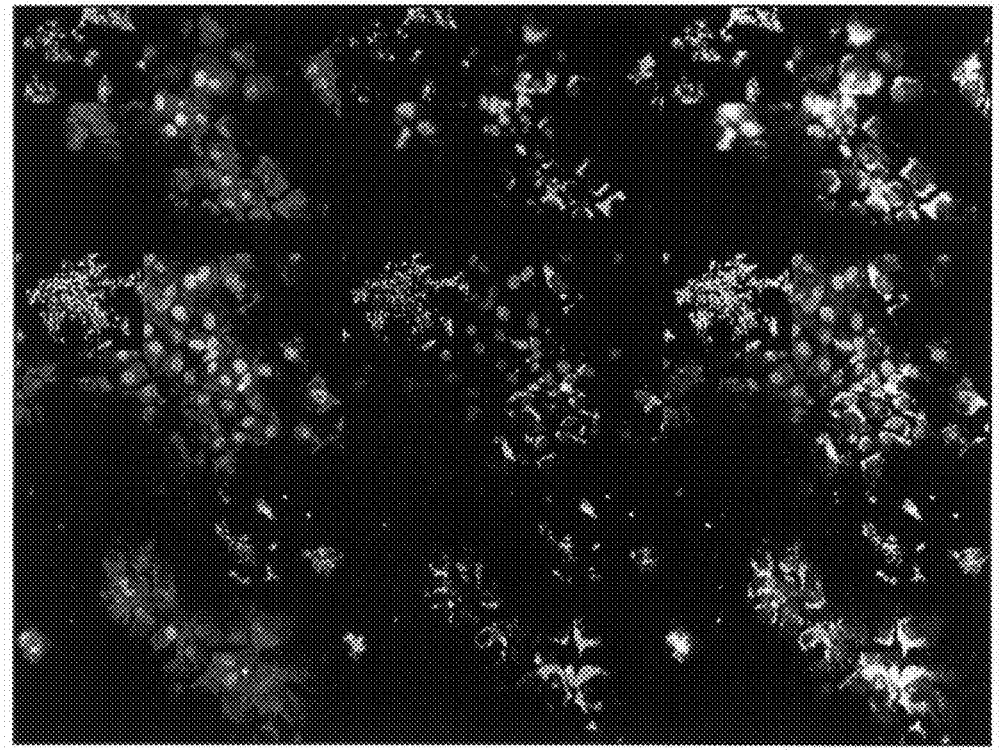
FIG. 6 depicts in vitro differentiation of sMAPCs to phenotypic endothelial-like cells. sMAPCs (about 60 PDs and about 100 PDs) were plated at 50,000 cells/cm$^2$ in FN-coated wells in MAPC basal medium with 100 ng/ml VEGF for 10 days. (a) Cultures were fixed with 4% Paraformaldehyde on day 10 and double stained with anti-vWF labeled with Cy3, anti-CD3 1, VE-Cadherin or VCAM labeled with Cy2, nuclei were stained by DAPI. (b) Differentiation cultures were evaluated by Quantitative PCR for vWF, CD3 1 (PECAM), Flt-1, Flk-1, VE-Cadherin, Tie-1, Tek every three days until day 10. (c) Vascular tube formation by sMAPC derived endothelium-like cells. sMAPC-derived endothelial cells were replated in ECMatrix. After 6 hours, typical vascular tubes could be seen. Representative example of 12 experiments from 3 donors. Magnification: a, ×40; C1, ×4; C2 and C3, ×20.
Figure 6C:
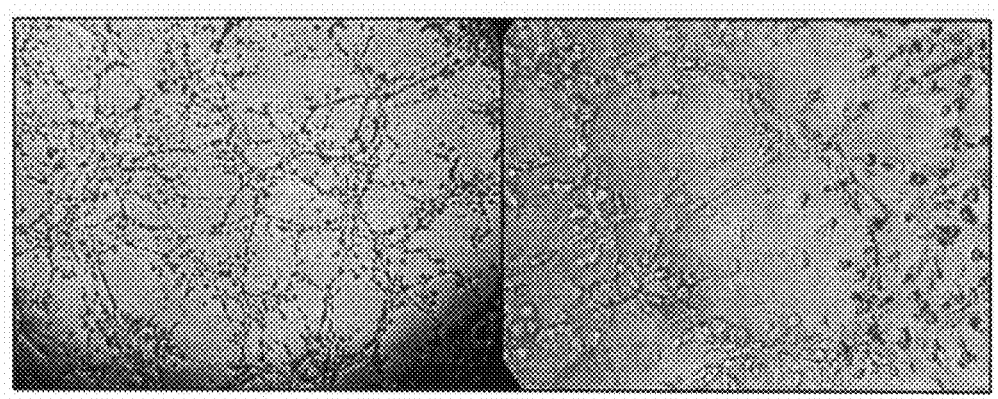
Figure 6B:
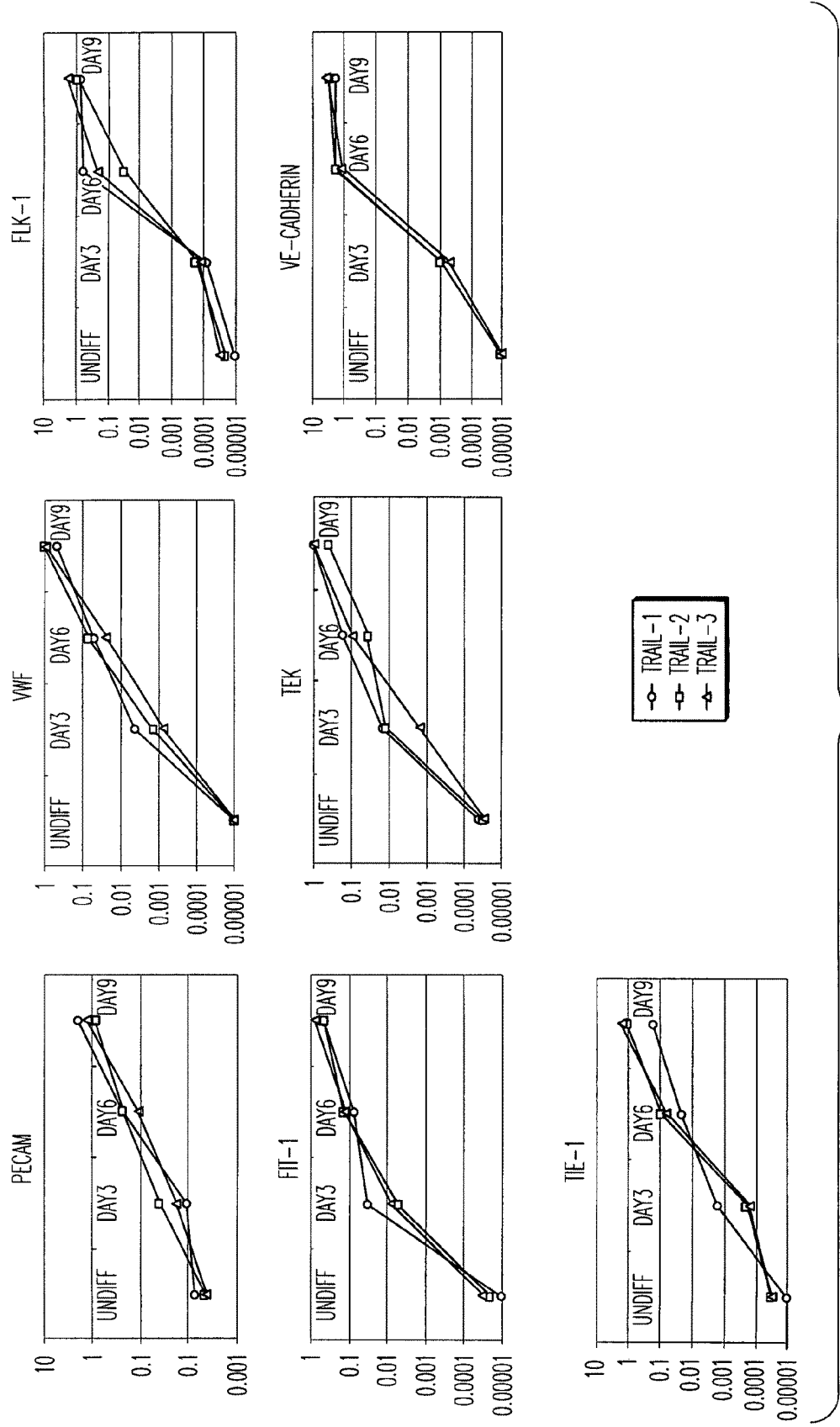
Figure 7A:
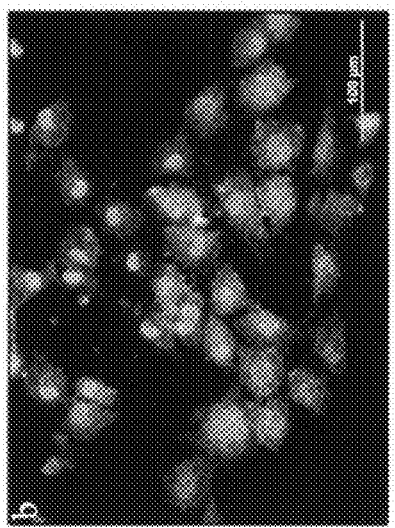
FIG. 7 depicts in vitro differentiation of sMAPCS to phenotypic and functional hepatocyte-like cells. sMAPCs (about 60 PDs and about 100 PDs) were plated at 50,000 cells/cm$^2$ in 2% Matrigel-coated wells in MAPC basal medium with 100 ng/ml HGF and FGF4 for 14 days. (a) Cultures were fixed with 4% Paraformaldehyde on day 14 and double stained with (a) anti-albumin labeled with Cy3, (b) anti-CK18 labeled with Cy2, (c) anti-HNF-1α labeled with Cy3, (d) IgG isotype; nuclei were stained by DAPI. (e) Hepatocyte differentiation cultures were evaluated by Quantitative PCR for Albumin, CYP2B6, CK19, CK18, HNF-3β, HNF-1α every three days until day 12. Representative example of 12 experiments from 3 donors. Magnification: a-d, ×40.
Figure 7B:
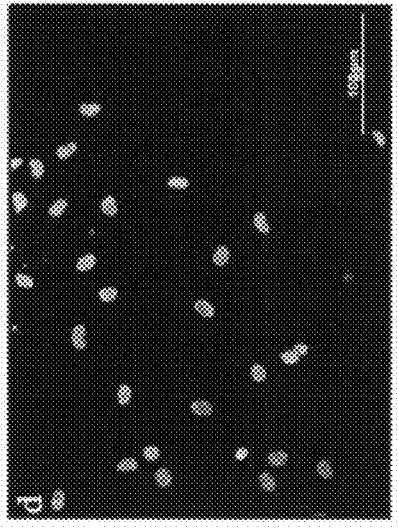
Figure 7C:
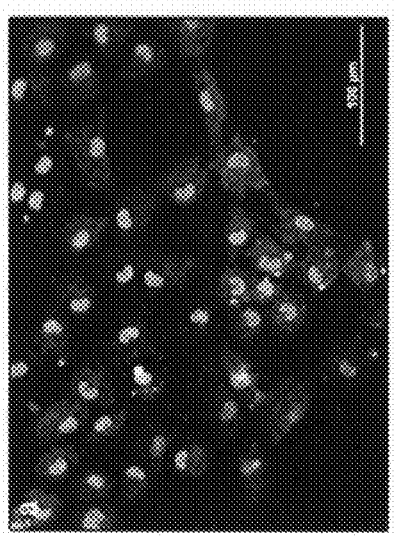
Figure 7D:
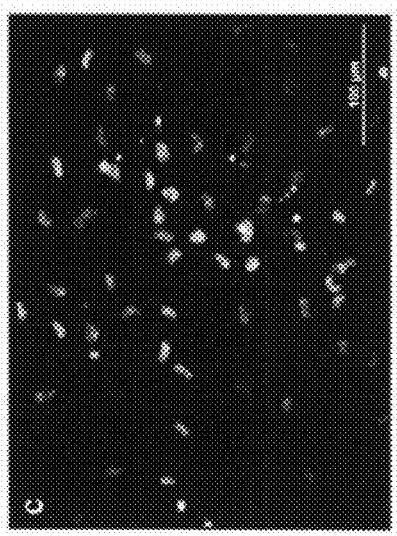
Figure 7E:
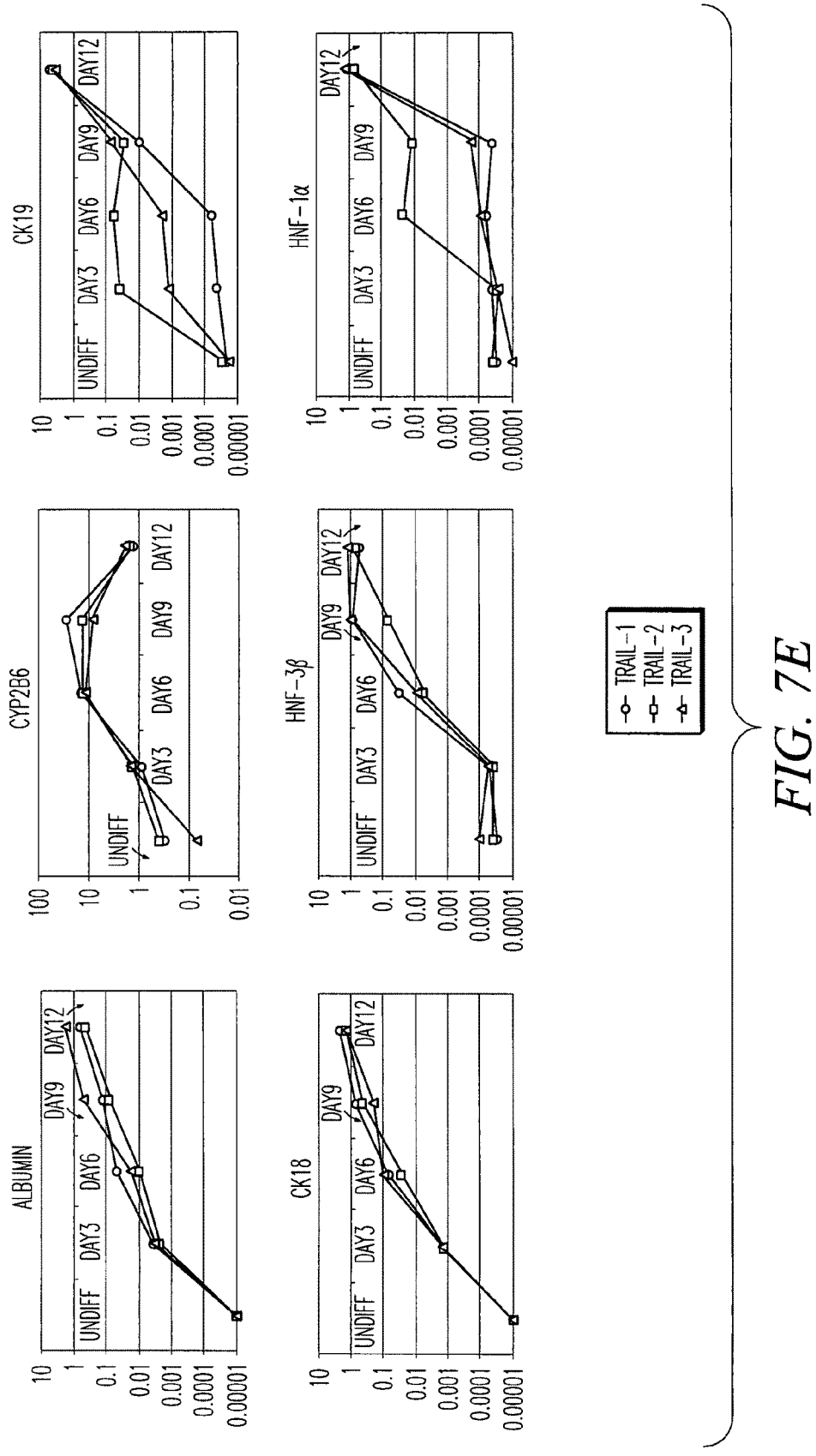

B. Endothelial Differentiation:

sMAPCs were plated at about $5 \times 10^4$ cells/cm$^2$ on fibronectin (FN) coated glass chamber slides in MAPC basal medium supplemented with 100 ng/ml vascular endothelial growth factor (VEGF-165) for 10 days. Subsequently, cells were passed twice in basal medium supplemented with 100 ng/ml of VEGF and 10% FBS. During the differentiation course, fresh media were added every 3 to 4 days. Differentiation cultures were evaluated by Q-RT-PCR for vWF, CD3 1, Flt-1, Flk-1, VE-Cadherin, Tie-1 and Tek every three days until day 10. Differentiated endothelial cells were stained for CD3 1, vWF, VE-Cadherin and Flk1 and evaluated for their ability to form tubes on ECMatrix. Breifely, tube formation was induced by plating sMAPC-endothelial cells using the ECM625 angiogenesis assay (Chemicon) per manufacturer's recommendations.

sMAPCs cultured with VEGF 165 differentiated into endothelium cells expressing vWF, CD31, Flt-1, Flk-1, Tie-1, Tek and VE-Cadherin in a time dependent fashion as determined by Q-RT-PCR, which was confirmed at the protein level for CD31, vWF and VE-Cadherin (FIG. 6). By ten days, the sMAPC endothelium differentiated cells were demonstrated to form vascular tubes in an in vitro angiogenesis assay (ECM625 angiogenesis assay (Chemicon)), whereas undifferentiated sMAPCs did not form tubes on Matrigel (FIG. 6).

Figure 10:
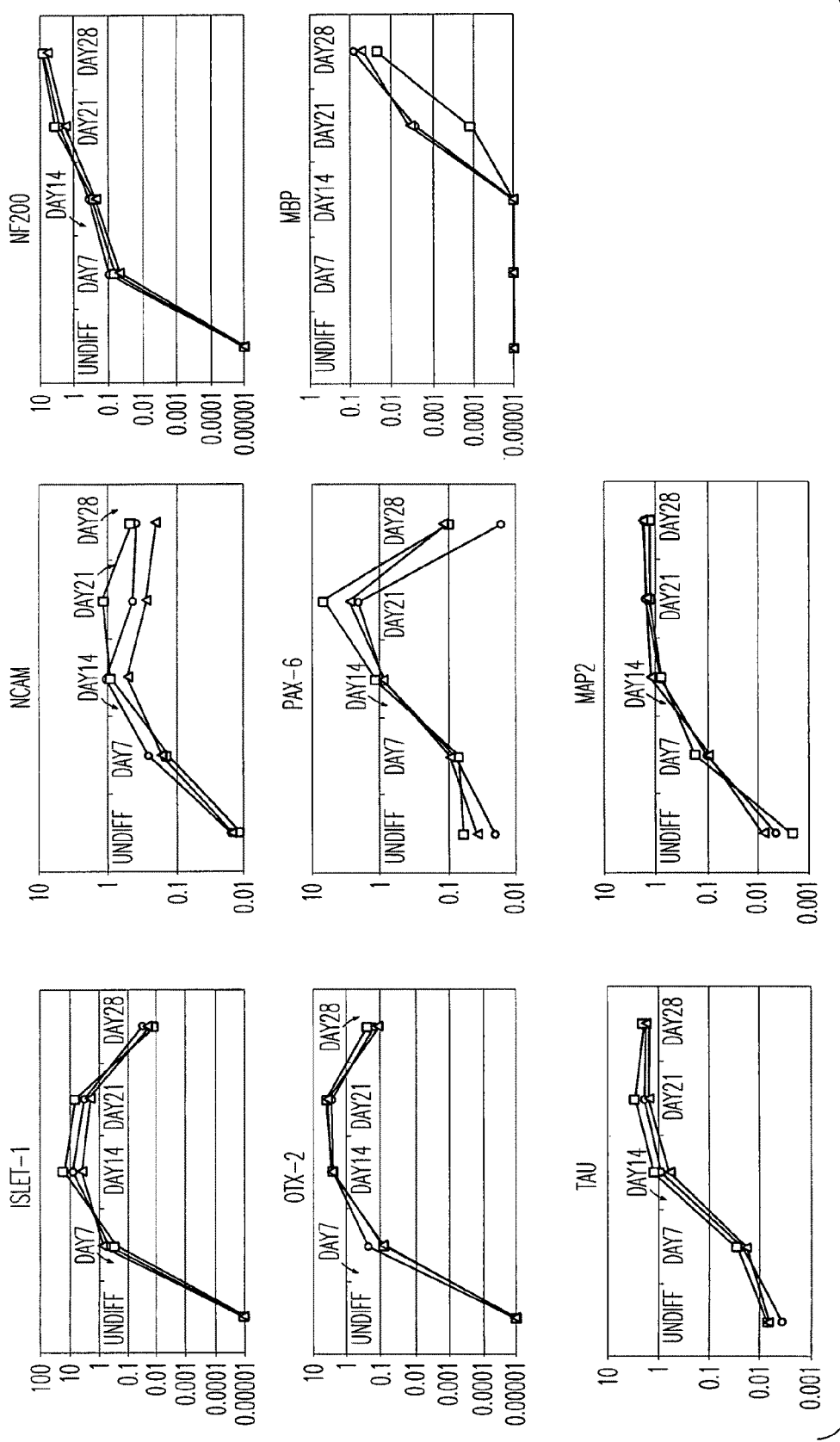
FIG. 10 depicts the evaluation of neuronal differentiation cultures by quantitative PCR for islet-1, NCAM, NF200, OTX-2, PAX-6, MBP, Tau, MAP2 every 7 days until day 28. Representative example of 12 experiments from 3 donors.

C. Neuroectodermal Differentiation:

sMAPCs were plated at about $3 \times 10^3$ cells/cm$^2$ on 10 ng/ml fibronectin (FN) coated coverslips placed inside 6-well plates in complete MAPC medium overnight. Media were then switched to MAPC basal medium supplemented with 100 ng/ml bFGF, 10 ng/ml Noggin, 20 μM Retinoic Acid for 28 days. After 14 days, 10 ng/ml BDNF and GDNF were also added. Half medium media changes occurred every 7 days until day 28. Neural differentiation was evaluated via Q-RT-PCR for early neural transcript factors, Islet-1, Otx-2, Pax-6, as well as NCAM, and more mature neuronal markers such as MAP2, Neuron Filament 200, Tau, MBP and GFAP every 7 days. Cultures were also analyzed via immunofluorescence for NF200, MAP2, Tau, GFAP, S100, Th and Serotonin.

sMAPCs could be induced down a neuroectodermal pathway (FIG. 9). Sequential activation of early neural commitment transcripts was demonstrated by d14 and more mature transcripts, including NF200 and MBP was demonstrated by d28 following culture of sMAPCs with noggin, retinoic acid and bFGF, followed by BDNF and GDNF (FIG. 10). Neuroectoderm like differentiation was confirmed by immunohistochemistry with antibodies against, for example, NF200, Tau, and MAP2 (FIG. 9).

D. Hepatocyte Differentiation:

sMAPCs were plated on 2% Matrigel (Becton-Dickinson and Co., Franklin Lakes, N.J., USA) coated plastic chamber slides at $5 \times 10^4$ cells/cm$^2$ in MAPC basal medium supplemented with 10 ng/ml fibroblast growth factor-4 (FGF-4) and hepatocyte growth factor (HGF) for 12 days. During the differentiation course, fresh media were added every three days. Differentiation cultures were evaluated by Q-RT-PCR for HNF-3b, HNF-1a, CK18, CK19, albumin and CYB2B6 every three days until day 12 (FIG. 7). Also, differentiated cells were fixed with 4% Paraformaldehyde and evaluated by immunofluorescence microscopy for albumin, CK18 and HNF-1 protein expression (FIG. 7).

To assess the function of the hepatocyte like cells, the following assays were performed:

1. Albumin Secretion:

Swine albumin concentrations were determined by an ELISA assay. Concentrations of albumin were determined by generating standard curves from known concentrations of pig albumin. Peroxidase-conjugated and affinity-purified anti-pig albumin and reference pig albumin were from Bethyl Laboratories (E100-110). The ELISA's had a sensitivity of at least 7.8 ng/ml. To verify specificity of results, conditioned medium from endothelial cell differentiations and unconditioned cell expansion medium were assessed and reported negative.

2. Urea secretion: Urea secretion was assessed by a colorimetric assay (DIUR-500 BioAssay Systems) per manufacturer's instructions. Urea with known concentration was used to generate standard curves for assaying sample concentrations. The assay detects urea directly by utilizing substrates that bind specifically urea. Urea reactions were done in 96 well plates and urea concentrations were read by a plate reader. Conditioned medium from endothelial cell differentiations and unconditioned differentiation media were used as negative controls.

3. Periodic Acid Shiff staining (PAS): Slides were oxidized for 5 minutes in 1% periodic acid (PAS) and rinsed several times with ddH$_2$0. Samples were incubated with Schiff's reagent for 15 minutes, then rinsed several times with ddH$_2$O, then immediately counterstained with Hematoxylyin for 1 minute and washed several times with ddH$_2$0.

Figure 8A:
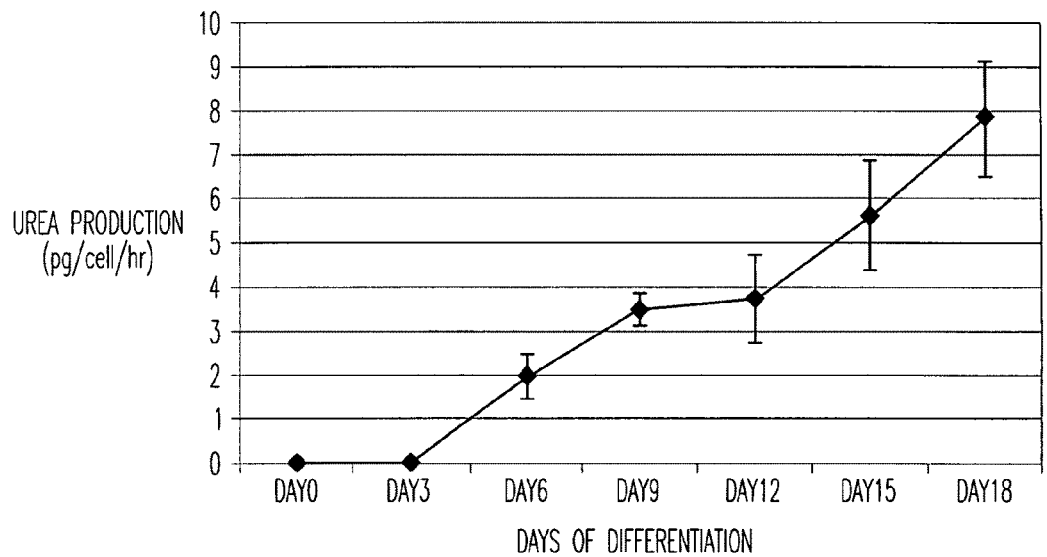
FIG. 8 depicts urea and albumin production and PAS staining by sMAPCs cultured with HGF and FGF on 2% Matrigel (n=5) for 18 days. (a) Urea production, expressed per cell number seeded and per hour. Studies were done in duplicate and repeated twice for each study, samples were examined every 3 days until day 18. (b) Albumin production expressed per cell number seeded and per hour. Studies were done in duplicate and repeated twice for each study, samples were examined every 3 days until day 18. (c) PAS staining.
Figure 8B:
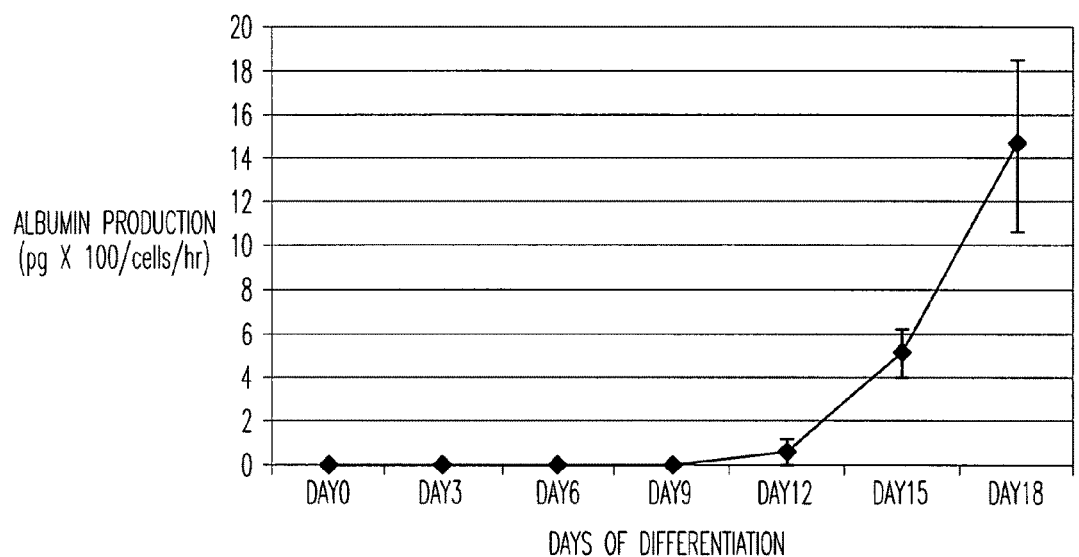
Figure 8C:
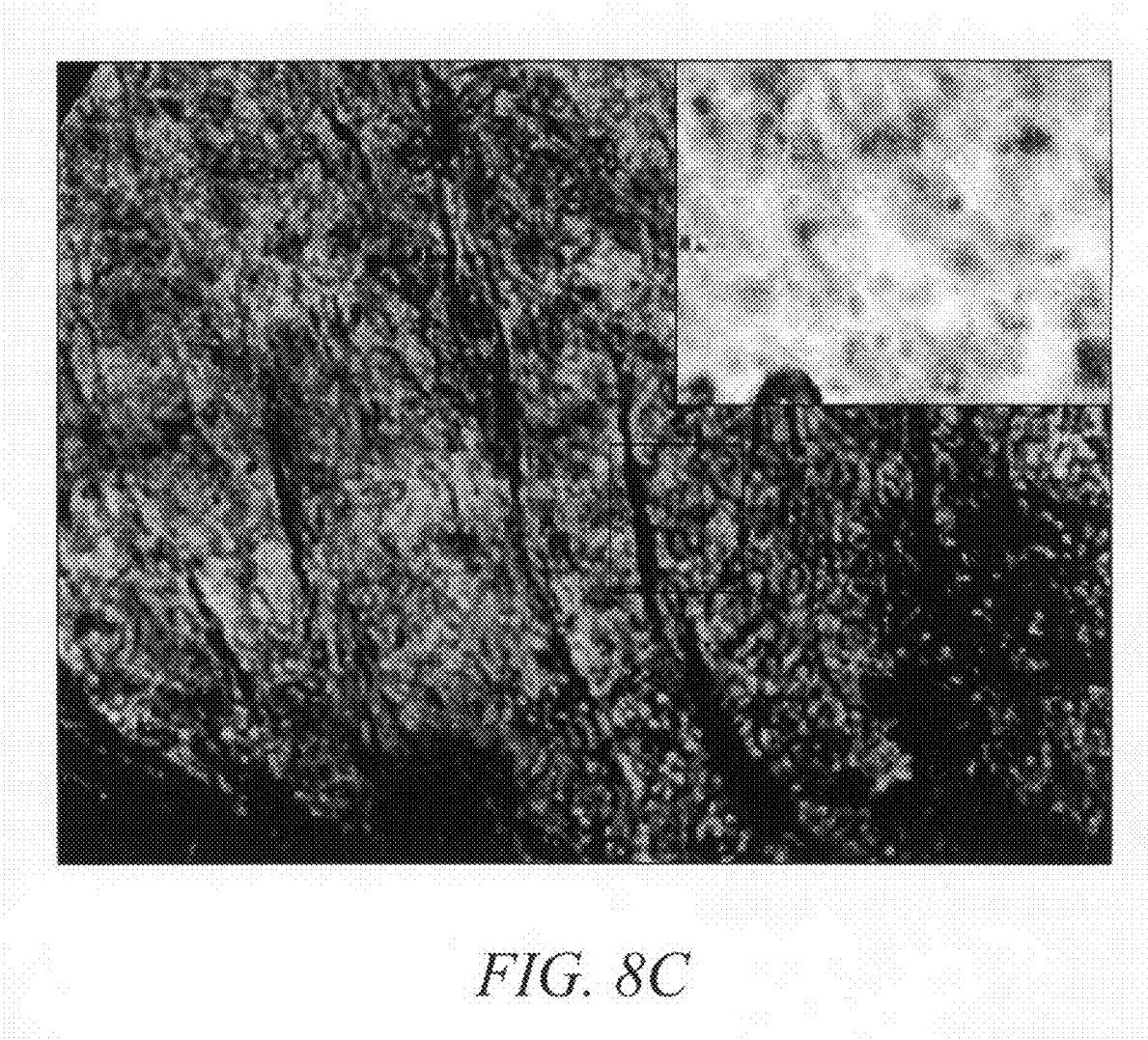
Figure 9J:
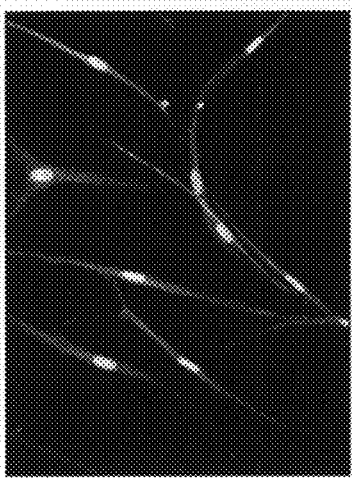
FIG. 9 depicts in vitro differentiation of sMAPCs to phenotypic neuronal-like cells. sMAPCs (about 60 PDs, about 80 PDs and about 100 PDs) were plated at 50,000 cells/cm$^2$ in 6-well plates with FN-coated coverslips in MAPC basal medium with 100 ng/ml bFGF, 10 ng/ml Noggin and 20 μM RA for 28 days. Cultures were fixed on day 14 or 28 and double stained with (a) anti-GFAP labeled with Cy2, (b) anti-S100 labeled with Cy3, (c) overlay of (a) and (b), (d) anti-Tau labeled with Cy2, (e) anti-MAP2 labeled with Cy3, (f) overlay of (d) and (e), (g) anti-TH labeled with Cy2, (h) anti-serotion labeled with Cy3, (i) overlay of (g) and (h). 0) anti-Nf200 labeled with Cy2 on day 14 (k) anti-NF200 labeled with Cy3 on day 28. Nuclei were stained by DAPI, Magnification: a-k, ×40. Representative example of 12 experiments from 3 donors.
Figure 9K:
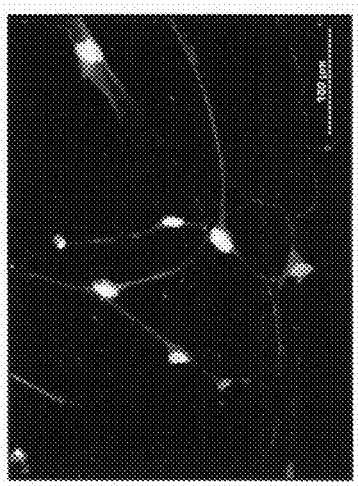
Figure 9C:
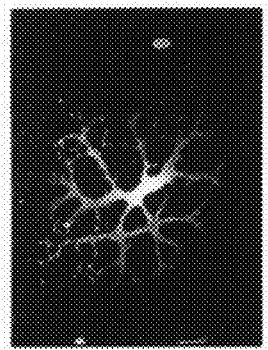
Figure 9B:
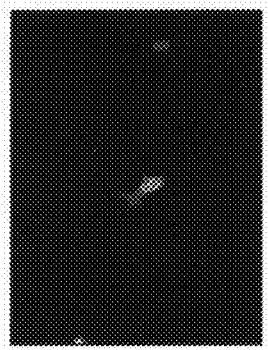
Figure 9A:
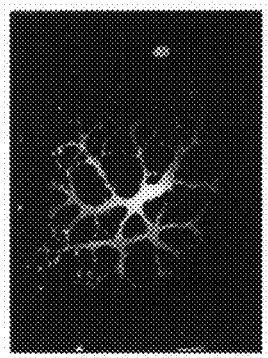
Figure 9F:
Figure 9E:
Figure 9D:
Figure 9I:
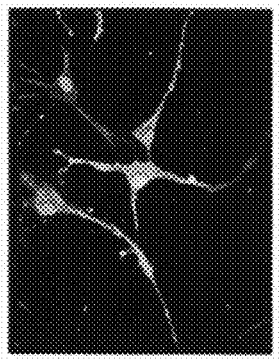
Figure 9H:
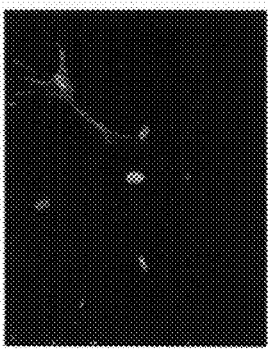
Figure 9G:
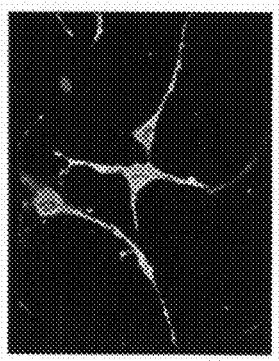

When sMAPCs were cultured with HGF and FGF4, they differentiated into cells with hepatocyte phenotype and function (FIGS. 7 and 8). Using Q-RT-PCR it was demonstrated that sMAPCs express in a time dependent manner, transcription factors (TFs) as well as structural and functional hepatocyte transcripts (FIG. 7). Expression of HNF-1α, Albumin and CK18 was also confirmed at the protein level (FIG. 7). Aside from phenotypic characteristics of hepatocytes, sMAPC-derived cells also had functional characteristics of hepatocytes, including secretion of albumin and urea, and storage of glycogen (FIG. 8).

E. Cardiac Differentiation from MAPC

A number of different schemas to induce cardiomyoblast differentiation from rat, mouse and pig MAPCs were tested. Differentiation was judged by Q-RT-PCR for early and late cardiac muscle. The effect of ECM components (fibronectin, laminin, Matrigel) and combinations of cytokines: including DMSO, 5AZA, activin, Cripto, DKK1, 5AZA, BMP2 and 4, FGF2, 4 and 8, and ascorbic acid1-7 was tested. When sMAPCs were cultured on Matrigel with 0.75% DMSO and 10 ng/ml DKK-1 for 4 days, followed by 10 ng/ml bone morphogenetic protein-2 (BMP2), 80 ng/ml FGF8, 10 ng/ml DKK1, 0.2 mM ascorbic acid on day 4-14, and 100 ng/ml FGF4 from day 14-21, expression of cardiac specific genes was induced, including Nkx2.5, cardiac-troponin-T, atrial natriuretic peptide (ANP) and BNP shown by RT-PCR (FIG. 12). Cardiac myosin heavy chain (cMHC), phospholamban protein and GATA-4 were also detected. Thus, both rodent and swine MAPCs respond to cytokines to express cardiac specific transcripts and proteins, suggesting that immature cardiomyocyte like cells can be generated.

Figure 11:
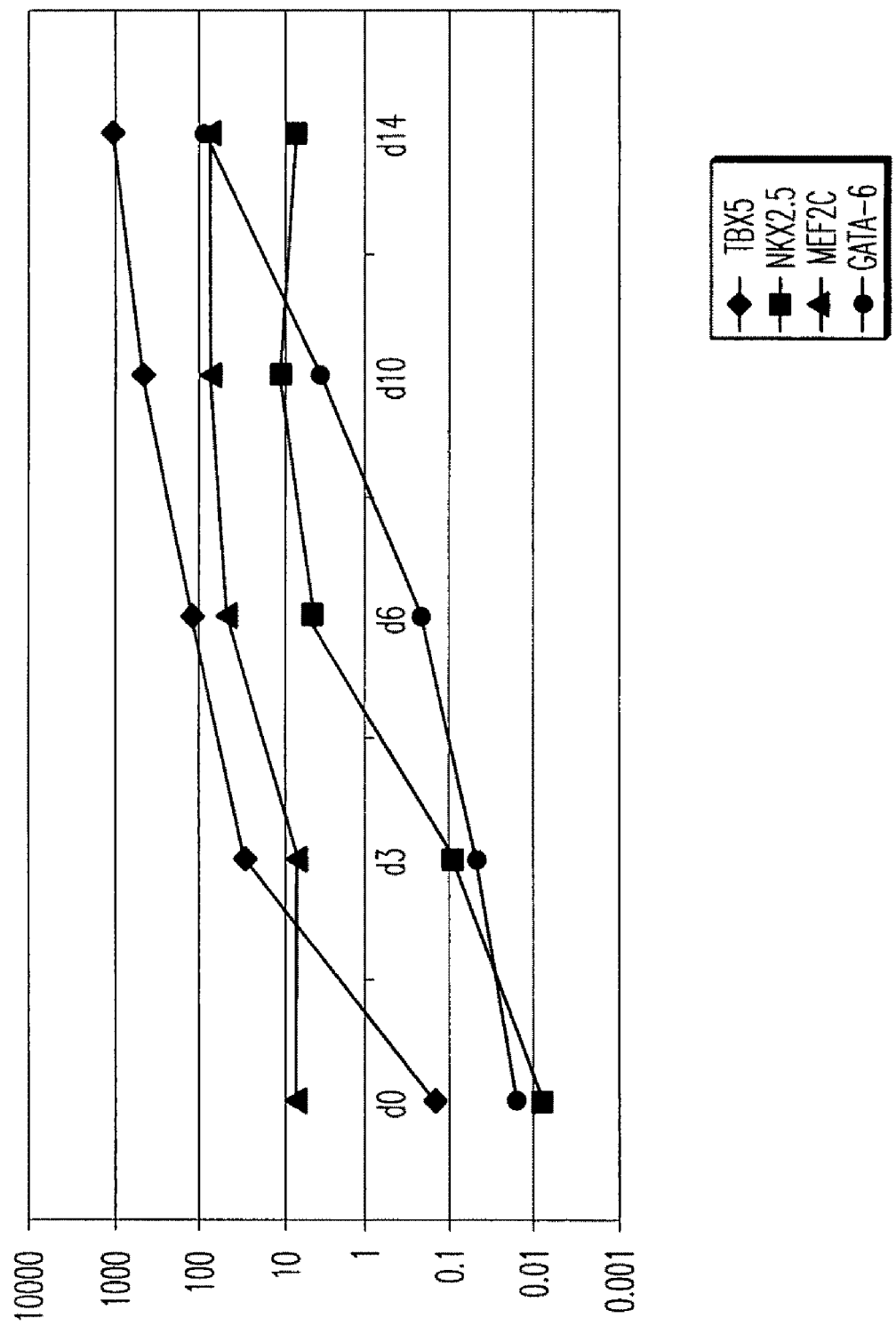
FIG. 11 depicts an evaluation of cardiac differentiation cultures by quantitative PCR.

The results of experiments conducted on sMAPCs plated on FN-coated 6-well plates at 5,000 cells/cm$^2$ and cultured in basal media supplemented with 10 ng/ml BMP2, 10 ng/ml DKK-1 and 80 ng/ml FGF8 for 14 days is presented in FIG. 11.

F. sMAPC Smooth Muscle Differentiation sMAPCs were plated at about $3 \times 10^3$ cells/cm$^2$ in FN-coated wells in MAPC basal medium supplemented with 10 ng/ml PDGF and 5 ng/ml TGF-β1. After 12 days, cells were fixed (with −20° C. methanol) and stained with for the presence of caldesmin, SM22, smooth muscle actin and calponin. Nuclei were stained with DAPI. The cultures were also evaluated by Q-RT-PCR for myocardin, calponin, smooth muscle (SM) actin, and smoothelin. (FIG. 5)

sMPACs differentiated in response to PDGF-BB and TGFβ1 to a SMC like phenotype (FIG. 5). Functional assessment in a single experiment demonstrated that most cells responded to endothelin-1 and bradykinin, with a few cells also responding to carbachol and a few to histamine (the cells displayed significant calcium flux in response to smooth muscle agonists). None responded to norepinephrin, arg-vasopressin, and oxytocin, suggesting that the cells are more immature than the rMAPC derived SM-like cells, which is also consistent with the immunohistochemistry data.

BIBLIOGRAPHY

Abe, A., et al., *J. Virol.* 1998; 72: 6159-6163.
Ahlgren, U., et al., *Genes Dev.* 1998; 12:1763-1768.
Akimenko, M. A., *J Neurosci* 1994; 14:3475-86.
Allen, J. W., et al., *Hepatology* 2001; 34(3):447-55.
Alter B P, *Cancer Genet Cytogenet.* 1992; 58:206-8; discussion 209.
Alvarez-Dolado M., et al. *Nature.* 2003; 425:968-973.
Ang, S. L., et al., *Development* 1993; 119:1301-1315.
Apelqvist, A., *Nature et al.,* 1999; 400:877-881.
Aranguren, X. L., et al. 2005; The arterial and venous potential of human MAPC and AC133 derived endothelial cells is modulated by activation of notch and patched ligands. Keystone Symposium on stem cells.
Babcook, et al., *Proc. Natl. Acad. Sci.* (*USA*). 1996; 93: 7843-7848.
Barker J N and Wagner J E. *Nature Reviews Cancer.* 2003; 3:526-532.
Barker J N et al., *Blood.* 2003; 102:1915-1919.
Barker J N et al., *Blood.* 2004; ePub.
Barnett M J et al., *Blood.* 1994; 84:724-732.
Basch, et. al., *J. Immunol. Methods.* 1983; 56:269.
Batinic, D., et al., *Bone Marrow Transplant.* 1990; 6(2): 103-7.
Ben-Shushan E et al., *Mol Cell Biol.* 1998; 18:1866-1878.
Bertrand J Y et al., *Proc Natl Acad Sci USA.* 2005; 102: 134-139.
Bhardwaj G et al. *Nat Immunol.* 2001; 2:172-180.
Bhatia M et al., *Nat Med.* 1998; 4:1038-1045.
Bhatia R et al., *Blood.* 1995; 85:3636-3645.
Bhatia R et al., *Blood.* 2003; 101:4701-4707.
Bhatia R et al., *J Clin Invest.* 1994; 94:384-391.
Bhushan, A., *Development* 2001; 128:5109-5117.
Bierhuizen, M. et al., *Blood.* 1997; 90(9):3304-3315.
Bird, et al., *Science.* 1988; 242:423-426.
Bittira B, et al. *Eur J Cardiothorac Surg.* 2003; 24:393-398.
Bjorklund L Mea. *Proc Natl Acad Sci USA.* 2002; 99:2344-2349.
Borue X, et al. *Am J Pathol.* 2004; 165:1767-1772.
Bossard, P., and Zaret, K. S. *Development* 1998; 125:4909-4917.
Bredenbeek, P. J., et al. *J Virol.* 1993; 67:6439-6446.
Brice, G. T., et al., *J. Acquir Immune Defic Syndr Hum Retrovirol.* 1998; 19:210-220.
Buckley S et al., *Stem Cells.* 2004.
Cai Z. H., et al., *Artif Organs.* 1988; 12(5):388-93.
Camargo F D et al., *J Clin Invest.* 2004; 113:1266-1270.
Carella A M et al., *Blood Rev.* 1997; 11:154-159.
Cerdan C et al., *Blood.* 2004; 103:2504-2512.
Chambers I et al., *Cell.* 2003; 113:643-655.
Chang, P., et al., *Trends in Biotech.* 1999; 17:78-83.
Chang, T. M., *Artif Organs.* 1992; 16(1):71-4.
Chang, *Blood Purif.* 2000; 18:91-96.
Choi K et al., *Biochem Cell Biol.* 1998; 76:947-956.
Choi K et al., *Development.* 1998; 125:725-732.
Clackson et al. *Nature.* 1991; 352:624-628.
Clarke, *Science.* 2000; 288:1660-3.
Clavel, C., et al., 2005; Isolation and Characterization of Multipotent Adult Progenitor Cells from Cynomologus Monkey, Keystone Symposium on stem cells.
Clothia et al., *J. Mol. Biol.* 11985; 186:651-66, 1985.
Coligan, et al., *Current Protocols in Immunology*, (1991 and 1992).
Cras-Meneur, C., et al., *Diabetes* 2001; 50:1571-1579.
Csemus, V. J., et al., *Cell Mol Life Sci* 1998; 54:733-743.
Dao M A and Nolta J A. *Int J Mol Med.* 1998; 1:257-264.
Davidson, B. L., et al., *Nature Genetics.* 1993; 3:219-223.
Deisseroth A B et al., *Blood.* 1994; 83:3068-3076.
Desai, T. A., *Exp. Opin. Biol. Ther.* 2002; 2:633-646.
Dominguez-Bendala, J., et al., *Diabetes* 2005; 54:720-726.
Douglas, J. et al., *Hum. Gene Ther.* 1999; 10(6):935-945.
Douglas, J., et al. *Nature Biotech.* 1999; 17:470-475.
Drukker M, et al. *Proc Natl Acad Sci USA.* 2002; 99:9864-9869.
Dull, T., et al., *J. Virol.* 1998; 72:8463-8471.
Dyer M A et al., *Development.* 2001; 128:1717-1730.
Eckfeldt C E et al., *PLoS Biology.* 2004.
Embury, J., et al., *Diabetes* 2001; 50:1706-1713.
Faloon P et al., *Development.* 2000; 127:1931-1941.
Ferrari, *Science.* 1998; 279:528-30.
Foerst-Potts, L. *Dev Dyn* 1997; 209:70-84.
Frolov, I., et al. (*Proc. Natl. Acad. Sci. USA.* 1996; 93:11371-11377.
Gambacorti-Passerini C B et al., *Lancet Oncol.* 2003; 4:75-85.
Gittes, G. K., et al., *Development* 1996; 122:439-447.
Gluckman E. *Stem Cells* 1993; 11 Suppl 2:180-3.
Gradwohl, G., et al., *Proc Natl Acad Sci USA.* 2000; 97:1607-1611.
Grant M B et al., *Nat Med.* 2002; 8:607-612.
Guardiola P, et al., *Blood.* 2000; 95:422-9.
Guinan E C et al., *J Pediatr* 1994; 124:144-50.
Gunsilius E et al., *Lancet.* 2000; 355:1688-1691.
Gupta P et al., *Blood.* 1996; 87:3229.
Gupta P et al., *Blood.* 1998; 92:4641-4651.
Gussoni, *Nature.* 1999; 401:390-4.
Hansson, M., et al., *Diabetes* 2004; 53:2603-2609.
Hardikar, A. A., et al., *Proc Natl Acad Sci U.S.A.* 2003; 100:7117-7122.
Harmon, E. B., et al., *Development* 2004; 131:6163-6174.
Harraz M et al., *Stem Cells.* 2001; 19:304-312.
Harris R G et al., *Science.* 2004; 305:90-93.
Hart, A., et al. *Dev Dyn.* 2003; 228:185-193.
Harvey K and Dzierzak E. *Stem Cells.* 2004; 22:253-258.
He T-C et al., *Proc. Natl. Acad. Sci USA.* 1998; 95:2509.
Hebrok, M., et al., *Development* 2000; 127:4905-4913.
Heller, R. S., *Dev Dyn.* 2002; 225:260-270.
Hematti P et al., *PLOS Biology.* 2004; 2:e243.
Hemmati-Brivanlou A et al., *Dev Genet.* 1995; 17:78-89.
Henry, G. L., and Melton, D. A. *Science* 1998; 281:91-96.
Hentsch, B., et al., *Genes Dev.* 1996; 10:70-79.
Heremans Y et al., *J. Cell Biol.* 2002; 159:303.

Hofmann, C., et al. *J. Virol.* 1999; 73:6930-6936.
Hogan C J et al., *Blood.* 1997; 90:85-96.
Hollinger et al., *Proc. Natl. Acad Sci. USA.* 1993; 906444-6448 (1993).
Holmes, et al., *J. Immunol.* 1997; 158:2192-2201.
Holyoake T L et al., *Exp Hematol.* 1999; 27:1418-1427.
Hori and Kim, *PLos Biology* 2005.
Hori, Y., et al., *Proc Natl Acad Sci U.S.A.* 2002; 99:16105-16110.
Howe C W S, Radde-Stepanick T. Hematopoietic Cell Donor Registries. In: Thomas E D, Blume, Karl G. and Forman, Stephan J., ed. Hematopoietic Cell Transplantation. Vol. 2. Malden, Mass.: Blackwell Sciences; 1999:503-512.
Huotari, M. A., et al., *Endocrinology* 2002; 143:4437-4446.
Hurley R W et al., *J Clin Invest.* 1995; 96:511-521.
Jackson, *PNAS USA.* 1999; 96:14482-6.
Jahagirdar, B. N., et al. *Exp Hematol.* 2001; 29(5):543-56.
Jaiswal, R. K. et al., *J Biol Chem.* 2000; 275(13):9645-52.
Jensen, J., et al., *Diabetes* 2000; 49:163-176.
Jiang Y et al., *Blood.* 2000; 95:846-854.
Jiang Y et al., *Proc Natl Acad Sci USA.* 2000; 97:10538-10543.
Jiang Y, et al., *Exp Hematol.* 2002b; 30:896-904.
Jiang Y, et al., *Nature.* 2002a; 418:41-49.
Jiang Y, et al., *Proc Natl Acad Sci USA.* 2003; 100 Suppl 1:11854-11860.
Jiang, Y., et al., *Nature* 2002; 418:41-49.
Jiang, Y., et al., *Exp Hematol.* 2002; 30:896-904.
Johnston, S. A., et al., *Genet. Eng.* (NY) 1993; 15: 225-236.
Jones et al., *Nature.* 1986; 321:522-525.
Jung, J., et al., *Science* 1999; 284:1998-2003.
Kafri, T., et al., *J. Virol.* 1999; 73:576-584.
Kahan, B. W., *Diabetes et al.,* 2003; 52:2016-2024.
Kanai-Azuma, M., et al., *Development* 2002; 129:2367-2379.
Kannagi, R. *EMBO J* 1983; 2:2355-61.
Kantarjian H M et al., *Blood.* 2003; 101:97-100.
Kataoka, K., et al., *J Biol Chem.* 2002; 277:49903-49910.
Kaufman D S et al., *Proc Natl Acad Sci USA.* 2001; 98:10716-10721.
Kawada H, et al. *Blood.* 2004; 104:3581-3587.
Kawaguchi, Y., et al., *Nat Genet.* 2002; 32:128-134.
Keene, C. D., *Cell Transplant.* 2003; 12(3): 201-13.
Keene, C. D., et al., *J Cell Science* 2003; 12:210-213.
Kemahli S et al., *Br J Haematol* 1994; 87:871-2.
Kogler G et al., *J Exp Med.* 2004; 200:123-135.
Kohler & Milstein, *Nature.* 1975; 256:495.
Kohli-Kumar M et al., *Blood.* 84:2050-4, 1994.
Kojima, H., et al., *Nat Med.* 2003; 9:504-505.
Krause D S, et al. *Cell.* 2001; 105:369-377.
Ku, H. T., et al., *Stem Cells* 2004; 22:1205-1217.
Kubo, A., et al. *Development* 2004; 131:1651-1662.
Kusadasi N et al., *Leukemia.* 2002; 16:1782-1790.
Kyba M et al., *Cell.* 2002; 109:29-37.
Kyba M et al., *Proc Natl Acad Sci USA.* 2003; 100, Suppl 1:11904-11910.
Lagasse E, et al. *Nat Med.* 2000; 6:1229-1234.
Lammert, E., et al., *Science* 2001; 294:264-267.
Lanier L L. "NK Cell Recognition." *Annu Rev Immunol.* 2004.
Laquerre, S., et al. *J. Virol.* 1998; 72:9683-9697.
Larrick, et al., *Methods: A Companion to Methods in Enzymology.* (1991).
Lawrence, H. *Blood* 1997; 89:1922.
Lee, S. H., et al., *Nat Biotechnol.* 2000; 18:675-679.
Lefebvre V. *Matrix Biol* 1998; 16:529-40.
Leung A Y H et al., *Dev Biol.* 2004.
Lewis I D et al., *Blood.* 2001; 97:3441-3449.
Lim, J. W. and Bodnar, A., *Proteomics.* 2002; 2(9):1187-1203 (2002).
Liu H J, Lamming C, C. M. V. Characterization of Human Bone Marrow and Umbilical Cord Blood Self-Renewing Multi-lineage Hematopoietic Stem Cells. 2003.
Liu J M: Fanconi's anemia, in Young N S (ed): Bone marrow failure syndromes. Philadelphia, W.B. Saunders company, 2000, p 47-68.
Liu J., et al. *Am J Physiol Heart Circ Physiol.* 2004; 287: H501-511.
Liu, P., et al., *Nat Genet.* 1999; 22:361-366.
Loeffler, J. and Behr, J., *Methods in Enzymology.* 1993; 217:599-618.
Lumelsky, N., et al., *Science* 2001; 292:1389-1394.
Maldonado, T. S., et al., *J Gastrointest Surg.* 2000; 4:269-275.
Marks et al., *J. Mol Biol.* 1991; 222:581-597.
Martin, F., et al., *J. Virol.* 1999; 73:6923-6929.
Matsumoto, K., et al., *Science* 2001; 294:559-563.
Matsuoka, T. A., et al., *Proc Natl Acad Sci (USA)* 2004; 101:2930-2933.
Matthew, H. W., et al., *ASAIO Trans.* 1991; 37(3):M328-30.
Matzuk, M. M., et al., *Nature* 1995; 374:356-360.
McDowell, N., et al., *Curr Biol.* 1997; 7:671-681.
Medvinsky A et al., *Cell.* 1996; 86:897.
Mikkola H K et al., *Blood.* 2003; 101:508-516.
Miller, A. D., and C. Buttimore, *Mol. Cell. Biol.* 1986; 6:2895-2902.
Mochizuki, H., et al., *J. Virol.* 1998; 72:8873-8883.
Molin, M., et al. *J. Virol.* 1998; 72:8358-8361.
Montague, W., and Cook, J. R. *Biochem J.* 1971; 122:115-120.
Morrison et al. *Proc. Natl. Acad Sci.* 1984; 81, 6851-6855.
Movassat, J., et al., *J Clin Endocrinol Metab.* 2002; 87:87.
Muguruma Y et al., *Exp Hematol.* 2003; 31:1323-1330.
Muguruma, Y., et al., *Exp Hematol.* 2003; 31:1323-1330.
Murtaugh, L. C., et al., *Proc Natl Acad Sci U.S.A.* 2003; 100:14920-14925.
Muschler, G. F., et al. *J. Bone Joint Surg. Am.* 1997; 79(11): 1699-709.
Nakano T et al., *Science.* 1994; 265:1098-1101.
Nichols J et al., *Cell.* 1998; 95:379-391.
Nichols, J. et al., *Cell* 1998; 95(3): 379-91.
Norgaard, G. A., et al., *Dev Biol* 2003; 264:323-338.
Novotny and Haber, *Proc. Natl. Acad. Sci. USA.* 1985; 82;4592-4596.
Nusse, R. *Nature* 2001; 411:255-256.
Nyberg, S. L., *Crit Care Med.* 1992:20(8):1157-68.
Offield, M. F., et al., *Development* 1996; 122:983-995.
Ohara-Imaizumi, M., et al., *J Biol Chem.* 2002; 277:50805-50811.
Oostendorp R A et al., *Blood.* 2002; 99:1183-1189.
Oostendorp R A et al., *J Cell Sci.* 2002; 115:2099-2108.
Otonkoski, T., et al., *J Clin Invest.* 1993; 92:1459-1466.
Pack, et al., *Bio/Technology.* 1993; 11:1271-77.
Packer, A. I., *Dev Dyn* 2000; 17:62-74.
Persons, D., et al., *Nature Medicine.* 1998; 4:1201-1205.
Petersen, H. V., et al., *Mol Cell Biol Res Commun.* 2000; 3:249-254.
Petersen, *Science.* 1999; 284:1168-1170.
Pittenger, *Science* 1999; 284:143-147.
Pittenger, M. F. and B. J. Martin, *Circ Res.* 2004; 95(1):9-20.

Pittenger, M. F. et al., *Curr Top Microbiol Immunol.* 2000; 251: 3-11.
Potocnik A J et al., *Proc Natl Acad Sci USA.* 1997; 94:10295-10300.
Presta, *Curr. Op. Struct. Biol.* 1992; 2:593-596.
Punzel M et al., *Blood.* 1999; 93:3750-3756.
Rackoff W R et al., *Blood.* 1996; 88:1588-93.
Rajagopal, J., et al. *Science* 2003; 299:363.
Rebel V I et al., *Blood.* 1996; 87:3500-3507.
Reichmann et al., *Nature.* 1988; 332:323-329.
Rescan, C., et al., *Lab Invest.* 2005; 85:65-74.
Reya T et al., *Nature.* 2003; 423:409-414.
Reyes M et al., *Ann NY Acad Sci.* 2001; 938:231-233; discussion 233-235.
Reyes, M., et al., *Blood* 2001; 98:2615-2625.
Reyes, M., et al., *J Clin Invest.* 2002; 109:337-346.
Rideout W Mr et al. *Cell.* 2002; 109:17-27.
Robbins, et al. *J. Virol.* 1997; 71(12):9466-9474.
Rojas, E., et al., *FEBS Lett.* 1990; 261:265-270.
Rosario, L. M., et al., *Adv Exp Med Biol.* 1986; 211:413-425.
Rosfjord E, Rizzino A. *Biochem Biophys Res Commun.* 1997; 203:1795-802.
Rowley J. *Cancer.* 1990; 65:2178-2184.
Rozga, J., et al,. *Ann Surg.,* 1994; 219(5):538-46.
Salmons, B. and Gunzburg, W. H., 1993; 4:129-141.
Sander, M., et al., *Development* 2000; 127:5533-5540.
Sander, M., et al., *Genes Dev.* 1997; 11:1662-1673.
Sanvito, F., et al., *Development* 1994; 1994:3451-3462.
Sawai, K., et al., *Mol Genet Metab.* 1998; 64:44-51.
Scagni P et al., *Haematologica* 1988; 83:432-7.
Schuh A C, et al., *Proc Natl Acad Sci USA.* 1999; 96:2159-2164.
Schwartz R E et al., *J Clin Investigation.* 2002; 96:1291-1302.
Schwartz R E, et al. *J Clin Invest.* 2002; 109:1291-1302.
Schwarzenberger, P., et al., *J. Virol.* 1997; 71:8563-8571.
Sebestyen, et al. *Nature Biotech.* 1998; 16:80-85.
Shen, C. N., et al., *Nat Cell Biol.* 2000; 2:879-887.
Shimozaki et al. *Development.* 2003; 130:2505-12.
Sipione, S., et al. *Diabetologia* 2004; 47:499-508.
Smith, S. B., et al., *Mol Cell Biol.* 1999; 19:8272-8280.
Soria, B., et al., *Diabetes* 2000; 49:157-162.
Sosa-Pineda, B., et al., *Nature* 1997; 386:399-402.
Spangrude G et al., *Science.* 1988; 241:58.
Sussel, L., et al., *Development* 1998; 125:2213-2221.
Sutton, R., et al., *J. Virol.* 1998; 72:5781-5788.
Takahashi, *J Clin Invest.* 2000; 105:71-7.
Takahashi, *Nat Med.* 1999; 5:434-8.
Theise, *Hepatology.* 2000a; 31:235-40.
Theise, *Hepatology.* 2000b; 32:11-6.
Theunissen K and Verfaillie C M. *Exp Hematol.* 2004.
Thomas E et al., *Ann Int Med.* 1986; 104:155-163.
Thomas E D. *Semin Hematol.* 1999; 36:95-103.
Thomson J A et al., *Science.* 1998; 282:1145-1147.
Tian X et al., *Exp Hematol.* 2004; 32:1000-1009.
Tolar J et al., *Blood.* 2003; ASH Abstract.
Traggiai E et al., *Science.* 2004; 304:104-107.
Trube, G., et al., *Pflugers Arch.* 1986; 407: 493-499.
Tsuchida, K., et al., *Mol Cell Endocrinol.* 2004; 220:59-65.
Uwanogho D. et al., *Mech Dev* 1995; 49:23-36.

Van Tendeloo, et al., *Blood* 2001 et al., 98:49-56.
Van Tendeloo, et al., *Gene Ther.* 2000; 7:1431-1437.
Vaswani, et al., Annals Allergy, Asthma & Immunol. 1998; 81:105-115.
Verfaillie C et al., *Blood.* 1992; 79:1003-1010.
Verfaillie C et al., *Blood.* 1998; 92:1820-1831.
Verfaillie C et al., *J Exp Med.* 1991; 174:693-703.
Verfaillie C. *Blood.* 1992; 79:2821-2826.
Verfaillie C M et al., *J Clin Invest.* 1992; 90:1232.
Verfaillie C M, et al., *Blood.* 1996; 87:4770-4779.
Verfaillie, C. M. Trends Cell Biol. 2002; 12(11):502-8.
Vodyanik M A et al., *Blood.* 2005; 105:617-626.
Wagers A J, et al. *Science.* 2002; 297:2256-2259.
Wagner, E., et al., *Proc. Natl. Acad. Sci. USA.* 1992; 89:6099-6103.
Wang L et al., *Immunity.* 2004; 21:31-41.
Wang X et al., *Nature.* 2003; 422:897-901.
Weber, H., et al., *Development* 2000; 127:4345-4360.
Wells, J. M., and Melton, D. A. *Development* 2000; 127: 1563-1572.
Whitlow, et al., *Methods: A Companion to Methods in Enzymology* (1991).
Williams, R. S., et al., *Proc. Natl. Acad. Sci. USA.* 1991; 88:2726-2730.
Winnier, G., et al., *Genes Dev.* 1995; 9:2105-2116.
Wold, W., Adenovirus Methods and Protocols, Humana Methods in Molecular Medicine (1998), Blackwell Science, Ltd.
Wu G D, et al. *Transplantation.* 2003; 75:679-685.
Wysocki and Sato, *Proc. Natl. Acad. Sci. (USA).* 1978; 75:2844.
Xiong, C., et al., *Science.* 1989; 243:1188-1191.
Yahata T et al., *J Immunol.* 2002; 69:204-209.
Yanagi, K., et al., *ASAIO Trans.* 1989; 35(3):570-2.
Yang, N. S., et al., *Proc. Natl. Acad. Sci. USA.* 1990; 87:9568-9572.
Yoder M et al., *Proc Natl Acad Sci USA.* 1997; 94:6776.
Zaret, K. S. *Mech Dev.* 2000; 15:83-88.
Zeng L et al., *Blood.* 2004; ASH abstract.
Zeng, L., et al., *Blood ASH Abstract* 2004.
Zhang, G. et al., *Biochem. Biophys. Res. Commun.* 1996; 227(3):707-711.
Zhao L R, et al. *Exp Neurol.* 2002; 174:11-20.
Zhao R et al., *Blood.* 1997; 90:4687-4698.
Zhao RCH et al., *Blood.* 2001; 97:2406-2412.
Zhao, L., et al., *J Biol Chem.* 2005; 280:11887-11894.
Zhou, X., et al., *Nature* 1993; 361:543-547.

All publications, patents and patent applications are incorporated herein by reference. While in the foregoing specification this invention has been described in relation to certain preferred embodiments thereof, and many details have been set forth for purposes of illustration, it will be apparent to those skilled in the art that the invention is susceptible to additional embodiments and that certain of the details described herein may be varied considerably without departing from the basic principles of the invention.

What is claimed is:

1. A cell culture comprising isolated expanded swine multipotent, non-embryonic, non-germ, cells that can differentiate into at least one cell type of each of the endodermal, ectodermal, and mesodermal embryonic lineages and express telomerase, said cells having undergone at least 10-40 cell doublings in culture, wherein said cells express octamer binding transcription factor 3a (Oct 3a).

2. A cell culture comprising isolated expanded swine multipotent, non-embryonic, non-germ, cells that can differentiate into at least one cell type of each of the endodermal, ectodermal, and mesodermal embryonic lineages, express telomerase, and have been obtained by culture of non-embryonic, non-germ tissue, the cells expressing telomerase having undergone at least 10-40 cell doublings in culture, wherein said cells express octamer binding transcription factor 3a (Oct 3a).

3. The cell culture of claim 1 or 2, wherein the cells expressing telomerase have undergone 10 cell doublings.

4. The cell culture of claim 1 or 2, wherein the cells expressing telomerase have undergone 20 cell doublings.

5. The cell culture of claim 1 or 2, wherein the cells expressing telomerase have undergone 30 cell doublings.

6. The cell culture of claim 1 or 2, wherein the cells expressing telomerase have undergone 40 cell doublings.

7. The cell culture of claim 1 or 2, wherein the cells are genetically modified.

8. The cell culture of claim 7, wherein the modification comprises introducing a selectable or screenable marker gene into the cells.

9. A pharmaceutical composition comprising a pharmaceutically acceptable carrier and isolated expanded swine multipotent, non-embryonic, non-germ cells of claim 1 or 2 that can differentiate into at least one cell type of each of the endodermal, ectodermal, and mesodermal embryonic lineages and express telomerase, said cells having undergone at least 10-40 cell doublings in culture.

10. A method for making a pharmaceutical composition comprising admixing a pharmaceutically acceptable carrier and isolated expanded swine multipotent, non-embryonic, non-germ cells of claim 1 or 2 that can differentiate into at least one cell type of each of the endodermal, ectodermal, and mesodermal embryonic lineages and express telomerase, said cells having undergone at least 10-40 cell doublings in culture.

11. A method for making a cell culture, said method comprising introducing the cells of claim 1 or 2 into a cell culture medium and expanding said cells in culture.

12. The cell culture of claim 1 or 2, wherein the cells expressing telomerase have undergone greater than 40 cell doublings.

13. The cell culture of claim 1 or 2, wherein the cells expressing telomerase are derived from bone marrow.

* * * * *